US009090586B2

(12) United States Patent
Yoshikawa et al.

(10) Patent No.: US 9,090,586 B2
(45) Date of Patent: Jul. 28, 2015

(54) HETEROCYCLIC COMPOUND

(75) Inventors: Masato Yoshikawa, Kanagawa (JP);
Shinkichi Suzuki, Kanagawa (JP);
Tomoaki Hasui, Kanagawa (JP);
Makoto Fushimi, Kanagawa (JP); Jun Kunitomo, Kanagawa (JP); Haruhi Kamisaki, Kanagawa (JP); Takahiko Taniguchi, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 13/813,786

(22) PCT Filed: Aug. 3, 2011

(86) PCT No.: PCT/JP2011/067809
§ 371 (c)(1),
(2), (4) Date: Feb. 22, 2013

(87) PCT Pub. No.: WO2012/018059
PCT Pub. Date: Feb. 9, 2012

(65) Prior Publication Data
US 2013/0150344 A1  Jun. 13, 2013

(30) Foreign Application Priority Data

Aug. 4, 2010  (JP) .................. 2010-175374

(51) Int. Cl.
| | | |
|---|---|---|
| A61K 31/553 | (2006.01) | |
| A61K 31/525 | (2006.01) | |
| A61K 31/535 | (2006.01) | |
| C07D 401/00 | (2006.01) | |
| C07D 498/02 | (2006.01) | |
| C07D 413/00 | (2006.01) | |
| C07D 241/00 | (2006.01) | |
| C07D 413/14 | (2006.01) | |
| C07D 498/08 | (2006.01) | |
| C07D 417/14 | (2006.01) | |
| C07D 403/14 | (2006.01) | |
| A61K 9/20 | (2006.01) | |
| C07D 403/04 | (2006.01) | |
| A61K 9/00 | (2006.01) | |
| C07D 401/14 | (2006.01) | |

(52) U.S. Cl.
CPC ............... *C07D 403/04* (2013.01); *A61K 9/00* (2013.01); *A61K 9/2018* (2013.01); *A61K 9/2059* (2013.01); *C07D 401/14* (2013.01); *C07D 403/14* (2013.01); *C07D 413/14* (2013.01); *C07D 417/14* (2013.01); *C07D 498/08* (2013.01)

(58) Field of Classification Search
USPC .............. 514/211.15, 252.05, 230.5, 236.5; 544/238, 105, 114, 230
See application file for complete search history.

(56) References Cited

U.S. PATENT DOCUMENTS

| | | |
|---|---|---|
| 5,455,252 A | 10/1995 | Wilhelm et al. |
| 2009/0281107 A1 | 11/2009 | Congy et al. |
| 2010/0152193 A1 | 6/2010 | Alberati et al. |
| 2010/0197651 A1* | 8/2010 | Taniguchi et al. ....... 514/210.02 |
| 2012/0028951 A1 | 2/2012 | Taniguchi et al. |
| 2012/0277430 A1 | 11/2012 | Taniguchi et al. |
| 2012/0277431 A1 | 11/2012 | Taniguchi et al. |

FOREIGN PATENT DOCUMENTS

| | | |
|---|---|---|
| JP | 8-511238 | 11/1996 |
| JP | 2010-510297 | 4/2010 |
| WO | 2010/063610 | 6/2010 |
| WO | 2010/090737 | 8/2010 |
| WO | 2012/018058 | 2/2012 |
| WO | 2012/020780 | 2/2012 |

OTHER PUBLICATIONS

International Search Report issued Sep. 27, 2011 in International (PCT) Application No. PCT/JP2011/067809.
F. S. Menniti et al., "Phosphodiesterases in the CNS: Targets for Drug Development", Nat. Rev. Drug Disc., vol. 5, pp. 660-670, Aug. 2006.
M. D. Houslay et al., "cAMP-Specific Phosphodiesterase-4 Enzymes in the Cardiovascular System: A Molecular Toolbox for Generating Compartmentalized cAMP Signaling", Circulation Research, vol. 100, No. 7, pp. 950-966, 2007.

(Continued)

*Primary Examiner* — Jeffrey H Murray
*Assistant Examiner* — Oluwafemi Masha
(74) *Attorney, Agent, or Firm* — Wenderoth, Lind & Ponack, L.L.P.

(57) ABSTRACT

The present invention provides a compound represented by the formula (1):

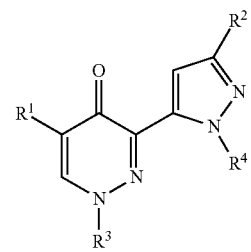

wherein each symbol is as defined in the specification, or a salt thereof, a prodrug of the compound or a salt thereof, a medicament containing the compound or a salt thereof, the medicament which is a phosphodiesterase 10A inhibitor, and a medicament which is for preventing or treating schizophrenia.

12 Claims, 1 Drawing Sheet

(56) References Cited

OTHER PUBLICATIONS

J. Nakayama et al., "Expression Cloning of a Human α1,4-N-acetylglucosaminyltransferase that forms GlcNAcα1→4Galβ→R, A Glycan Specifically Expressed in the Gastric Gland Mucous Cell-Type Mucin", Proc. Natl. Acad. Sci., vol. 96, pp. 8991-8996, Aug. 1999.

K. Fujishige et al., "Cloning and Characterization of a Novel Human Phosphodiesterase that Hydrolyzes both cAMP and cGMP (PDE10A)", The Journal of Biological Chemistry, vol. 274, No. 26, pp. 18438-18445, 1999.

K. Loughney et al., "Isolation and Characterization of PDE10A, A Novel Human 3', 5'-cyclic Nucleotide Phosphodiesterase", Gene, vol. 234, pp. 109-117, 1999.

K. Fujishige et al., "Striatum- and Testis-Specific Phosphodiesterase PDE10A Isolation and Characterization of a Rat PDE10A", Eur. J. Biochem., vol. 266, pp. 1118-1127, 1999.

T. F. Seeger et al., "Immunohistochemical Localization of PDE10A in the Rat Brain", Brain Research, vol. 985, pp. 113-126, 2003.

* cited by examiner

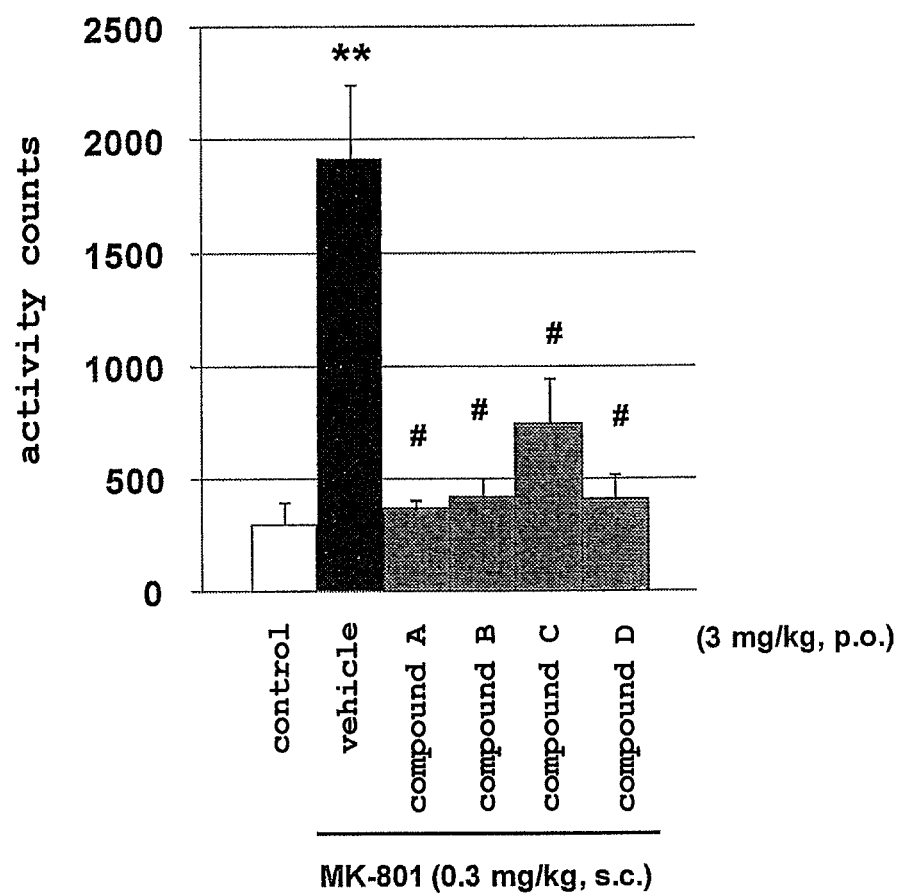

HETEROCYCLIC COMPOUND

This application is a U.S. national stage of International Application No. PCT/JP2011/067809 filed Aug. 3, 2011.

TECHNICAL FIELD

The present invention relates to a novel heterocyclic compound, a production method thereof and a medicament containing same and the like. More particularly, the present invention relates to a compound having an inhibitory action on phosphodiesterase 10A and effective as a prophylactic or therapeutic medicament for mental diseases such as schizophrenia and the like, and the like.

BACKGROUND OF THE INVENTION

Phosphodiesterase (PDE) is an enzyme that hydrolyzes cAMP and cGMP that function as intracellular second messengers into 5'-AMP and 5'-GMP, respectively. PDE gene is constituted with 21 genes, and currently classified into 11 kinds of families based on the molecular structure of the enzymes. Furthermore, each PDE is classified into the following 3 kinds: 1) cAMP-PDEs (PDE4, PDE7, PDE8), 2) cGMP-PDE (PDE5, PDE6, PDE9), and 3) dual-substrate PDEs (PDE1, PDE2, PDE3, PDE10, PDE11), based on the substrate specificity.

cAMP and cGMP are involved in the control of various physiological functions such as control of ion channel, muscle relaxation, learning and memory function, differentiation, apoptosis, lipogenesis, glycogenolysis and gluconeogenesis. Particularly, they are known to play an important role in the differentiation and survival, as well as control of neurotransmission of the nerve cell (non-patent document 1). Phosphorylation of various molecules that control physiological functions such as transcription factors, ion channel and receptor, which is caused by protein kinase A (PKA) and protein kinase G (PKG), contributes to such control by cAMP and cGMP, and the amounts of cAMP and cGMP in the cell are under spatiotemporal regulation via generation by adenylate cyclase and guanylate cyclase in response to extracellular stimulations and degradation thereof by PDE (non-patent document 2). Since PDE is a sole enzyme that decomposes cAMP and cGMP in vivo, PDE is considered to play an important role in the regulation of cyclic nucleotide signaling.

PDE10A is a molecule cloned and reported by 3 independent groups in 1999 (non-patent documents 3, 4). Expression analysis thereof has elucidated that PDE10A shows high expression only in the brain and testis, and has a localized expression pattern in the PDE family (non-patent documents 5, 6). In the brain, both PDE10A mRNA and PDE10A protein show high expression in medium spiny nerve cells of the striatum (medium spiny neurons, MSNs) (non-patent documents 7, 8). MSNs are classified as two major kinds of pathways. One of them is called a direct pathway or nigrostriatal pathway, and mainly expresses dopamine $D_1$ receptors. The other pathway, indirect pathway, is called a striatum-globus pallidus pathway, and mainly expresses dopamine $D_2$ receptors. The direct pathway is involved in the functions of motion execution and reward learning and, on the other hand, the indirect pathway is involved in the suppression of motility. The activity of the output nucleus of the basal nucleus is regulated by the balance of antagonistic inputs from these two kinds of pathways. Since PDE10A is expressed in MSNs of both pathways, the both pathways are considered to be activated by inhibition of PDE10A. Since the action of existing antipsychotic agents having a $D_2$ receptor shutting off action is mainly mediated by the activation of indirect pathway, a PDE10A inhibitor is expected to show an anti-mental disease action like existing drugs.

The excess $D_2$ receptor shutting off action in the brain by existing drugs causes side effects such as hyperprolactinemia and extrapyramidal syndrome. However, since PDE10A shows striatum pathway specific expression and shows a lower expression level in the pituitary gland mainly involved in the prolactin release, PDE10A inhibitor is considered to have no prolactin concentration increasing action in plasma. Moreover, since PDE10A is also expressed in the direct pathway MSNs and activated by a PDE10A inhibitor, it is considered to have superior characteristics than existing antipsychotic agents that activate only indirect pathways. That is, since the direct pathway is involved in the motion execution, it is considered to antagonistically act against extrapyramidal syndrome caused by excessive activation of indirect pathway. Furthermore, this pathway is expected to show actions to enhance the output from the striatum-thalamus circuit and promote cognitive functions of reward learning and problem solving. Since existing antipsychotic agents show a shutting off action on many receptors, they pose problems of side effects such as body weight increase and abnormal metabolism. PDE10A inhibitor is also considered to be superior to the existing drugs in the side effects, since it directly activates second messenger signaling without receptor blocking action of dopamine and/or other neurotransmitter. In view of the specific expression and its function in the brain nerve system, PDE10A is considered to be useful as a drug discovery target in neurological diseases, in particular, psychotic disorders such as schizophrenia.

Patent document 1 discloses a compound of the following formula:

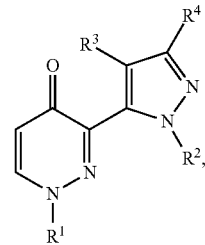

and the following compounds:

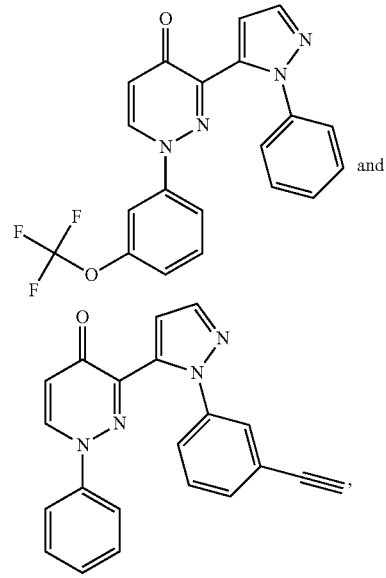

as a PDE10A inhibitor.

Patent document 2 discloses a compound of the following formula:
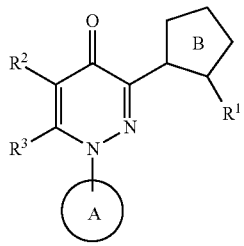
and the following compounds:
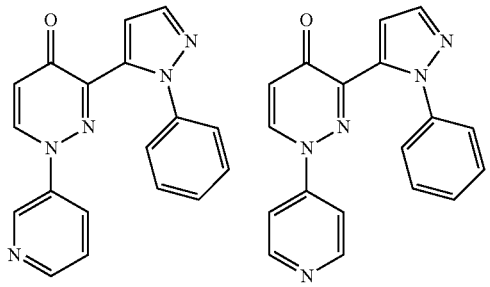
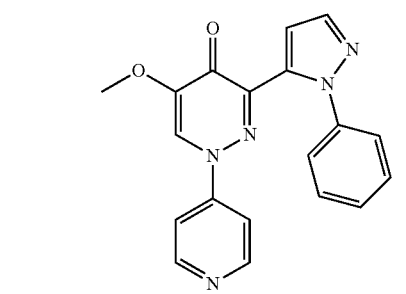
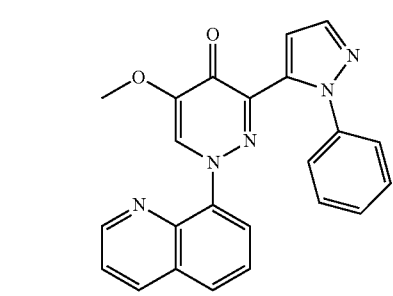
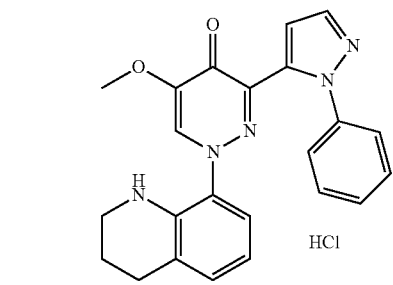
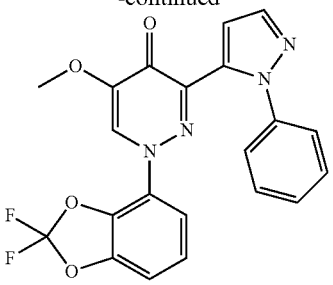
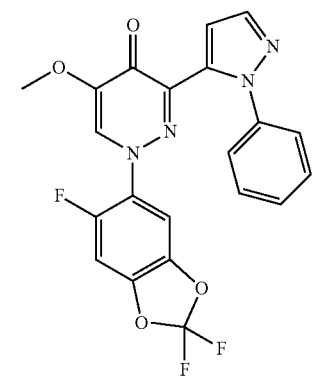
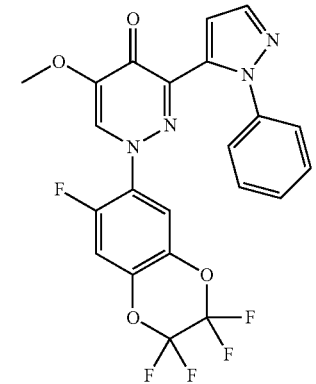
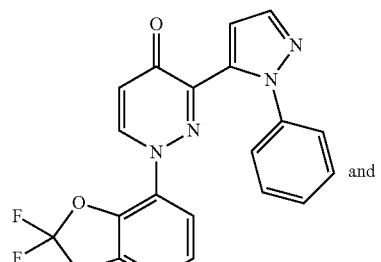
and
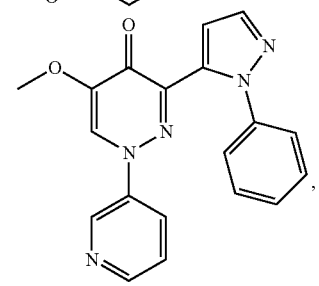
,
as a PDE10A inhibitor.

DOCUMENT LIST

Patent Documents

Patent Document 1: WO 2010/063610
Patent Document 2: WO 2010/090737

Non-Patent Documents

Non-Patent Document 1: Nat. Rev. Drug Disc. 2006, vol. 5: 660
Non-Patent Document 2: Circ. Res. 2007, vol. 100(7): 950-966
Non-Patent Document 3: Proc. Natl. Acad. Sci. USA 1999, vol. 96: 8991-8996
Non-Patent Document 4: J. Biol. Chem. 1999, vol. 274: 18438-18445, Gene 1999, vol. 234: 109-117
Non-Patent Document 5: Eur. J. Biochem. 1999, vol. 266: 1118-1127
Non-Patent Document 6: J. Biol. Chem. 1999, vol. 274: 18438-18445
Non-Patent Document 7: Eur. J. Biochem. 1999, vol. 266: 1118-1127
Non-Patent Document 8: Brain Res. 2003, vol. 985: 113-126

SUMMARY OF THE INVENTION

Problems to be Solved by the Invention

The present invention aims to provide a compound having a PDE10A inhibitory action and useful as a prophylactic or therapeutic drug for mental diseases such as schizophrenia and the like.

Means of Solving the Problems

The present inventors discovered that a compound represented by the formula (1) or a salt thereof (referred to as compound (1) in this specification) has a PDE10A inhibitory action and after extensive investigation, completed the present invention.

In this specification, the compound (1) or a prodrug thereof is also referred to the compound of the present invention.

Accordingly, the present invention provides
[1] a compound represented by the formula (1)

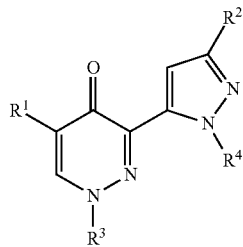

(1)

wherein
$R^1$ is an optionally substituted $C_{1-6}$ alkoxy group,
$R^2$ is a hydrogen atom or an optionally substituted $C_{1-6}$ alkyl group,
$R^3$ is

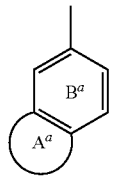

wherein
ring $A^a$ is an optionally substituted 5- or 6-membered heterocycle wherein the substituents for ring $A^a$ are optionally bonded to form a ring; and
ring $B^a$ is an optionally substituted benzene ring or an optionally substituted pyridine ring, or

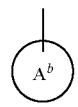

wherein
ring $A^b$ is a substituted pyridine ring, an optionally substituted pyrazole ring, an optionally substituted thiazole ring, an optionally substituted pyrazine ring, an optionally substituted pyridazine ring, an optionally substituted pyrimidine ring or an optionally substituted imidazole ring, and
$R^4$ is an optionally substituted $C_{1-6}$ alkyl group or an optionally substituted phenyl group,
provided that the following compound:
a compound wherein $R^1$ is a $C_{1-6}$ alkoxy group substituted by substituent(s) having optionally substituted cyclic group(s),
5-methoxy-3-(1-phenyl-1H-pyrazol-5-yl)-1-(2,2,6-trifluoro-1,3-benzodioxol-5-yl)pyridazin-4(1H)-one, and
5-methoxy-1-(2,2,3,3,7-pentafluoro-2,3-dihydro-1,4-benzodioxin-6-yl)-3-(1-phenyl-1H-pyrazol-5-yl)pyridazin-4(1H)-one
are excluded,
or a salt thereof;
[2] the compound or salt of the above-mentioned [1], wherein $R^3$ is

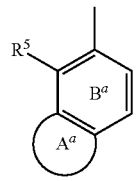

wherein
$R^5$ is a substituent, and
the other symbols are defined as in the above-mentioned [1];
[3] the compound or salt of the above-mentioned [2], wherein $R^5$ is a halogen atom or an optionally substituted $C_{1-6}$ alkoxy group;

[4] the compound or salt of the above-mentioned [1], wherein R³ is

wherein ring $A^b$ is a substituted pyridine ring or a substituted pyrazole ring;
[5] 5-{3-[1-(3-chlorophenyl)-1H-pyrazol-5-yl]-5-methoxy-4-oxopyridazin-1(4H)-yl}-4-fluoro-1,3,3-trimethyl-1,3-dihydro-2H-indol-2-one or a salt thereof;
[6] 1-(cyclopropylmethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one or a salt thereof;
[7] 1-[1-(1-cyclopropylethyl)-1H-pyrazol-4-yl]-5-methoxy-3-(1-phenyl-1H-pyrazol-5-yl)pyridazin-4(1H)-one or a salt thereof;
[8] 5-methoxy-1-[2-methoxy-6-(3,3,4,4-tetrafluoropyrrolidin-1-yl)pyridin-3-yl]-3-(1-phenyl-1H-pyrazol-5-yl)pyridazin-4(1H)-one or a salt thereof;
[9] 1-[6-(3,4-difluoro-1H-pyrrol-1-yl)-2-methoxypyridin-3-yl]-5-methoxy-3-(1-phenyl-1H-pyrazol-5-yl)pyridazin-4(1H)-one or a salt thereof;
[10] a medicament comprising the compound or salt of the above-mentioned [1];
[11] the medicament of the above-mentioned [10], which is a phosphodiesterase 10A inhibitor;
[12] the medicament of the above-mentioned [10], which is for preventing or treating schizophrenia;
[13] a method for preventing or treating schizophrenia which comprises administering an effective amount of the compound or salt of the above-mentioned [1] to mammal;
[14] use of the compound or salt of the above-mentioned [1] in the manufacture of a medicament for preventing or treating schizophrenia;
[15] the compound or salt of the above-mentioned [1] for preventing or treating schizophrenia; and the like.

Effect of the Invention

The compound of the present invention has a PDE 10A inhibitory action and is useful as a prophylactic or therapeutic medicament for schizophrenia, etc.

BRIEF DESCRIPTION OF THE DRAWINGS

FIG. 1 is a graph showing the suppressive action of the compound on an MK-801-induced locomotor hyperactivity in mouse (Experimental Example 2).

DETAILED DESCRIPTION OF THE INVENTION

The present invention is explained in detail below.
Unless otherwise specified, in this specification, examples of the "halogen atom" include fluorine, chlorine, bromine and iodine.
Unless otherwise specified, in this specification, the phrase "optionally halogenated" or the term "halogeno" means that one or more (e.g., 1 to 5) halogen atoms can be present as substituents.
Unless otherwise specified, in this specification, examples of the "alkyl (group)" include $C_{1-6}$ alkyl (group).
Unless otherwise specified, in this specification, examples of the "$C_{1-6}$ alkyl (group)" include methyl, ethyl, propyl, isopropyl, butyl, isobutyl, sec sec-butyl, tert-butyl, pentyl, isopentyl, neopentyl and hexyl.
Unless otherwise specified, in this specification, the term "optionally halogenated $C_{1-6}$ alkyl (group)" means $C_{1-6}$ alkyl (group) which can be substituted by halogen atom(s), and examples thereof include trifluoromethyl, difluoromethyl, 2,2-difluoroethyl, 2,2,2-trifluoroethyl and 2,2,3,3,3-pentafluoropropyl.
Unless otherwise specified, in this specification, examples of the "alkenyl (group)" include $C_{2-6}$ alkenyl (group).
Unless otherwise specified, in this specification, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl.
Unless otherwise specified, in this specification, examples of the "alkynyl (group)" include $C_{2-6}$ alkynyl (group). Examples of the "$C_{2-6}$ alkynyl (group)" include ethynyl, 1-propyn-1-yl, 2-propyn-1-yl, 4-pentyn-1-yl and 5-hexyn-1-yl.
Unless otherwise specified, in this specification, examples of the "$C_{3-7}$ cycloalkyl-$C_{2-6}$ alkynyl (group)" include cyclopropylethynyl.
Unless otherwise specified, in this specification, examples of the "$C_{3-7}$ cycloalkyl (group)" include cyclopropyl, cyclobutyl, cyclopentyl and cyclohexyl.
Unless otherwise specified, in this specification, examples of the "$C_{6-14}$ aryl (group)" include phenyl, 1-naphthyl, 2-naphthyl, 2-biphenylyl, 3-biphenylyl, 4-biphenylyl and 2-anthryl.
Unless otherwise specified, in this specification, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl and 4-biphenylylmethyl.
Unless otherwise specified, in this specification, examples of the "$C_{6-14}$ aryl-$C_{2-6}$ alkenyl (group)" include styryl.
Unless otherwise specified, in this specification, examples of the "carbocycle having 5 to 6 carbon atoms" include a $C_{5-6}$ cycloalkane (e.g., cyclopentane, cyclohexane), a $C_{5-6}$ cycloalkene (e.g., cyclopentene, cyclohexene), a $C_{5-6}$ cycloalkadiene (e.g., cyclopentadiene, cyclohexadiene) and a benzene ring.
Unless otherwise specified, in this specification, examples of the "$C_{3-6}$ cycloalkane" include cyclopropane, cyclobutane, cyclopentane and cyclohexane.
Unless otherwise specified, in this specification, examples of the "5- or 6-membered heterocycle" include a 5- or 6-membered heterocycle containing, besides carbon atoms, 1 to 4 hetero atoms selected from a nitrogen atom, a sulfur atom and an oxygen atom.
Unless otherwise specified, in this specification, examples of the "5- or 6-membered heterocycle containing, besides carbon atoms, 1 to 4 hetero atoms selected from a nitrogen atom, a sulfur atom and an oxygen atom" include a pyrrolidine ring, a tetrahydrofuran ring, a tetrahydrothiophene ring, a piperidine ring, a tetrahydropyran ring, a morpholine ring, a thiomorpholine ring, a piperazine ring, a furan ring, a thiophene ring, a pyrrole ring, an oxazole ring, an isoxazole ring, a thiazole ring, an isothiazole ring, an imidazole ring, a pyrroline ring (e.g., 1-pyrroline ring, 2-pyrroline ring, 3-pyrroline ring), a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring and a triazine ring.

Unless otherwise specified, in this specification, the "heterocyclic group" (and the heterocyclic moiety in a substituent) is a non-aromatic heterocyclic group or a heteroaryl group (i.e., an aromatic heterocyclic group), and examples thereof include a 3- to 14-membered heterocyclic group having 1 to 5 hetero atoms selected from a nitrogen atom, a sulfur atom and an oxygen atom. The "heterocyclic group" can be monocyclic, bicyclic or tricyclic.

Unless otherwise specified, in this specification, examples of the "3- to 14-membered heterocyclic group" include a 3- to 14-membered aromatic heterocyclic group having 1 to 5 hetero atoms selected from a nitrogen atom, a sulfur atom and an oxygen atom such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl, 6-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl and imidazo[1,2-a]pyridin-8-yl) and the like; and a saturated or unsaturated 3- to 14-membered non-aromatic heterocyclic group having 1 to 5 hetero atoms selected from a nitrogen atom, a sulfur atom and an oxygen atom such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroindolyl (e.g., dihydroindol-5-yl), dihydroquinolyl and the like.

Unless otherwise specified, in this specification, examples of the "aromatic heterocyclic group" (and the aromatic heterocyclic moiety in a substituent) include the "3- to 14-membered aromatic heterocyclic group having 1 to 5 hetero atoms selected from a nitrogen atom, a sulfur atom and an oxygen atom" as exemplified above as the above-mentioned "heterocyclic group".

Unless otherwise specified, in this specification, examples of the "non-aromatic heterocyclic group" (and the aromatic heterocyclic moiety in a substituent) include the "saturated or unsaturated 3- to 14-membered non-aromatic heterocyclic group having 1 to 5 hetero atoms selected from a nitrogen atom, a sulfur atom and an oxygen atom" as exemplified above as the above-mentioned "heterocyclic group".

Unless otherwise specified, in this specification, examples of the "saturated heterocyclic group" (and the saturated heterocyclic moiety in a substituent) include those saturated group, from among the above-mentioned "non-aromatic heterocyclic group". Specific examples thereof include tetrahydrofuryl, morpholinyl, thiomorpholinyl, piperidinyl, pyrrolidinyl, piperazinyl and the like.

Unless otherwise specified, in this specification, examples of the "5- to 6-membered saturated heterocyclic group" (and the saturated heterocyclic moiety in a substituent) include those having 5- to 6-membered group, from among the above-mentioned "saturated heterocyclic group".

Unless otherwise specified, in this specification, examples of the "alkoxy (group)" include $C_{1-6}$ alkoxy (group).

Unless otherwise specified, in this specification, examples of the "$C_{1-6}$ alkoxy (group)" include methoxy, ethoxy, propoxy, isopropoxy, butoxy, isobutoxy, sec-butoxy, pentyloxy and hexyloxy.

Unless otherwise specified, in this specification, examples of the "$C_{3-7}$ cycloalkyloxy (group)" include cyclopropyloxy, cyclobutyloxy, cyclopentyloxy and cyclohexyloxy.

Unless otherwise specified, in this specification, examples of the "$C_{6-14}$ aryloxy (group)" include phenyloxy, 1-naphthyloxy and 2-naphthyloxy.

Unless otherwise specified, in this specification, examples of the "$C_{7-16}$ aralkyloxy (group)" include benzyloxy and phenethyloxy.

Unless otherwise specified, in this specification, examples of the "alkyl-carbonyloxy (group)" include $C_{1-6}$ alkyl-carbonyloxy (group).

Unless otherwise specified, in this specification, examples of the "$C_{1-6}$ alkyl-carbonyloxy (group)" include acetoxy and propionyloxy.

Unless otherwise specified, in this specification, examples of the "alkoxy-carbonyloxy (group)" include $C_{1-6}$ alkoxy-carbonyloxy (group).

Unless otherwise specified, in this specification, examples of the "$C_{1-6}$ alkoxy-carbonyloxy (group)" include methoxycarbonyloxy, ethoxycarbonyloxy, propoxycarbonyloxy and butoxycarbonyloxy.

Unless otherwise specified, in this specification, examples of the "mono-alkyl-carbamoyloxy (group)" include mono-$C_{1-6}$ alkyl-carbamoyloxy (group).

Unless otherwise specified, in this specification, examples of the "mono-$C_{1-6}$ alkyl-carbamoyloxy (group)" include methylcarbamoyloxy and ethylcarbamoyloxy.

Unless otherwise specified, in this specification, examples of the "di-alkyl-carbamoyloxy (group)" include di-$C_{1-6}$ alkyl-carbamoyloxy (group).

Unless otherwise specified, in this specification, examples of the "di-$C_{1-6}$ alkyl-carbamoyloxy (group)" include dimethylcarbamoyloxy and diethylcarbamoyloxy.

Unless otherwise specified, in this specification, examples of the "$C_{6-14}$ aryl-carbonyloxy (group)" include benzoyloxy and naphthylcarbonyloxy.

Unless otherwise specified, in this specification, examples of the "mono- or di-$C_{6-14}$ aryl-carbamoyloxy (group)" include phenylcarbamoyloxy and naphthylcarbamoyloxy.

Unless otherwise specified, in this specification, examples of the heterocyclic moiety of the "heterocyclyl-oxy (group)" include those similar to the above-mentioned "heterocyclic group". Specific examples of the "heterocyclyl-oxy (group)" include 5- to 14-membered heterocyclyl-oxy (group) having 1 to 5 hetero atoms selected from a nitrogen atom, a sulfur atom and an oxygen atom.

Unless otherwise specified, in this specification, examples of the aromatic heterocyclic moiety of the "aromatic heterocyclyl-oxy (group)" include those similar to the "aromatic heterocyclic group" as examples of the above-mentioned "heterocyclic group". Specific examples of the "aromatic heterocyclyl-oxy (group)" include 3- to 14-membered aromatic heterocyclyl-oxy (group) having 1 to 5 hetero atoms selected from a nitrogen atom, a sulfur atom and an oxygen atom.

Unless otherwise specified, in this specification, examples of the "$C_{1-6}$ alkylsulfonyloxy (group)" include methylsulfonyloxy and ethylsulfonyloxy.

Unless otherwise specified, in this specification, examples of the "halogeno $C_{1-6}$ alkylsulfonyloxy (group)" include halogenomethylsulfonyloxy and halogenoethylsulfonyloxy.

Unless otherwise specified, in this specification, examples of the "alkylsulfanyl (group)" include $C_{1-6}$ alkylsulfanyl (group).

Unless otherwise specified, in this specification, examples of the "$C_{1-6}$ alkylsulfanyl (group)" include methylsulfanyl, ethylsulfanyl, propylsulfanyl, isopropylsulfanyl, butylsulfanyl, sec-butylsulfanyl and tert-butylsulfanyl.

Unless otherwise specified, in this specification, examples of the "$C_{3-7}$ cycloalkylsulfanyl (group)" include cyclopropylsulfanyl, cyclobutylsulfanyl, cyclopentylsulfanyl and cyclohexylsulfanyl.

Unless otherwise specified, in this specification, examples of the "$C_{6-14}$ arylsulfanyl (group)" include phenylsulfanyl, 1-naphthylsulfanyl and 2-naphthylsulfanyl.

Unless otherwise specified, in this specification, examples of the "$C_{7-16}$ aralkylsulfanyl (group)" include benzylsufanyl and phenethylsulfanyl.

Unless otherwise specified, in this specification, examples of the heterocyclic moiety of the "heterocyclyl-sulfanyl (group)" include those similar to the above-mentioned "heterocyclic group". Specific examples of the "heterocyclyl-sulfanyl (group)" include 5- to 14-membered heterocyclyl-sulfanyl (group) having 1 to 5 hetero atoms selected from a nitrogen atom, a sulfur atom and an oxygen atom.

Unless otherwise specified, in this specification, examples of the "alkyl-carbonyl (group)" include $C_{1-6}$ alkyl-carbonyl (group).

Unless otherwise specified, in this specification, examples of the "$C_{1-6}$ alkyl-carbonyl (group)" include acetyl, propionyl and pivaloyl.

Unless otherwise specified, in this specification, examples of the "$C_{3-7}$ cycloalkyl-carbonyl (group)" include cyclopropylcarbonyl, cyclopentylcarbonyl and cyclohexylcarbonyl.

Unless otherwise specified, in this specification, examples of the "$C_{6-14}$ aryl-carbonyl (group)" include benzoyl, 1-naphthoyl and 2-naphthoyl.

Unless otherwise specified, in this specification, examples of the "$C_{7-16}$ aralkyl-carbonyl (group)" include phenylacetyl and 3-phenylpropionyl.

Unless otherwise specified, in this specification, examples of the heterocyclic moiety of the "heterocyclyl-carbonyl (group)" include those similar to the above-mentioned "heterocyclic group". Specific examples thereof include 3- to 14-membered heterocyclyl-carbonyl (group) having 1 to 5 hetero atoms selected from a nitrogen atom, a sulfur atom and an oxygen atom. More specific examples thereof include picolinoyl, nicotinoyl, isonicotinoyl, 2-thenoyl, 3-thenoyl, 2-furoyl, 3-furoyl, 4-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

Unless otherwise specified, in this specification, examples of the "optionally esterified carboxy (group)" include carboxy, optionally substituted alkoxy-carbonyl (group), optionally substituted $C_{6-14}$ aryloxy-carbonyl (group), optionally substituted $C_{7-16}$ aralkyloxy-carbonyl (group), optionally substituted silyloxy-carbonyl (group) (e.g., TMS-O—CO—, TES-O—CO—, TBS-O—CO—, TIPS-O—CO—, TBDPS-O—CO—) and the like.

Unless otherwise specified, in this specification, examples of the "alkoxy-carbonyl (group)" include "$C_{1-6}$ alkoxy-carbonyl (group)".

Unless otherwise specified, in this specification, examples of the "$C_{1-6}$ alkoxy-carbonyl (group)" include methoxycarbonyl, ethoxycarbonyl, propoxycarbonyl and tert-butoxycarbonyl.

Unless otherwise specified, in this specification, examples of the "$C_{6-14}$ aryloxy-carbonyl (group)" include phenoxycarbonyl.

Unless otherwise specified, in this specification, examples of the "$C_{7-16}$ aralkyloxy-carbonyl (group)" include benzyloxycarbonyl and phenethyloxycarbonyl.

Unless otherwise specified, in this specification, examples of the "alkylsulfonyl (group)" include $C_{1-6}$ alkylsulfonyl (group).

Unless otherwise specified, in this specification, examples of the "$C_{1-6}$ alkylsulfonyl (group)" include methylsulfonyl and ethylsulfonyl.

Unless otherwise specified, in this specification, examples of the "$C_{3-7}$ cycloalkylsulfonyl (group)" include cyclopropylsulfonyl, cyclobutylsulfonyl, cyclopentylsulfonyl and cyclohexylsulfonyl.

Unless otherwise specified, in this specification, examples of the "$C_{6-14}$ arylsulfonyl (group)" include phenylsulfonyl, 1-naphthylsulfonyl and 2-naphthylsulfonyl.

Unless otherwise specified, in this specification, examples of the heterocyclic moiety of the "heterocyclyl-sulfonyl (group)" include those similar to the above-mentioned "heterocyclic group". Specific examples of the "heterocyclylsulfonyl (group)" include 5- to 14-membered heterocyclylsulfonyl (group) having 1 to 5 hetero atoms selected from a nitrogen atom, a sulfur atom and an oxygen atom.

Unless otherwise specified, in this specification, examples of the "alkylsulfinyl (group)" include $C_{1-6}$ alkylsulfinyl (group).

Unless otherwise specified, in this specification, examples of the "$C_{1-6}$ alkylsulfinyl (group)" include methylsulfinyl and ethylsulfinyl.

Unless otherwise specified, in this specification, examples of the "$C_{3-7}$ cycloalkylsulfinyl (group)" include cyclopropylsulfinyl, cyclobutylsulfinyl, cyclopentylsufinyl and cyclohexysulfinyl.

Unless otherwise specified, in this specification, examples of the "$C_{6-14}$ arylsulfinyl (group)" include phenylsulfinyl, 1-naphthylsulfinyl and 2-naphthylsulfinyl.

Unless otherwise specified, in this specification, examples of the heterocyclic moiety of the "heterocyclyl-sulfinyl (group)" include those similar to the above-mentioned "heterocyclic group". Specific examples of the "heterocyclylsulfinyl (group)" include 5- to 14-membered heterocyclylsulfinyl (group) having. 1 to 5 hetero atoms selected from a nitrogen atom, a sulfur atom and an oxygen atom.

Unless otherwise specified, in this specification, examples of the "optionally substituted carbamoyl (group)" include carbamoyl (group), optionally substituted mono- or di-alkyl-carbamoyl (group).

Unless otherwise specified, in this specification, examples of the "alkyl-carbamoyl (group)" include mono- or di-$C_{1-6}$ alkyl-carbamoyl (group).

Unless otherwise specified, in this specification, examples of the "mono- or di-$C_{1-6}$ alkyl-carbamoyl (group)" include methylcarbamoyl, ethylcarbamoyl, propylcarbamoyl, dimethylcarbamoyl, diethylcarbamoyl and ethylmethylcarbamoyl.

Unless otherwise specified, in this specification, examples of the "mono- or di-alkylamino (group)" include mono- or di-$C_{1-6}$ alkylamino (group)".

Unless otherwise specified, in this specification, examples of the "mono- or di-$C_{1-6}$ alkylamino (group)" include methylamino, ethylamino, propylamino, dimethylamino and diethylamino.

Unless otherwise specified, in this specification, examples of the "alkyl-carbonylamino (group)" include $C_{1-6}$ alkyl-carbonylamino (group).

Unless otherwise specified, in this specification, examples of the "$C_{1-6}$ alkyl-carbonylamino (group)" include acetylamino, propionylamino and pivaloylamino.

Unless otherwise specified, in this specification, as the heterocyclic moiety of the "heterocyclyl-amino (group)", for example, those similar to the above-mentioned "heterocyclic group" can be used. Examples of the "heterocyclyl-amino (group)" include 2-pyridyl-amino.

Unless otherwise specified, in this specification, as the heterocyclic moiety of the "heterocyclyl-carbonylamino (group)", those similar to the above-mentioned "heterocyclyl-carbonyl" can be used. Examples of the "heterocyclyl-carbonylamino (group)" include 2-pyridyl-carbonylamino.

Unless otherwise specified, in this specification, as the heterocyclic moiety of the "heterocyclyl-oxycarbonylamino (group)", those similar to the above-mentioned "heterocyclic group" can be used. Examples of the "heterocyclyl-oxycarbonylamino (group)" include 2-pyridyl-oxycarbonylamino.

Unless otherwise specified, in this specification, as the heterocyclic moiety of the "heterocyclyl-sulfonylamino (group)", for example, those similar to the above-mentioned "heterocyclic group" can be used. Examples of the "heterocyclyl-sulfonylamino (group)" include 2-pyridyl-sulfonylamino.

Unless otherwise specified, in this specification, examples of the "alkoxy-carbonylamino (group)" include $C_{1-6}$ alkoxy-carbonylamino (group).

Unless otherwise specified, in this specification, the "$C_{1-6}$ alkoxy-carbonylamino (group)" include methoxycarbonylamino, ethoxycarbonylamino, propoxycarbonylamino and butoxycarbonylamino.

Unless otherwise specified, in this specification, examples of the "alkylsulfonylamino (group)" include $C_{1-6}$ alkylsulfonylamino (group).

Unless otherwise specified, in this specification, examples of the "$C_{1-6}$ alkylsulfonylamino (group)" include methylsulfonylamino and ethylsulfonylamino.

Unless otherwise specified, in this specification, examples of the "mono- or di-$C_{3-7}$ cycloalkylamino (group)" include cyclopropylamino, cyclopentylamino and cyclohexylamino.

Unless otherwise specified, in this specification, examples of the "$C_{3-7}$ cycloalkyl-carbonylamino (group)" include cyclopropylcarbonylamino, cyclopentylcarbonylamino and cyclohexylcarbonylamino.

Unless otherwise specified, in this specification, examples of the "$C_{3-7}$ cycloalkyloxy-carbonylamino (group)" include cyclopropoxycarbonylamino, cyclopentyloxycarbonylamino and cyclohexyloxycarbonylamino.

Unless otherwise specified, in this specification, examples of the "$C_{3-7}$ cycloalkylsulfonylamino (group)" include cyclopropylsulfonylamino, cyclopentylsulfonylamino and cyclohexylsulfonylamino.

Unless otherwise specified, in this specification, examples of the "mono- or di-$C_{6-14}$ arylamino (group)" include phenylamino and diphenylamino.

Unless otherwise specified, in this specification, examples of the "mono- or di-$C_{7-16}$ aralkylamino (group)" include benzylamino.

Unless otherwise specified, in this specification, examples of the "$C_{6-14}$ aryl-carbonylamino (group)" include benzoylamino and naphthoylamino.

Unless otherwise specified, in this specification, examples of the "$C_{6-14}$ arylsulfonylamino (group)" include phenylsulfonylamino, 2-naphthylsulfonylamino and 1-naphthylsulfonylamino.

Unless otherwise specified, in this specification, examples of the "optionally substituted carbamoylamino (group)" include carbamoylamino (group), optionally substituted mono- or di-alkyl-carbamoylamino (group).

Unless otherwise specified, in this specification, examples of the "mono- or di-alkyl-carbamoylamino (group)" include mono- or di-$C_{1-6}$ alkyl-carbamoylamino (group).

Unless otherwise specified, in this specification, examples of the "mono- or di-$C_{1-6}$ alkyl-carbamoylamino (group)" include methylcarbamoylamino, ethylcarbamoylamino, propylcarbamoylamino, dimethylcarbamoylamino, diethylcarbamoylamino and ethylmethylcarbamoylamino.

[Substituent Group A]

In the present specification, Substituent Group A consists of (1) a halogen atom;
(2) a nitro group;
(3) a cyano group;
(4) an optionally esterified carboxy group;
[e.g., a carboxy group,
an optionally substituted alkoxy-carbonyl group,
an optionally substituted $C_{6-14}$ aryloxy-carbonyl group,
an optionally substituted $C_{7-16}$ aralkyloxy-carbonyl group,
an optionally substituted silyloxy-carbonyl group and the like];
(5) an optionally substituted alkyl group;
(6) an optionally substituted alkenyl group;
(7) an optionally substituted alkynyl group
(8) an optionally substituted $C_{3-7}$ cycloalkyl-$C_{2-6}$ alkynyl group;
(9) an optionally substituted $C_{3-7}$ cycloalkyl group;
(10) an optionally substituted $C_{6-14}$ aryl group;
(11) an optionally substituted $C_{7-16}$ aralkyl group;
(12) an optionally substituted $C_{6-14}$ aryl-$C_{2-6}$ alkenyl group;
(13) an optionally substituted heterocyclic group;
(14) a hydroxy group;
(15) an optionally substituted alkoxy group;
(16) an optionally substituted $C_{3-7}$ cycloalkyloxy group;
(17) an optionally substituted $C_{6-14}$ aryloxy group;
(18) an optionally substituted $C_{7-16}$ aralkyloxy group;
(19) an optionally substituted alkyl-carbonyloxy group;
(20) an optionally substituted alkoxy-carbonyloxy group;
(21) an optionally substituted mono-alkyl-carbamoyloxy group;
(22) an optionally substituted di-alkyl-carbamoyloxy group;
(23) an optionally substituted $C_{6-14}$ aryl-carbonyloxy group;
(24) an optionally substituted mono- or di-$C_{6-14}$ aryl-carbamoyloxy group;
(25) an optionally substituted heterocyclyl-oxy group (e.g., an optionally substituted aromatic heterocyclyl-oxy group);
(26) an optionally substituted $C_{1-6}$ alkylsulfonyloxy group (e.g., an optionally substituted halogeno $C_{1-6}$ alkylsulfonyloxy group),
(27) a mercapto group;
(28) an optionally substituted alkylsulfanyl group;
(29) an optionally substituted $C_{3-7}$ cycloalkylsulfanyl group;
(30) an optionally substituted $C_{6-14}$ arylsulfanyl group;
(31) an optionally substituted $C_{7-16}$ aralkylsulfanyl group;
(32) an optionally substituted heterocyclyl-sulfanyl group;
(33) a formyl group;
(34) an optionally substituted alkyl-carbonyl group;
(35) an optionally substituted $C_{3-7}$ cycloalkyl-carbonyl group;
(36) an optionally substituted $C_{6-14}$ aryl-carbonyl group;
(37) an optionally substituted $C_{7-16}$ aralkyl-carbonyl group;
(38) an optionally substituted heterocyclyl-carbonyl group;
(39) an optionally substituted alkylsulfonyl group;
(40) an optionally substituted $C_{3-7}$ cycloalkylsulfonyl group;
(41) an optionally substituted $C_{6-14}$ arylsulfonyl group;
(42) an optionally substituted heterocyclyl-sulfonyl group;
(43) an optionally substituted alkylsulfinyl group;
(44) an optionally substituted $C_{3-7}$ cycloalkylsulfinyl group;
(45) an optionally substituted $C_{6-14}$ arylsulfinyl group;
(46) an optionally substituted heterocyclyl-sulfinyl group;
(47) a sulfo group;
(48) a sulfamoyl group;
(49) a sulfinamoyl group;
(50) a sulfenamoyl group;
(51) a thiocarbamoyl group;
(52) an optionally substituted carbamoyl group [e.g., a carbamoyl group, an optionally substituted mono- or di-alkyl-carbamoyl group and the like];
(53) an optionally substituted amino group
[e.g.,
an amino group,
an optionally substituted mono- or di-alkylamino group,
an optionally substituted mono- or di-$C_{3-7}$ cycloalkylamino group,
an optionally substituted mono- or di-$C_{6-14}$ arylamino group,
an optionally substituted mono- or di-$C_{7-16}$ aralkylamino group,
an optionally substituted heterocyclyl-amino group,
an optionally substituted $C_{6-14}$ aryl-carbonylamino group,
a formylamino group,
an optionally substituted alkyl-carbonylamino group (e.g., an optionally substituted mono-($C_{1-6}$ alkyl-carbonyl)-amino group),
an optionally substituted $C_{3-7}$ cycloalkyl-carbonylamino group,
an optionally substituted heterocyclyl-carbonylamino group,
an optionally substituted alkoxy-carbonylamino group,
an optionally substituted $C_{3-7}$ cycloalkyloxy-carbonylamino group,
an optionally substituted heterocyclyl-oxycarbonylamino group,
an optionally substituted carbamoylamino group [e.g., a carbamoylamino group, an optionally substituted mono- or di-$C_{1-6}$ alkyl-carbamoylamino group and the like],
an optionally substituted alkylsulfonylamino group,
an optionally substituted $C_{3-7}$ cycloalkylsulfonylamino group,
an optionally substituted heterocyclyl-sulfonylamino group,
an optionally substituted $C_{6-14}$ arylsulfonylamino group];
(54) an oxo group; and
(55) an oxido group.

The number of the substituents is preferably 0 (i.e., unsubstituted) or 1 to 5. It is more preferably 0 (i.e., unsubstituted).

Examples of the substituent of the
"optionally substituted alkoxy-carbonyl group",
"optionally substituted alkyl group",
"optionally substituted alkenyl group",
"optionally substituted alkynyl group",
"optionally substituted alkoxy group",
"optionally substituted alkyl-carbonyloxy group",
"optionally substituted alkoxy-carbonyloxy group",
"optionally substituted mono-alkyl-carbamoyloxy group",
"optionally substituted di-alkyl-carbamoyloxy group",
"optionally substituted $C_{1-6}$ alkylsulfonyloxy group",
"optionally substituted halogeno $C_{1-6}$ alkylsulfonyloxy group",
"optionally substituted alkylsulfanyl group",
"optionally substituted alkyl-carbonyl group",
"optionally substituted alkylsulfonyl group",
"optionally substituted alkylsulfinyl group",
"optionally substituted mono- or di-alkyl-carbamoyl group",
"optionally substituted mono- or di-alkylamino group",
"optionally substituted alkyl-carbonylamino group",
"optionally substituted mono- or di-$C_{1-6}$ alkyl-carbamoylamino group",
"optionally substituted mono-($C_{1-6}$ alkyl-carbonyl)-amino group", "optionally substituted alkoxy-carbonylamino group",
"optionally substituted alkylsulfonylamino group", and
"optionally substituted silyloxy-carbonyl group" of the Substituent Group A include those selected from the following Substituent Group B.

Examples of the substituent of the
"optionally substituted $C_{6-14}$ aryloxy-carbonyl group",
"optionally substituted $C_{7-16}$ aralkyloxy-carbonyl group",
"optionally substituted $C_{3-7}$ cycloalkyl-$C_{2-6}$ alkynyl group",
"optionally substituted $C_{3-7}$ cycloalkyl group",
"optionally substituted $C_{6-14}$ aryl group",
"optionally substituted $C_{7-16}$ aralkyl group",
"optionally substituted $C_{6-14}$ aryl-$C_{2-6}$ alkenyl group",
"optionally substituted heterocyclic group",
"optionally substituted $C_{3-7}$ cycloalkyloxy group",
"optionally substituted $C_{6-14}$ aryloxy group",
"optionally substituted $C_{7-16}$ aralkyloxy group",
"optionally substituted $C_{6-14}$ aryl-carbonyloxy group",
"optionally substituted mono- or di-$C_{6-14}$ aryl-carbamoyloxy group",
"optionally substituted heterocyclyl-oxy group",
"optionally substituted aromatic heterocyclyl-oxy group",
"optionally substituted $C_{3-7}$ cycloalkylsulfanyl group",
"optionally substituted $C_{6-14}$ arylsulfanyl group",
"optionally substituted $C_{7-16}$ aralkylsulfanyl group",
"optionally substituted heterocyclyl-sulfanyl group",
"optionally substituted $C_{3-7}$ cycloalkyl-carbonyl group",
"optionally substituted $C_{6-14}$ aryl-carbonyl group",
"optionally substituted $C_{7-16}$ aralkyl-carbonyl group",
"optionally substituted heterocyclyl-carbonyl group",
"optionally substituted $C_{3-7}$ cycloalkylsulfonyl group",
"optionally substituted $C_{6-14}$ arylsulfonyl group",
"optionally substituted heterocyclyl-sulfonyl group",
"optionally substituted $C_{3-7}$ cycloalkylsulfinyl group",
"optionally substituted $C_{6-14}$ arylsulfinyl group",
"optionally substituted heterocyclyl-sulfinyl group",
"optionally substituted mono- or di-$C_{3-8}$ cycloalkylamino group",
"optionally substituted mono- or di-$C_{6-14}$ arylamino group",
"optionally substituted mono- or di-$C_{7-16}$ aralkylamino group",
"optionally substituted heterocyclyl-amino group",
"optionally substituted $C_{6-14}$ aryl-carbonylamino group",
"optionally substituted $C_{3-7}$ cycloalkyl-carbonylamino group",
"optionally substituted heterocyclyl-carbonylamino group",
"optionally substituted $C_{3-7}$ cycloalkyloxy-carbonylamino group",
"optionally substituted heterocyclyl-oxycarbonylamino group",
"optionally substituted $C_{3-7}$ cycloalkylsulfonylamino group",
"optionally substituted heterocyclyl-sulfonylamino group", and
"optionally substituted $C_{6-14}$ arylsulfonylamino group" of the Substituent Group A include those selected from the following Substituent Group B and the following Substituent Group B'. The number of the substituents is 1-substitutable maximum number, more preferably 1-3, further preferably 1.

In the present specification, Substituent Group B consists of
(a) a halogen atom;
(b) a hydroxy group;
(c) a nitro group;
(d) a cyano group;
(e) an optionally substituted $C_{6-14}$ aryl group (the $C_{6-14}$ aryl group is optionally substituted by substituent(s) such as a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);
(f) an optionally substituted $C_{6-14}$ aryloxy group (the $C_{6-14}$ aryloxy group is optionally substituted by substituent(s) such as a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);
(g) an optionally substituted $C_{7-16}$ aralkyloxy group (the $C_{7-16}$ aralkyloxy group is optionally substituted by substituent(s) such as a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);
(h) an optionally substituted 5- to 10-membered heterocyclic group having 1 to 4 hetero atoms selected from a nitrogen atom, a sulfur atom and an oxygen atom (e.g., furyl, pyridyl, thienyl, pyrrolidino, 1-piperidinyl, 4-piperidyl, piperazinyl, 4-morpholinyl, 4-thiomorpholinyl, azepan-1-yl, azocan-1-yl, azonan-1-yl, 3,4-dihydroisoquinolin-2-yl and the like) (the heterocyclic group is optionally substituted by substituent(s) such as a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);
(i) an optionally substituted amino group [for example, an amino group optionally substituted by 1 or 2 substituents selected from the group consisting of $C_{1-6}$ alkyl, $C_{2-6}$ alkenyl, $C_{6-14}$ aryl, $C_{7-16}$ aralkyl, a heterocyclic group and heterocyclyl-alkyl (the $C_{1-6}$ alkyl, $C_{2-6}$ alkenyl, $C_{6-14}$ aryl, $C_{7-16}$ aralkyl, a heterocyclic group and heterocyclyl-alkyl are each optionally substituted by substituent(s) such as a halogen atom, hydroxy, cyano, amino, optionally halogenated $C_{1-6}$ alkyl (which is not a substituent for alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, mono- or di-$C_{6-14}$ aryl-carbamoyl and the like, and examples of the "heterocyclic group" and "heterocyclyl-" of the "heterocyclyl-alkyl" include those similar to the above-mentioned "heterocyclic group".)];

(j) $C_{3-7}$ cycloalkyl;
(k) an optionally substituted $C_{1-6}$ alkoxy group (the $C_{1-6}$ alkoxy group is optionally substituted by substituent(s) such as a halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ Cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, trimethylsilyl (TMS) and the like);
(l) a formyl group;
(m) a $C_{1-6}$ alkyl-carbonyl group (e.g., acetyl);
(n) a $C_{3-7}$ cycloalkyl-carbonyl group;
(o) a $C_{6-14}$ aryl-carbonyl group;
(p) a $C_{7-16}$ aralkyl-carbonyl group;
(q) a $C_{1-6}$ alkoxy-carbonyl group;
(r) a $C_{6-14}$ aryloxy-carbonyl group;
(s) a $C_{7-16}$ aralkyloxy-carbonyl group;
(t) a $C_{1-6}$ alkylsulfanyl group;
(u) a $C_{1-6}$ alkylsulfinyl group;
(v) a $C_{1-6}$ alkylsulfonyl group;
(w) a carbamoyl group;
(x) a thiocarbamoyl group;
(y) a mono-$C_{1-6}$ alkyl-carbamoyl group (e.g., methylcarbamoyl, ethylcarbamoyl and the like);
(z) a di-$C_{1-6}$ alkyl-carbamoyl group (e.g., dimethylcarbamoyl, diethylcarbamoyl, ethylmethylcarbamoyl and the like);
(aa) a mono- or di-$C_{6-14}$ aryl-carbamoyl group (e.g., phenylcarbamoyl, 1-naphthylcarbamoyl, 2-naphthylcarbamoyl and the like);
(bb) a mono- or di-5- to 7-membered heterocyclyl-carbamoyl group having 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl and the like); and
(cc) an oxo group.

In the present specification, Substituent Group B' consists of
(a) an optionally substituted $C_{1-6}$ alkyl group (the $C_{1-6}$ alkyl group is optionally substituted by substituent(s) such as a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);
(b) an optionally substituted $C_{2-6}$ alkenyl group (the $C_{2-6}$ alkenyl group is optionally substituted by substituent(s) such as a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like); and
(c) an optionally substituted $C_{2-6}$ alkynyl group (the $C_{2-6}$ alkynyl group is optionally substituted by substituent(s) such as a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like).

The symbols in the following formula (1) are explained below.

$R^1$ is an optionally substituted $C_{1-6}$ alkoxy group. Examples of the substituent of the "optionally substituted $C_{1-6}$ alkoxy group" for $R^1$ include substituents selected from the above-mentioned Substituent Group B. The number of the substituents is preferably 0, or 1 or more, more preferably 0 or 1 to 5. The substituent is not a "substituent having optionally substituted cyclic group(s)".

$R^1$ is preferably a $C_{1-6}$ alkoxy group, particularly preferably a methoxy group.

$R^2$ is a hydrogen atom or an optionally substituted $C_{1-6}$ alkyl group. Examples of the substituent of the "optionally substituted $C_{1-6}$ alkyl group" for $R^2$ include substituents selected from the above-mentioned Substituent Group B. The number of the substituents is preferably 0, or 1 or more, more preferably 0 or 1 to 5.

$R^2$ is preferably a hydrogen atom or a $C_{1-6}$ alkyl group, particularly preferably a hydrogen atom or a methyl group.

$R^3$ is

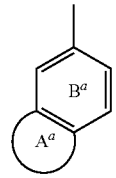

wherein
ring $A^a$ is an optionally substituted 5- or 6-membered heterocycle wherein the substituents for ring $A^a$ are optionally bonded to form a ring; and
ring $B^a$ is an optionally substituted benzene ring or an optionally substituted pyridine ring, or

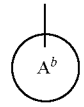

wherein
ring $A^b$ is a substituted pyridine ring, an optionally substituted pyrazole ring, an optionally substituted thiazole ring, an optionally substituted pyrazine ring, an optionally substituted pyridazine ring, an optionally substituted pyrimidine ring or an optionally substituted imidazole ring.

Each symbol in $R^3$ is explained below.
In the formula:

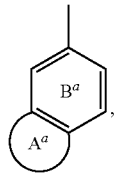

ring $A^a$ is an optionally substituted 5- or 6-membered heterocycle; and ring $B^a$ is an optionally substituted benzene ring or an optionally substituted pyridine ring.

In this case, R³ contains any group represented by the following formula.

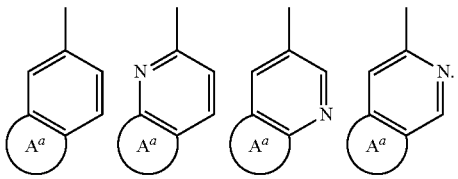

Examples of the "5- or 6-membered heterocycle" of the "optionally substituted 5- or 6-membered heterocycle" for ring $A^a$ include a "5- or 6-membered heterocycle containing, besides carbon atoms, 1 to 4 hetero atoms selected from a nitrogen atom, a sulfur atom and an oxygen atom", from among the above-exemplified "5- or 6-membered heterocycle". Examples of the "5- or 6-membered heterocycle" include a pyrrolidine ring, a tetrahydrofuran ring, a tetrahydrothiophene ring, a piperidine ring, a tetrahydropyran ring, a morpholine ring, a thiomorpholine ring, a piperazine ring, a furan ring, a thiophene ring, a pyrrole ring, an oxazole ring, an isoxazole ring, a thiazole ring, an isothiazole ring, an imidazole ring, a pyrroline ring (e.g., a 1-pyrroline ring, a 2-pyrroline ring, a 3-pyrroline ring), a pyrazole ring, a 1,2,3-oxadiazole ring, a furazan ring, a 1,2,3-thiadiazole ring, a 1,2,3-triazole ring, a pyridine ring, a pyridazine ring, a pyrimidine ring, a pyrazine ring, a triazine ring and the like. Among them, a 2-pyrroline ring, an imidazole ring and the like are preferable.

Examples of the substituent of the "optionally substituted 5- or 6-membered heterocycle" for ring $A^a$ include substituents selected from the above-mentioned Substituent Group A.

Among them, an optionally substituted $C_{1-6}$ alkyl group, an optionally substituted $C_{3-7}$ cycloalkyl group, an oxo group and the like are preferable, and a $C_{1-6}$ alkyl group optionally substituted by substituent(s) selected from a halogen atom and a $C_{3-7}$ cycloalkyl group, a $C_{3-7}$ cycloalkyl group, an oxo group and the like are more preferable.

The substituents for ring $A^a$ are optionally bonded to form a ring. Examples of the ring include a $C_{3-6}$ cycloalkane and the like formed by the substituents for ring $A^a$, in combination, together with the carbon atoms which are ring constituting atoms of ring $A^a$. Preferably, the substituents for ring $A^a$ form a spiro ring with a $C_{3-6}$ cycloalkane.

The number of the substituents of the "optionally substituted 5- or 6-membered heterocycle" for ring $A^a$ is preferably 0, or 1 or more, more preferably 1 to 4, further preferably 3 to 4.

Examples of the substituent of the "optionally substituted benzene ring" for ring $B^a$ include substituents selected from the above-mentioned Substituent Group A. Among them, a halogen atom is preferable.

The number of the substituents of the "optionally substituted benzene ring" for ring $B^a$ is preferably 0, or 1 or more, more preferably 1 to 3, further preferably 1.

Examples of the substituent of the "optionally substituted pyridine ring" for ring $B^a$ include substituents selected from the above-mentioned Substituent Group A.

The number of the substituents of the "optionally substituted pyridine ring" for ring $B^a$ is preferably 0, or 1 or more, more preferably 0, 1 or 2.

In the formula:

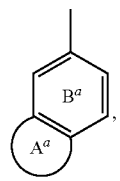

at least one of the two ring-constituting atoms of ring $A^a$ which are adjacent to the two carbon atoms which ring $A^a$ and ring $B^a$ have in common is preferably an atom other than an oxygen atom. That is, the formula:

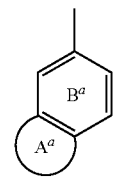

is preferably not the formula:

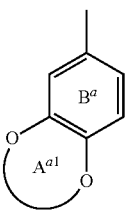

wherein ring $A^{a1}$ is an optionally substituted 5- or 6-membered heterocycle.

In another embodiment, the formula:

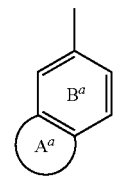

is preferably a group represented by

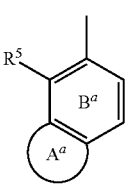

wherein
R⁵ is a substituent, and
the other symbols are defined as in the above-mentioned [1].

Examples of the "substituent" for R⁵ include substituents selected from the above-mentioned Substituent Group A.

$R^5$ is preferably a halogen atom or an optionally substituted $C_{1-6}$ alkoxy group, more preferably a halogen atom (e.g., a fluorine atom).

In another embodiment,
the formula:

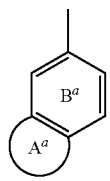

is preferably
a group represented by

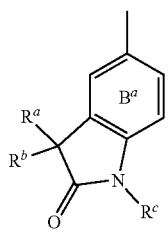

wherein
ring $B^a$ is a benzene ring substituted by halogen atom(s);
$R^a$ and $R^b$ are the same or different and each is a $C_{1-6}$ alkyl group, or $R^a$ and $R^b$ in combination form a $C_{3-6}$ cycloalkane; and
$R^c$ is a $C_{1-6}$ alkyl group optionally substituted by substituent(s) selected from a halogen atom and a $C_{3-7}$ cycloalkyl group, or a $C_{3-7}$ cycloalkyl group, or
a group represented by

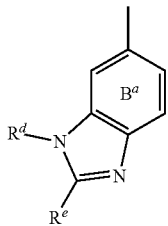

wherein
ring $B^a$ is a benzene ring substituted by halogen atom(s); and
$R^d$ and $R^e$ are the same or different and each is a $C_{1-6}$ alkyl group.

The number of the halogen atoms of the above-mentioned "benzene ring substituted by halogen atom(s)" is preferably 1 to 3, more preferably 1.

In the formula:

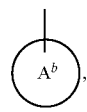

ring $A^b$ is a substituted pyridine ring, an optionally substituted pyrazole ring, an optionally substituted thiazole ring, an optionally substituted pyrazine ring, an optionally substituted pyridazine ring, an optionally substituted pyrimidine ring or an optionally substituted imidazole ring.

Examples of the substituent of the "substituted pyridine ring" for ring $A^b$ include substituents selected from the above-mentioned Substituent Group A. Among them, an oxido group, a $C_{1-6}$ alkoxy group, a pyrrolidinyl group substituted by halogen atom(s), a pyrrolyl group substituted by halogen atom(s) and the like are preferable.

The number of the substituents of the "substituted pyridine ring" for ring $A^b$ is preferably 1 or more, more preferably 1 to 3, particularly preferably 1 or 2.

Examples of the substituent of the "optionally substituted pyrazole ring" for ring $A^b$ include substituents selected from the above-mentioned Substituent Group A. Among them, an optionally substituted $C_{1-6}$ alkyl and the like are preferable, and a $C_{1-6}$ alkyl group substituted by substituent(s) selected from a halogen atom, a $C_{3-7}$ cycloalkyl group optionally substituted by $C_{1-6}$ alkyl group(s) and a phenyl group, and the like are more preferable.

The number of the substituents of the "optionally substituted pyrazole ring" for ring $A^b$ is preferably 0, or 1 or more, more preferably 1 to 3, particularly preferably 1 or 2.

Examples of the substituent of the "optionally substituted thiazole ring", "optionally substituted pyrazine ring", "optionally substituted pyridazine ring", "optionally substituted pyrimidine ring" and "optionally substituted imidazole ring" for ring $A^b$ include substituents selected from the above-mentioned Substituent Group A. The number of the substituents is preferably 0, or 1 or more, more preferably 0 or 1 to 3.

Ring $A^b$ is
preferably a "substituted pyridine ring" or a "substituted pyrazole ring",
more preferably a pyridine ring substituted by substituent(s) selected from an oxido group, an alkoxy group, a pyrrolidinyl group substituted by halogen atom(s) and a pyrrolyl group substituted by halogen atom(s), or
a pyrazole ring substituted by $C_{1-6}$ alkyl group(s) substituted by substituent(s) selected from a halogen atom, a $C_{3-7}$ cycloalkyl group optionally substituted by $C_{1-6}$ alkyl group(s) and a phenyl group.

$R^3$ is preferably

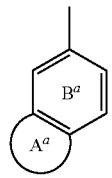

wherein
ring Aa is
a 2-pyrroline ring substituted by substituent(s) selected from a $C_{1-6}$ alkyl group optionally substituted by substituent(s) selected from a halogen atom and a $C_{3-7}$ cycloalkyl group, a $C_{3-7}$ cycloalkyl group and an oxo group, or an imidazole ring optionally substituted by $C_{1-6}$ alkyl group(s) wherein the two substituents bonded to the 2-pyrroline ring, in combination, form a $C_{3-6}$ cycloalkane; and
ring $B^a$ is a benzene ring substituted by halogen atom(s), or

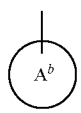

wherein
ring $A^b$ is
a pyridine ring substituted by substituent(s) selected from an oxido group, an alkoxy group, a pyrrolidinyl group substituted by halogen atom(s) and a pyrrolyl group substituted by halogen atom(s),
a pyrazole ring substituted by $C_{1-6}$ alkyl group(s) substituted by substituent(s) selected from a halogen atom,
a $C_{3-7}$ cycloalkyl group optionally substituted by $C_{1-6}$ alkyl group(s) and a phenyl group,
a thiazole ring,
a pyrazine ring,
a pyridazine ring, or
a pyrimidine ring.

In another embodiment,
$R^3$ is preferably
(1) a group represented by

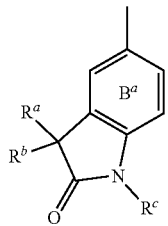

wherein
ring $B^a$ is a benzene ring substituted by halogen atom(s);
$R^a$ and $R^b$ are the same or different and each is a $C_{1-6}$ alkyl group, or $R^a$ and $R^b$ in combination form a $C_{3-6}$ cycloalkane; and
$R^c$ is a $C_{1-6}$ alkyl group optionally substituted by substituent(s) selected from a halogen atom and a $C_{3-7}$ cycloalkyl group, or a $C_{3-7}$ cycloalkyl group,
(2) a group represented by

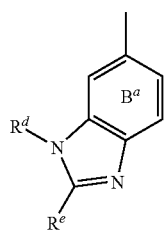

wherein
ring $B^a$ is a benzene ring substituted by halogen atom(s); and
$R^d$ and $R^e$ are the same or different and each is a $C_{1-6}$ alkyl group,
(3) a pyridyl group substituted by substituent(s) selected from a C— alkoxy group, a pyrrolidinyl group substituted by halogen atom(s) and a pyrrolyl group substituted by halogen atom(s),
(4) a pyrazolyl group substituted by $C_{1-6}$ alkyl group(s) substituted by substituent(s) selected from a halogen atom, a $C_{3-7}$ cycloalkyl group optionally substituted by $C_{1-6}$ alkyl group(s) and a phenyl group,
(5) a thiazolyl group,
(6) a pyrazinyl group,
(7) a pyridazinyl group,
(8) a pyrimidinyl group,
or the like.

$R^4$ is an optionally substituted $C_{1-6}$ alkyl group or an optionally substituted phenyl group.

Examples of the substituent of the "optionally substituted $C_{1-6}$ alkyl group" for $R^4$ include substituents selected from the above-mentioned Substituent Group B. Among them, a halogen atom and the like are preferable.

The number of the substituents of the "optionally substituted $C_{1-6}$ alkyl group" for $R^4$ is preferably 0, or 1 or more, more preferably 0 or 1 to 5.

Examples of the substituent of the "optionally substituted phenyl group" for $R^4$ include substituents selected from the above-mentioned Substituent Group A. Among them, a halogen atom, a $C_{1-6}$ alkyl group optionally substituted by halogen atom(s), a $C_{1-6}$ alkoxy group substituted by substituent(s) selected from a halogen atom and a phenyl group, and the like are preferable, and a halogen atom is more preferable.

The number of the substituents of the "optionally substituted phenyl group" for $R^4$ is preferably 0, or 1 or more, more preferably 0 or 1.

$R^4$ is preferably a $C_{1-6}$ alkyl group optionally substituted by halogen atom(s), a phenyl group optionally substituted by halogen atom(s), or the like, more preferably a phenyl group optionally substituted by halogen atom(s), or the like.

Compound (1) is preferably, for example, the following compound (1-A), (1-B) and (1-C).

[Compound (1-A)]
A compound which is compound (1) wherein
$R^1$ is a $C_{1-6}$ alkoxy group,
$R^2$ is a hydrogen atom or a $C_{1-6}$ alkyl group,
$R^3$ is

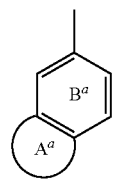

wherein
ring Aa is
a 2-pyrroline ring substituted by substituent(s) selected from a $C_{1-6}$ alkyl group optionally substituted by substituent(s) selected from a halogen atom and a $C_{3-7}$ cycloalkyl group, a $C_{3-7}$ cycloalkyl group and oxo group, or an imidazole ring substituted by $C_{1-6}$ alkyl group(s) wherein the two substituents bonded to the 2-pyrroline ring, in combination, optionally form a $C_{3-6}$ cycloalkane; and
ring $B^a$ is a benzene ring substituted by halogen atom(s), or

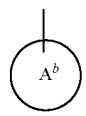

wherein
ring $A^b$ is
a pyridine ring substituted by substituent(s) selected from an oxido group, an alkoxy group, a pyrrolidinyl group substituted by halogen atom(s) and a pyrrolyl group substituted by halogen atom(s),
a pyrazole ring substituted by $C_{1-6}$ alkyl group(s) substituted by substituent(s) selected from a halogen atom,
a $C_{3-7}$ cycloalkyl group optionally substituted by $C_{1-6}$ alkyl group(s) and a phenyl group, a thiazole ring,
a pyrazine ring,
a pyridazine ring, or
a pyrimidine ring, and $R^4$ is a phenyl group optionally substituted by halogen atom(s), or a salt thereof.

[Compound (1-B)]

A compound which is compound (1) wherein
$R^1$ is a $C_{1-6}$ alkoxy group,
$R^2$ is a hydrogen atom or a $C_{1-6}$ alkyl group,
$R^3$ is
(1) a group represented by

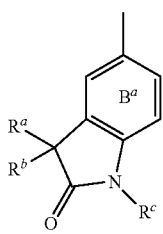

wherein
ring $B^a$ is a benzene ring substituted by halogen atom(s);
$R^a$ and $R^b$ are the same or different and each is a $C_{1-6}$ alkyl group, or $R^a$ and $R^b$ in combination form a $C_{3-6}$ cycloalkane; and
$R^c$ is a $C_{1-6}$ alkyl group optionally substituted by substituent(s) selected from a halogen atom and a $C_{3-7}$ cycloalkyl group, or a $C_{3-7}$ cycloalkyl group,
(2) a group represented by

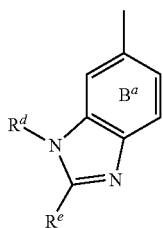

wherein
ring $B^a$ is a benzene ring substituted by halogen atom(s); and
$R^d$ and $R^e$ are the same or different and each is a $C_{1-6}$ alkyl group, or
(3)

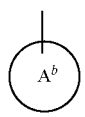

wherein
ring $A^b$ is
a pyridine ring substituted by substituent(s) selected from an oxido group, an alkoxy group, a pyrrolidinyl group substituted by halogen atom(s) and a pyrrolyl group substituted by halogen atom(s),
a pyrazole ring substituted by $C_{1-6}$ alkyl group(s) substituted by substituent(s) selected from a halogen atom, a $C_{3-7}$ cycloalkyl group optionally substituted by $C_{1-6}$ alkyl group(s) and a phenyl group,
a thiazole ring,
a pyrazine ring,
a pyridazine ring, or
a pyrimidine ring, and $R^4$ is a phenyl group optionally substituted by halogen atom(s), a salt thereof.

[Compound (1-C)]

A compound which is compound (1) wherein
$R^1$ is a $C_{1-6}$ alkoxy group,
$R^2$ is a hydrogen atom or a $C_{1-6}$ alkyl group,
$R^3$ is
(1) a group represented by

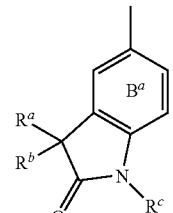

wherein
ring $B^a$ is a benzene ring substituted by halogen atom(s);
$R^a$ and $R^b$ are the same or different and each is a $C_{1-6}$ alkyl group, or $R^a$ and $R^b$ in combination form a $C_{3-6}$ cycloalkane; and
$R^c$ is a $C_{1-6}$ alkyl group optionally substituted by substituent(s) selected from a halogen atom and a $C_{3-7}$ cycloalkyl group, or a $C_{3-7}$ cycloalkyl group,
(2) a group represented by

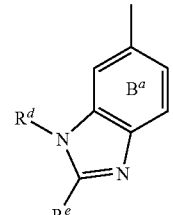

wherein
ring $B^a$ is a benzene ring substituted by halogen atom(s); and
$R^d$ and $R^e$ are the same or different and each is a $C_{1-6}$ alkyl group,
(3) a pyridyl group substituted by substituent(s) selected from a $C_{1-6}$ alkoxy group, a pyrrolidinyl group substituted by halogen atom(s) and a pyrrolyl group substituted by halogen atom(s),
(4) a pyrazolyl group substituted by $C_{1-6}$ alkyl group(s) substituted by substituent(s) selected from a halogen atom, and a $C_{3-7}$ cycloalkyl group optionally substituted by $C_{1-6}$ alkyl group(s),
(5) a thiazolyl group,
(6) a pyrazinyl group,
(7) a pyridazinyl group, or
(8) a pyrimidinyl group, and $R^4$ is a phenyl group optionally substituted by halogen atom(s), or a salt thereof.

As another embodiment, compound (1) is preferably, for example, the following compound (1-D).

[Compound (1-D)]

A compound which is compound (1) wherein
$R^1$ is a $C_{1-6}$ alkoxy group,
$R^2$ is a hydrogen atom or a $C_{1-6}$ alkyl group,
$R^3$ is

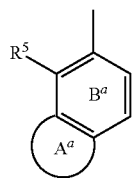

wherein
ring $A^a$ is
a 2-pyrroline ring substituted by substituent(s) selected from a $C_{1-6}$ alkyl group optionally substituted by substituent(s) selected from a halogen atom and a $C_{3-7}$ cycloalkyl group, a $C_{3-7}$ cycloalkyl group and oxo group, or an imidazole ring substituted by $C_{1-6}$ alkyl group(s) wherein the two substituents bonded to the 2-pyrroline ring, in combination, optionally form a $C_{3-6}$ cycloalkane;
ring $B^a$ is a benzene ring; and
$R^5$ is a halogen atom, or

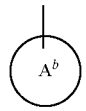

wherein
ring $A^b$ is
a pyridine ring substituted by substituent(s) selected from an oxido group, an alkoxy group, a pyrrolidinyl group substituted by halogen atom(s) and a pyrrolyl group substituted by halogen atom(s), or
a pyrazole ring substituted by $C_{1-6}$ alkyl group(s) substituted by substituent(s) selected from a halogen atom, a $C_{3-7}$ cycloalkyl group optionally substituted by $C_{1-6}$ alkyl group(s) and a phenyl group, and
$R^4$ is a phenyl group optionally substituted by halogen atom(s), or a salt thereof.

Compound (1) is preferably the compounds of Examples 16 to 21, 23 to 27, 32 to 40 and 42 to 55 or a salt thereof.

In addition, the compounds of Examples 1 to 15, 22, 41 and 55 to 102 which are not contained in compound (1) are also encompassed in the present invention.

Hereinafter, compound (1) and the compounds of Examples 1 to 15, 22, 41 and 55 to 102 are collectively referred as "the compound of the present invention".

When the compound of the present invention is a salt, examples of the salt include metal salts, an ammonium salt, salts with organic bases, salts with inorganic acids, salts with organic acids, salts with basic or acidic amino acids, and the like. Preferable examples of the metal salt include alkali metal salts such as a sodium salt, a potassium salt and the like; alkaline earth metal salts such as a calcium salt, a magnesium salt, a barium salt and the like; an aluminum salt and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like. Among them, pharmaceutically acceptable salts are preferable. For example, when the compound has an is acidic functional group, examples thereof include inorganic salts such as alkali metal salts (e.g., a sodium salt, a potassium salt and the like), alkaline earth metal salts (e.g., a calcium salt, a magnesium salt, a barium salt and the like) and the like, an ammonium salt and the like. When the compound has a basic functional group, examples thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

When the compound of the present invention contains a isomer such as tautomer, optical isomer, stereoisomer, regioisomer, rotamer and the like, any isomer and mixture thereof is also encompassed in the compound of the present invention. In addition, when the compound of the present invention contains an optical isomer, an optical isomer resolved from racemate is also encompassed in the compound of the present invention.

The compound of the present invention may be a crystal, the single crystal form and mixture thereof are encompassed in the compound of the present invention.

The compound of the present invention may be a pharmaceutically acceptable cocrystal or cocrystal salt. Here, the cocrystal or cocrystal salt means a crystalline substance constituted by two or more kinds of special solids each having different physical properties (e.g., structure, melting point, melting heat, hygroscopicity, solubility, stability and the like) at room temperature. The cocrystal or cocrystal salt can be produced by a cocrystallization method known per se.

The compound of the present invention may be a solvate (e.g., hydrate and the like), a non-solvate, and both are encompassed in the compound of the present invention.

The compound labeled or substituted with an isotope (e.g., $^2$H, $^3$H, $^{11}$C, $^{14}$C, $^{18}$F, $^{35}$S, $^{125}$I and the like) and the like are also encompassed in the compound of the present invention. The compound of the present invention labeled or substituted with an isotope can be used, for example, as a tracer (PET tracer) used for Positron Emission Tomography (PET), and therefore is useful in the field of medical diagnosis and the like.

[Production Method]

The compound of the present invention and the compound as raw materials can be manufactured by the known means, for example, by the methods shown in the following schemes and the like. Hereinafter, "room temperature" indicates a temperature generally ranging from 0 to 35° C. and "a low temperature" indicates a temperature generally from −78 to 0° C.

Compound (1) is obtained, for example, according to the method explained below, an analogous method thereto, or the like.

The symbols used for the compounds in the reaction schemes indicate the same meanings as mentioned above. In this specification, a methyl group (—$CH_3$) is sometimes abbreviated as Me. The compounds in the schemes can include salts thereof in the cases when salts can be formed and such salts are similar to the salts of the compound of the present invention. Further, the compound obtained in each process can be used directly as a reaction mixture or as a crude product in the following reactions. However, it can be isolated from the reaction mixture according to the ordinary method. The product itself can be easily purified by the known means of isolation such as extraction, concentration, neutralization, filtration, distillation, recrystallization, chromatography and the like. Alternatively, if the compound in the schemes is commercially available, a commercial product can be used directly and in addition, those which are manufactured by the known methods or an analogous method thereof can be used. If the compound as a raw material contains amino, carboxy, hydroxyl or a heterocyclic group, the group can be protected by a protective group that is generally used in the peptide chemistry. In this case, after reacting, if desirable, target compound can be obtained by removing the protective group. The protective group can be introduced or removed by the known methods, for example, based on the methods described in "Protective Groups in Organic Synthesis, $3^{rd}$ Edition" (by Theodora W. Greene, Peter G. M. Wuts, published in 1999 by Wiley-Interscience Corporation).

Examples of the "X-" include halogen anions (e.g., a chlorine anion, a bromine anion, an iodine anion etc.), a nitrate ion, and a phosphate ion.

In these production methods, conversions of each substituents for $R^1$-$R^4$ can be carried out according to a method known per se, for example, the method described in "Comprehensive Organic Transformations" (by Richard C. Larock, published in 1999 by Wiley-VCH).

The following respective processes can be carried out without a solvent or the compound as a raw material can be dissolved or suspended in an appropriate solvent prior to the reaction. In this case, one kind of solvent can be used independently or two or more solvents can be combined at an appropriate ratio. Specific examples of the solvents to be used in the production methods for the compound of the present invention are given as follows:

Alcohols: methanol, ethanol, 1-propanol, 2-propanol, tert-butyl alcohol, 2-methoxyethanol, etc.

Ethers: diethyl ether, diisopropyl ether, diphenyl ether, tetrahydrofuran, 1,4-dioxane, 1,2-dimethoxyethane, etc.

Aromatic hydrocarbons: benzene, chlorobenzene, toluene, xylene, etc.

Saturated hydrocarbons: cyclohexane, hexane, etc.

Amides: N,N-dimethylformamide, N,N-dimethylacetamide, hexamethylphosphoric triamide, etc.

Halogenated hydrocarbons: dichloromethane, chloroform, carbon tetrachloride, 1,2-dichloroethane, etc.

Nitriles: acetonitrile, propionitrile, etc.

Sulfoxides: dimethyl sulfoxide, etc.

Aromatic organic bases: pyridine, lutidine, etc.

Acid anhydrides: acetic anhydride, etc.

Organic acids: formic acid, acetic acid, propionic acid, trifluoroacetic acid, methanesulfonic acid, etc.

Inorganic acids: hydrochloric acid, sulfuric acid, etc.

Esters: methyl acetate, ethyl acetate, butyl acetate, etc.

Ketones: acetone, methyl ethyl ketone, etc.

Specific examples of bases or deoxidizers that are used in the production methods for the compound of the present invention are given as follows:

Inorganic bases: sodium hydroxide, potassium hydroxide, magnesium hydroxide, etc.

Basic salts: sodium carbonate, potassium carbonate, cesium carbonate, calcium carbonate, sodium hydrogen carbonate, etc.

Organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole, etc.

Metal alkoxides: sodium methoxide, sodium ethoxide, potassium tert-butoxide, etc.

Alkali metal hydrides: sodium hydride, potassium hydride, etc.

Metal amides: sodium amide, lithium diisopropylamide, lithium hexamethyldisilazide, etc.

Organolithium reagents: methyl lithium, n-butyl lithium, sec-butyl lithium, tert-butyl lithium, etc.

Specific examples of acids or acid catalysts that are used in the production methods for the compound of the present invention are given as follows:

Inorganic acids: hydrochloric acid, sulfuric acid, nitric acid, hydrobromic acid, phosphoric acid, etc.

Organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.

Lewis acids: trifluoroboron ether complex, zinc iodide, anhydrous aluminum chloride, anhydrous zinc chloride, anhydrous iron chloride, etc.

When a "heterocyclic compound", "carbamate compound", "acetylene derivative", "boronic acid derivative" or "organo tin compound" and the like are bonded to $R^3$ having a leaving group, the reaction can be carried out by coupling reaction in the presence of a base, using both or either of a palladium catalyst and a copper catalyst, and the like. Examples of the "heterocyclic compound" include imidazole ring compounds, pyrazole ring compounds, pyrrolidine ring compounds, piperidine ring compounds, morpholine ring compounds, oxazepane ring compounds, azetidine ring compounds, pyrrolidone ring compounds, piperidone ring compounds and the like. Examples of the "carbamate compound" include oxazolidone ring compounds and the like. Examples of the "acetylene derivative" include cyclopropylacetylene and the like. Examples of the "boronic acid derivative" include (1-methyl-1H-pyrazol-4-yl)boronic acid pinacol ester and the like. Examples of the "organo tin compound" include 2-(tributylstannyl)-1,3-oxazole and the like.

Examples of the "palladium catalyst" include tris(dibenzylideneacetone)dipalladium(0), tetrakistriphenylphosphinepalladium(0) and the like. The "palladium catalyst" can be used in an amount of about 0.01-1 mol, preferably 0.05-0.2 mol, per 1 mol of the reaction substrate. The "palladium catalyst" can be used together with a phosphine ligand. When using a phosphine ligand, it is used in an amount of about 0.01-4 mol, preferably 0.05-1 mol, per 1 mol of the reaction substrate. Examples of the "phosphine ligand" include triphenylphosphine, 4,5-bis(diphenylphosphino)-9,9-dimethylxanthene and the like. Examples of the "copper catalyst" include copper iodide (CuI), copper oxide ($Cu_2O$) and the like. The "copper catalyst" is used in an amount of about 0.1-1 mol, preferably 0.1-0.5 mol, per 1 mol of the reaction substrate. The "copper catalyst" can be used together with a ligand such as N,N'-dimethylethane-1,2-diamine, trans-1,2-diaminocyclohexane, salicylaldoxime and the like. The ligand is used in an amount of about 0.1-4 mol, preferably 0.1-2 mol, per 1 mol of the reaction substrate. Examples of the "base" include sodium tert-butoxide and potassium phosphate, and the amount is about 1 to 10 mol, preferably from 1 to 3 mol, per 1 mol of the reaction substrate. The reaction is advantageously carried out without a solvent or in the presence of a solvent inert to the reaction. While the solvent to be used is not particularly limited as long as the reaction proceeds, ethers, nitriles and the like are preferable. The reaction is generally carried out at room temperature or under heating with reflux, preferably under heating with reflux. The reaction time is generally from 0.5 to 48 hours, preferably from 1 to 24 hours.

This coupling reaction can be carried out according to the method described in "Cross-Coupling Reactions: A Practical Guide (Topics in Current Chemistry)" (Springer), "Experimental Organometallic Chemistry for Synthesizing Chemists" (Kodansha) or "Organic Synthesis using Transition Metals" (Kagaku Dojin), or an analogous method thereto.

Compound (1) can be synthesized, for example, according to Production Method A, Production Method B, Production Method C or the like which is explained below.

Unless otherwise specified, the symbols in each formula in the reaction schemes are as defined above. In each reaction shown in the Production Method A-C, "X⁻" is a halogen anion (e.g., a chlorine anion, a bromine anion, an iodine anion etc.), a nitrate ion or a phosphate ion, and Y is a leaving group such as a halogen atom (F, Cl, Br, I etc.), a methanesulfonyloxy group, a trifluoromethanesulfonyloxy group or the like.

[Production Method A]

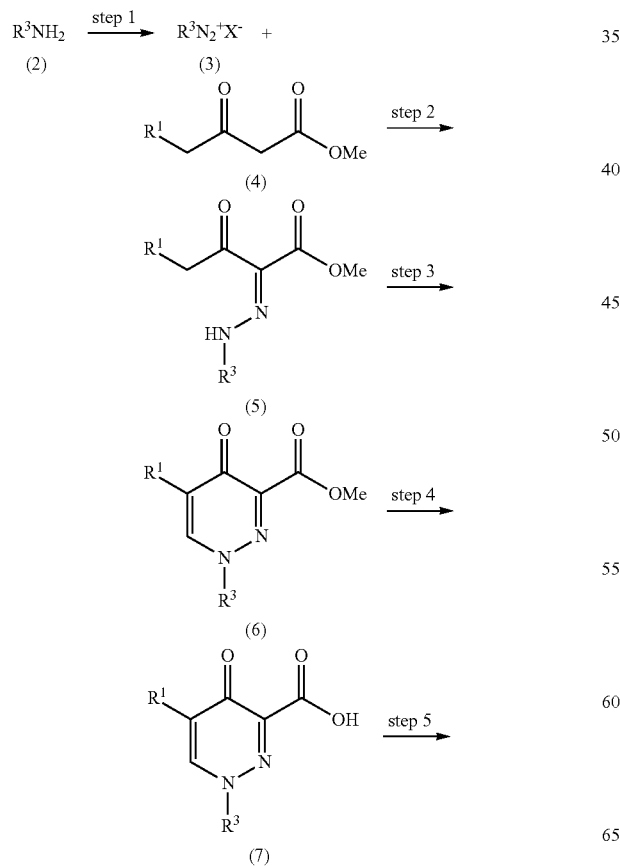

[Production Method B]

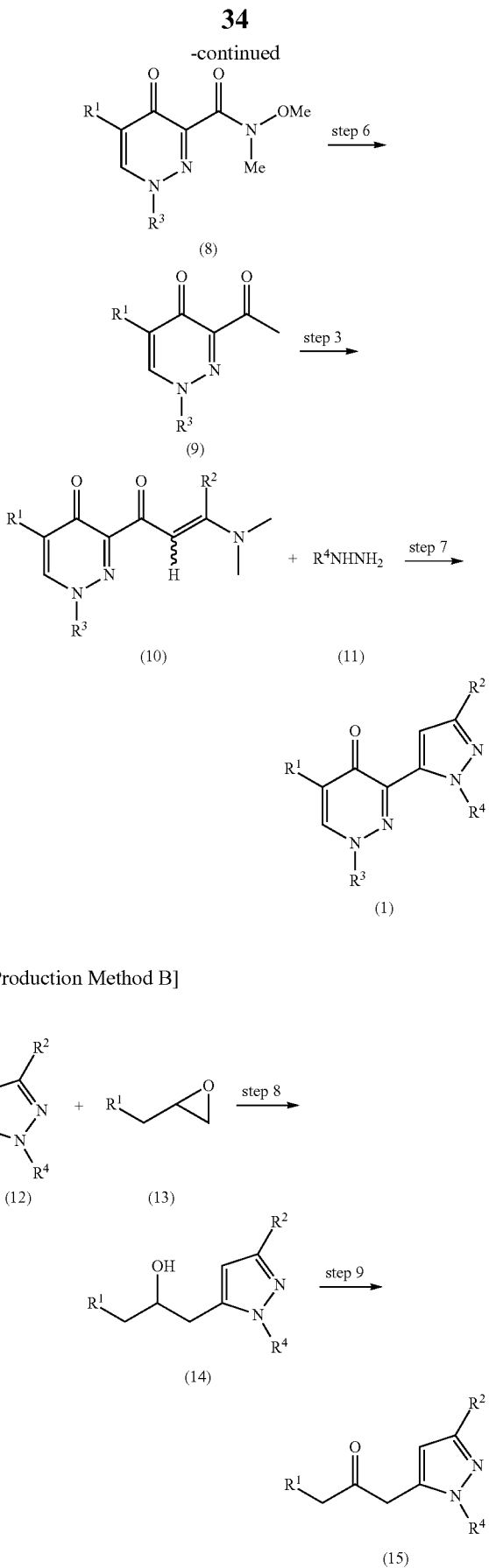

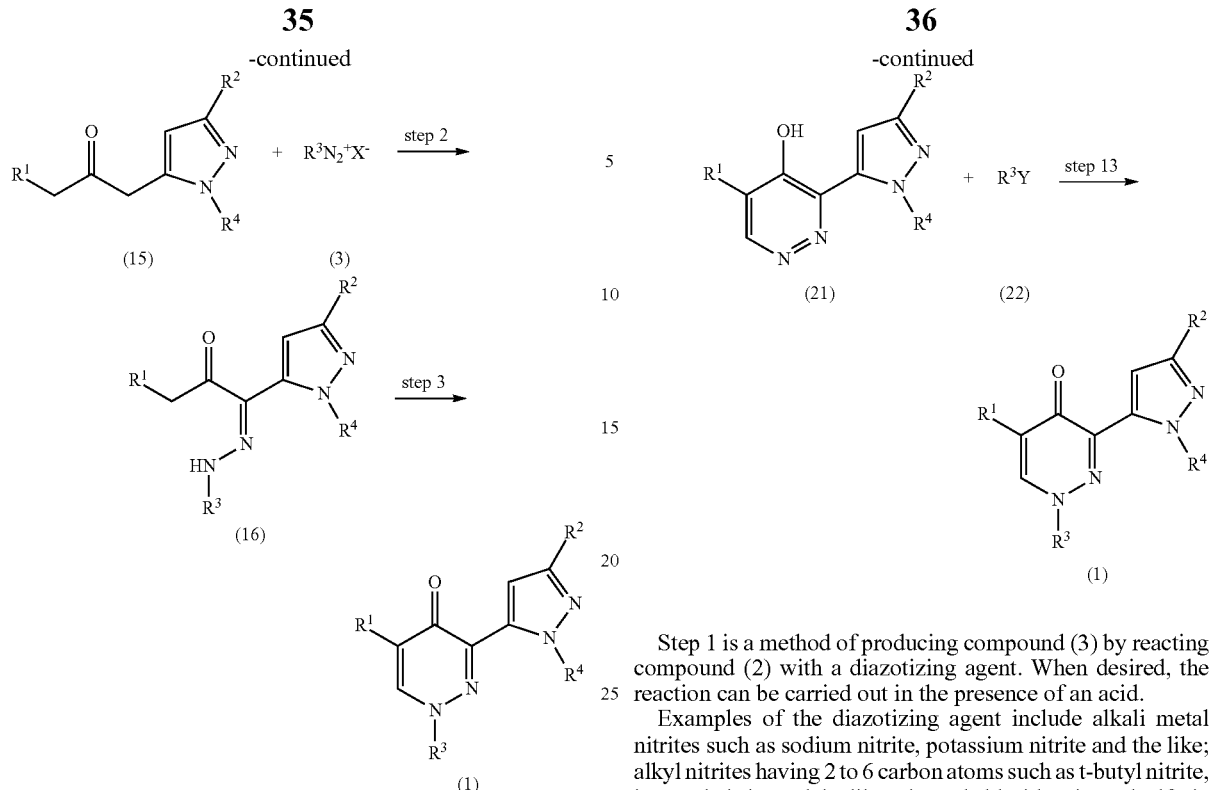

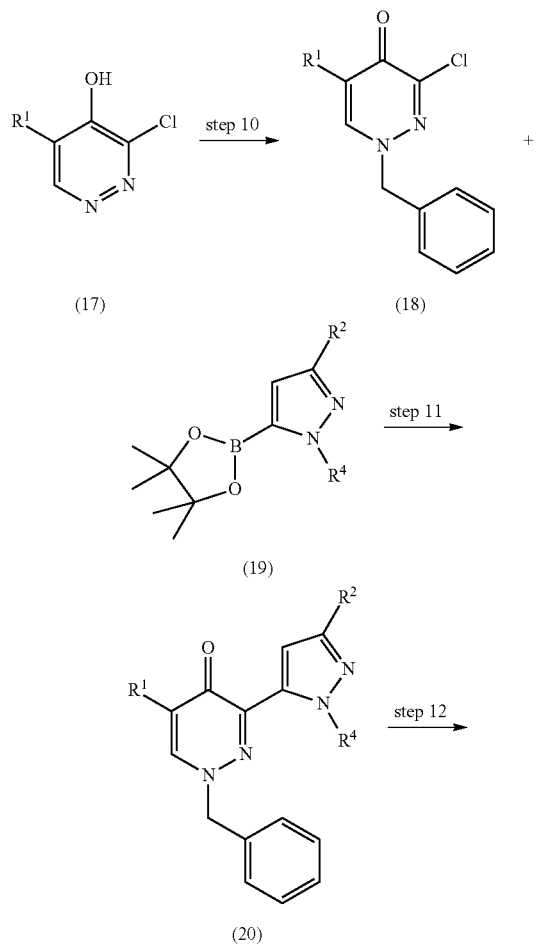

[Production Method C]

Step 1 is a method of producing compound (3) by reacting compound (2) with a diazotizing agent. When desired, the reaction can be carried out in the presence of an acid.

Examples of the diazotizing agent include alkali metal nitrites such as sodium nitrite, potassium nitrite and the like; alkyl nitrites having 2 to 6 carbon atoms such as t-butyl nitrite, isoamyl nitrite and the like; nitrosyl chloride, nitrosylsulfuric acid, nitric oxide and the like. Among them, sodium nitrite is preferable from the aspects of low cost and easy availability. In addition, an alkyl nitrite is preferable from the aspects of high reactivity. Since an alkali metal nitrite is solid at ambient temperature, it may be dissolved in water prior to use.

Examples of the "acid" include hydrochloric acid, sulfuric acid, acetic acid and the like, and the acid may be used in a mixture of two or more thereof.

The amount of the diazotizing agent to be used is 1-5 mol, preferably 1-2 mol, per 1 mol of compound (2), from the aspects of high reactivity and economic efficiency. This reaction is generally carried out at room temperature or low temperature, preferably at −30° C. to 0° C.

The reaction time is generally 1 min-3 hr, preferably 1 min-1 hr.

The reaction is advantageously carried out without a solvent or in the presence of a solvent inert to the reaction. While the solvent to be used is not particularly limited as long as the reaction proceeds, water is preferable.

Step 2 is a method of producing compound (5) or compound (16) by reacting compound (3) in the presence of compound (4) or compound (15).

This step can be carried out according to the method described in Tetrahedron Lett., 2008, 49(14), 2262-2264, or an analogous method thereto. When desired, the reaction can be carried out in the presence of a base.

The amount of compound (4) or compound (15) to be used is about 1-5 mol, preferably 1-2 mol, per 1 mol of compound (3).

Examples of the "base" include sodium acetate.

The amount of the "base" to be used is generally 1-10 equivalents, preferably 2-6 equivalents, relative to compound (3).

The reaction is advantageously carried out without a solvent or in the presence of a solvent inert to the reaction. While the solvent to be used is not particularly limited as long as the reaction proceeds, a mixed solvent of an alcohol and water is preferable.

This reaction is generally carried out at room temperature, or at low temperature under cooling in ice bath.

The reaction time is generally 5 sec-24 hr, preferably 5 sec-1 hr.

Step 3 is a method of producing compound (6), compound (10) or compound (1) from compound (5), compound (9) or compound (16). The reaction can be carried out in the presence of N,N-dimethylformamide dimethyl acetal, N,N-dimethylacetamide dimethyl acetal and the like as a solvent.

This step can be carried out according to the method described in Journal of Heterocyclic Chemistry, 1981, 18, 333-334, or an analogous method thereto.

This reaction is generally carried out under heating with reflux, preferably at 100° C.-150° C.

The reaction time is generally 1-10 hr, preferably 1-hr.

Step 4 is a method of producing compound (7) from compound (6). The reaction can be carried out under an acidic or basic condition. This reaction is advantageously carried out without a solvent or with a solvent inert to the reaction. While the solvent to be used is not particularly limited as long as the reaction proceeds, an alcohol, a solvent mixed with water, and an ether are preferable.

Examples of the "acid" include inorganic acids.

Examples of the "base" include inorganic bases such as sodium hydroxide, potassium hydroxide and the like. In addition, lithium hydroxide can also be used.

The amount of the acid or base to be used is about 1-10 mol, preferably 1-5 mol, per 1 mol of compound (6).

The reaction is generally carried out at room temperature or under heating, preferably at room temperature.

The reaction time is generally 1-48 hr, preferably 3-hr.

Step 5 is a method of producing compound (8) from compound (7). Compound (8) can be produced using N,O-dimethylhydroxylamine hydrochloride and a condensing agent, in the presence of a base such as triethylamine, N,N-diisopropylethylamine and the like. Alternatively, Compound (8) can also be produced by converting the substrate carboxylic acid into the corresponding acid halide, and then reacting the acid halide with N,O-dimethylhydroxylamine hydrochloride.

Examples of the "condensing agent" include 1-ethyl-3-(3-dimethylaminopropyl)-carbodiimide hydrochloride in the presence of 1-hydroxybenzotriazole.

The reaction is advantageously carried out without a solvent or with a solvent inert to the reaction. While the solvent to be used is not particularly limited as long as the reaction proceeds, a nitrile, an ether and an amide are preferable.

The amount of the N,O-dimethylhydroxylamine hydrochloride to be used is about 1-5 mol, preferably 1-3 mol, per 1 mol of compound (7).

The amount of the condensing agent to be used is about 1-5 mol, preferably 1-3 mol, per 1 mol of compound (7).

The amount of the base (e.g., triethylamine, N,N-diisopropylethylamine and the like) to be used is about 1-10 mol, preferably 2-3 mol, per 1 mol of compound (7).

The reaction is generally carried out at room temperature or under heating, preferably at room temperature.

The reaction time is generally 1-48 hr, preferably 5-hr.

Compound (8) can be synthesized by reacting the acid halide with N,O-dimethylhydroxylamine hydrochloride in the presence of a base such as triethylamine and the like.

The reaction is advantageously carried out without a solvent or with a solvent inert to the reaction. While the solvent to be used is not particularly limited as long as the reaction proceeds, an ether, an ester and an amide are preferable.

The amount of the N,O-dimethylhydroxylamine hydrochloride to be used is about 1-5 mol, preferably 1-3 mol, per 1 mol of compound (7).

The amount of the base (e.g., triethylamine and the like) to be used is about 1-10 mol, preferably 2-3 mol, per 1 mol of compound (7).

This reaction is generally carried out under ice-cooling or at room temperature, preferably under ice-cooling.

The reaction time is generally 0.5-5 hr, preferably 1-3 hr.

Alternatively, compound (8) can be produced by reacting compound (6) with trimethylaluminum and N,O-dimethylhydroxylamine hydrochloride in the presence of an organic base. The amount of the organic base, trimethylaluminum and N,O-dimethylhydroxylamine hydrochloride to be used is about 1-10 mol, preferably 2-5 mol, per 1 mol of compound (6). This reaction is advantageously carried out without a solvent or with a solvent inert to the reaction. While the solvent to be used is not particularly limited as long as the reaction proceeds, a halogenated hydrocarbon is preferable. This reaction is generally carried out under ice-cooling or at room temperature, preferably under ice-cooling. The reaction time is generally 1-24 hr, preferably 1-5 hr.

Step 6 is a method of producing compound (9) from compound (8). Compound (9) can be produced using an "alkylating agent" such as the Grignard reagent, an organolithium reagent and the like.

The reaction is advantageously carried out without a solvent or with a solvent inert to the reaction. While the solvent to be used is not particularly limited as long as the reaction proceeds, an ether is preferable.

The amount of the "alkylating agent" to be used is about 1-10 mol, preferably 2-3 mol, per 1 mol of compound (8).

This reaction is generally carried out at −78° C. or under ice-cooling, preferably at −78° C. The reaction time is generally 1-10 hr, preferably 1-3 hr.

Step 7 is a method of producing compound (1) by reacting compound (10) in the presence of compound (11).

The amount of compound (11) to be used is about 1-10 mol, preferably about 2-5 mol, per 1 mol of compound (10).

The reaction is advantageously carried out without a solvent or in the presence of a solvent inert to the reaction. While the solvent to be used is not particularly limited as long as the reaction proceeds, an alcohol, an organic acid and a mixed solvent thereof are preferable.

This reaction is generally carried out under ice-cooling, at room temperature or under heating with reflux, preferably at 0° C.-150° C.

The reaction time is generally 0.1-10 hr, preferably 0.5-5 hr.

This step is can be carried out according to the method described in Journal of Heterocyclic Chemistry, 1981, 18, 333-334, or an analogous method thereto.

In this step, $R^4$ is an optionally substituted $C_{1-6}$ alkyl group or an optionally substituted phenyl group.

Step 8 is a method of producing compound (14) from compound (12). Compound (14) can be produced by reacting compound (12) with compound (13) in the presence of an organolithium reagent such as n-butyllithium and the like.

The organolithium reagent is used in an amount of about 1-10 mol, preferably 1-3 mol, per 1 mol of compound (12), and compound (13) is used in an amount of about 1-10 mol, preferably 1-3 mol, per 1 mol of compound (12).

The reaction is advantageously carried out without a solvent or in the presence of a solvent inert to the reaction. While the solvent to be used is not particularly limited as long as the reaction proceeds, an ether, particularly tetrahydrofuran is preferable.

This reaction is generally carried out at room temperature or low temperature, preferably at −78° C.-0° C.

The reaction time is generally 0.5 hr-12 hr, preferably 1 hr-5 hr.

Step 9 is a method of producing compound (15) from compound (14). Compound (15) can be produced using an appropriate oxidation reaction.

Examples of the "oxidation reaction" include Swern oxidation reaction, oxidation reaction using an oxidant such as sulfur trioxide pyridine complex, pyridinium chlorochromate and the like. In the case of the oxidation reaction using an oxidant, the oxidant is used in an amount of about 1-10 mol, preferably 1-3 mol, per 1 mol of compound (14). The reaction is advantageously carried out without a solvent or with a solvent inert to the reaction. While the solvent to be used is not particularly limited as long as the reaction proceeds, dimethyl sulfoxide, a halogenated hydrocarbon and an ester are preferable. This reaction is preferably carried out at low temperature or room temperature. The reaction time is generally 1-10 hr, preferably 1-3 hr.

This step can be carried out according to the method described in Comprehensive Organic Transformations (WILEY-VCH), or Oxidation in Organic Chemistry (American Chemical Society), or an analogous method thereto.

Step 10 is a method of producing compound (18) from compound (17). Compound (18) can be produced by reacting compound (17) with benzyl bromide and the like in the presence of an alkali metal hydride such as sodium hydride and the like.

The alkali metal hydride is used in an amount of about 1-10 mol, preferably 1-3 mol, per 1 mol of compound (17), and the benzyl bromide is used in an amount of about 1-10 mol, preferably 1-3 mol, per 1 mol of compound (17).

In addition, an additive such as tetrabutylammonium iodide and the like may be added to the reaction system to promote the reaction. The amount of the additive (e.g., tetrabutylammonium iodide and the like) to be used is about 0.1-3 equivalents, preferably 0.1-1 equivalents, relative to compound (17).

This reaction is advantageously carried out without a solvent or with a solvent inert to the reaction. While the solvent to be used is not particularly limited as long as the reaction proceeds, an amide, an ether and a mixed solvent thereof are preferable.

This reaction is generally carried out at room temperature or low temperature, preferably at 0° C.—room temperature.

The reaction time is generally 0.5 hr-48 hr, preferably 1 hr-24 hr.

Step 11 is a method of producing compound (20) from compound (18) and compound (19). Compound (20) can be produced using a palladium catalyst in the presence of a base.

The amount of compound (19) to be used is about 1-10 mol, preferably about 1-3 mol, per 1 mol of compound (18).

Examples of the "base" include potassium acetate, potassium carbonate and the like. The amount thereof is about 1-10 mol, preferably 1-3 mol, per 1 mol of compound (18).

Examples of the "palladium catalyst" include bis[di-tert-butyl(4-dimethylaminophenyl)phosphine]dichloropalladium(II), tetrakis(triphenylphosphine)palladium(0) and the like. The amount thereof is about 0.01-0.5 mol, preferably 0.03-0.1 mol, per 1 mol of compound (18).

The reaction is advantageously carried out without a solvent or with a solvent inert to the reaction. While the solvent to be used is not particularly limited as long as the reaction proceeds, a mixed solvent of an alcohol and water, an aromatic hydrocarbon, an ether, an amide and the like are preferable.

This reaction is generally carried out at room temperature or under heating with reflux, preferably under heating with reflux.

The reaction time is generally 1-48 hr, preferably 10-20 hr.

This step can be carried out according to the method described in Org. Lett., 2006, 8, 1787-1789, or an analogous method thereto.

Step 12 is a method of producing compound (21) from compound (20). Compound (21) can be produced by hydrogenation reaction in the presence of a catalyst such as palladium on carbon and the like.

This reaction can be carried out according to a method known per se, for example, the method described in Wiley-Interscience, 1999, "Protective Groups in Organic Synthesis, 3$^{rd}$ Ed." (Theodora W. Greene, Peter G. M. Wuts), or the like.

Step 13 is a method of producing compound (1) from compound (21). Compound (1) can be produced by reacting compound (21) with compound (22) in the presence of a base.

The amount of compound (22) to be used is about 1-10 mol, preferably 1-3 mol, per 1 mol of compound (21). The base to be used is preferably a basic salt such as cesium carbonate and the like. The base is used in an amount of about 1-10 mol, preferably 1-3 mol, per 1 mol of compound (21).

The reaction is advantageously carried out without a solvent or with a solvent inert to the reaction. While the solvent to be used is not particularly limited as long as the reaction proceeds, an amide, a sulfoxide and the like are preferable.

This reaction is generally carried out at room temperature or under heating with reflux, preferably at 100° C.-150° C. under heating with reflux.

The reaction time is generally 1-120 hr, preferably 10-72 hr.

This reaction may be carried out in the presence of a copper catalyst, while it is not particularly limited as long as the reaction proceeds. Examples of the copper catalyst include copper iodide (CuI) and the like. The copper catalyst is used in an amount of about 0.1-1 mol, preferably 0.1-0.5 mol, per 1 mol of compound (21). In addition, a ligand such as 4,7-dimethoxy-1,10-phenanthroline and the like may be used. The ligand is used in an amount of about 0.1-1 mol, preferably 0.1-0.5 mol, per 1 mol of compound (21).

The reaction is advantageously carried out without a solvent or with a solvent inert to the reaction. While the solvent to be used is not particularly limited as long as the reaction proceeds, an amide, a sulfoxide and the like are preferable.

This reaction is generally carried out at room temperature or under heating with reflux, preferably at 100° C.-150° C. under heating with reflux.

The reaction time is generally 1-120 hr, preferably 10-72 hr.

The compounds of Examples 1 to 15, 22, 41 and 55 to 102 can be produced according to each Example mentioned below.

The compound of the present invention obtained by the aforementioned methods can be isolated or purified by the ordinary separation means such as recrystallization, distillation, chromatography and the like. When the compound of the present invention thus obtained is obtained in a free form, they can be converted to their salts by the known methods or an analogous method thereof (e.g., neutralization, etc.), or in reverse, if they are obtained in the salt, they can be converted to a free form or other salts by the known methods or an analogous method thereof.

When the compound of the present invention is present as a configuration isomer, a diastereomer, a conformer and the like, they can be respectively isolated when desired by the above-mentioned separation and purification means. When the compound of the present invention is a racemate, it can be separated into a d-form and an l-form by the ordinary optical separation means.

The starting compound used for the production of the compound of the present invention may be a salt as long as the reaction is not impaired. Examples of such salt include salts similar to those of the compound of the present invention.

In any of the above mentioned production methods or processes, if desired, the compound of the present invention can be synthesized by further applying one or combination of known reactions such as protection-deprotection reactions, acylation reactions, alkylation reactions, hydrogenation reactions, oxidation reactions, reduction reactions, carbon chain extension reactions, substituent exchanging reactions and the like.

The compound of the present invention may be used as a prodrug. A prodrug of the compound of the present invention means a compound which is converted to the compound of the present invention by a reaction using enzyme, gastric acid, etc. under the physiological conditions in the living body, that is, a compound which is converted to the compound of the present invention by enzymatical oxidation, reduction, hydrolysis, etc.; a compound which is converted to the compound of the present invention by hydrolysis etc. using gastric acid, etc.

A prodrug of the compound of the present invention may be a compound obtained by subjecting an amino group in the compound of the present invention to an acylation, alkylation or phosphorylation (e.g., a compound obtained by subjecting an amino group in the compound of the present invention to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in the compound of the present invention to an acylation, alkylation, phosphorylation or boration (e.g., a compound obtained by subjecting an hydroxy group in the compound of the present invention to an acetylation, palmitoylation, propanoylation, pivaloylation, succinylation, fumarylation, alanylation, dimethylaminomethylcarbonylation, etc.); a compound obtained by subjecting a carboxyl group in compound of the present invention to an esterification or amidation (e.g., a compound obtained by subjecting a carboxyl group in the compound of the present invention to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methylamidation, etc.) and the like. Any of these compounds can be produced from the compound of the present invention by a method known per se. A prodrug for the compound of the present invention may also be one which is converted into the compound of the present invention under a physiological condition, such as those described in IYAKUHIN no KAIHATSU (Development of Pharmaceuticals), Vol. 7, Design of Molecules, p. 163-198, Published by HIROKAWA SHOTEN (1990).

The compound of the present invention has an excellent PDE10A inhibitory activity, and for example, is useful as a medicament for preventing or treating the following diseases and symptoms.

psychotic disorder (e.g., brief psychotic disorder, induced delusional disorder);
psychotic diseases induced by alcohol, amphetamine, cannabinoid, cocaine, hallucinogenic drug, obesity, opioids, phencyclidine and the like;
delusional disorder;
anxiety disorder;
movement disorder;
mood disorder;
major depression;
depression overlapping with psychotic disorders including delusional disorder or schizophrenia;
major depressive episode of mild, moderate or severe type;
manic or mixed episode;
hypomanic episode;
depressive episode with atypical features;
depressive episode with melancholic features;
depressive episode with catatonic features;
mood episode with postpartum onset;
post-stroke depression;
dysthymic disorder;
minor depression;
autism;
drug addiction;
neurodegenerative disease;
neurodegeneration associated with brain trauma;
neurodegeneration associated with cerebral stroke;
neurodegeneration associated with cerebral infarction;
hypoglycemia-induced neurodegeneration;
neurodegeneration associated with epilepsy seizure;
neurodegeneration associated with neurotoxin;
multiple system atrophy;
Alzheimer's disease;
dementia;
multi-infarct dementia;
alcoholic dementia or other drug-related dementia;
dementia associated with intracranial tumor or cerebrum trauma;
dementia associated with Huntington's disease or Parkinson's disease;
AIDS-related dementia syndrome;
frontotemperal dementia;
delirium;
amnestic disorder;
post-traumatic stress disorder;
mental retardation (hypophrenia);
learning disorder (e.g., dyslexia, dyscalculia, agraphia);
attention-deficit hyperactivity disorder;
age-related cognitive decline;
premenstrual dysphoric disorder;
bipolar disorder including bipolar I disorder or bipolar II disorder;
cyclothymic disorder;
Parkinson's disease;
Huntington's disease;
delusion;
schizophrenia (e.g., paranoid schizophrenia, disorganized schizophrenia, catatonic schizophrenia, undifferentiated schizophrenia, residual schizophrenia);
schizoaffective disorder;
schizoaffective disorder of the delusional type or the depressive type;
personality disorder of the paranoid type;
personality disorder of the schizoid type;
obesity;
metabolic syndrome;
non-insulin dependent diabetes;
glucose intolerance.

In particular, the compound of the present invention is useful for preventing or treating schizophrenia.

The compound of the present invention is superior in metabolic stability, so that the compound of this invention can be expected to have an excellent therapeutic effect on the above-mentioned diseases even in a low dose.

In particular, since compound (1) has a group represented by $R^1$ (optionally substituted alkoxy group), it shows high PDE10A inhibitory activity and high PDE10A selectivity, and can prevent oxidation reactions such as epoxidation and the like.

A preferable embodiment of the present invention, which is a compound of the present invention wherein $R^1$ is a methoxy group, $R^3$ is a substituted pyridinyl group, a substituted pyrazolyl group, a substituted oxoindolyl group or a substituted benzimidazolyl group, and $R^4$ is a phenyl group, shows high solubility and good in vivo kinetics.

Particularly, when $R^3$ is a fused ring of the formula

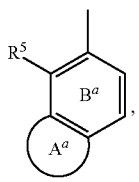

which is formed by ring $B^a$ and ring $A^a$, the activity increases on space model by specifying the substitutable position of the fused ring for $R^5$. Furthermore, it is considered that the presence of substituent for $R^5$ suppresses the toxicity and improves the selectivity of PDE10A inhibitory activity.

In addition, when $R^3$ is a substituted pyridyl group, a salt can be formed, and the solubility can be improved. Furthermore, when $R^3$ is an optionally substituted pyrazolyl group, improvement of solubility and improvement of Blood-Brain Barrier Penetration can be expected, since the molecular weight decreases.

Since the compound of the present invention has low toxicity (e.g., more superior as medicament in terms of acute toxicity, chronic toxicity, genetic toxicity, reproductive toxicity, cardiotoxicity, drug interaction, carcinogenicity and the like), it can be safely administered as it is as a medicament, or as a pharmaceutical composition obtained by mixing with a pharmaceutically acceptable carrier etc., orally or parenterally to a mammal (e.g., human, monkey, bovine, horse, swine, mouse, rat, hamster, rabbit, cat, dog, sheep, goat etc.).

The compound of the present invention can be used singly as a medicament according to a method known per se (e.g., the method described in the Japanese Pharmacopoeia etc.) as a production method of a pharmaceutical preparation. In addition, the compound of the present invention can be used as a pharmaceutical composition by mixing with a pharmacologically acceptable carrier.

A medicament containing the compound of the present invention can be safely administered as, for example, tablets (inclusive of sugar-coated tablet, film-coated tablet, sublingual tablet, orally disintegrable tablet, buccal, etc.), pills, powders, granules, capsules (inclusive of soft capsule, and microcapsule), troches, syrups, liquids, emulsions, suspensions, controlled-release preparations (e.g., quick-release preparation, sustained-release preparation, sustained-release microcapsule), aerosols, films (e.g., orally disintegrable film, oral mucosal adhesive film), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, and directly to lesion).

As a pharmaceutical acceptable carrier, common organic or inorganic carrier substances are used as formulation raw materials. Carriers are added as vehicles, lubricants, binders and disintegrants in the solid formulations; and as solvents, solubilizing agents, suspending agents, isotonization agents, buffers, soothing agents etc. in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, microcrystalline cellulose, low-substituted hydroxypropyl cellulose, sodium carboxymethylcellulose, gum Arabic, pullulan, light anhydrous silicic acid, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, microcrystalline cellulose, sucrose, D-mannitol, trehalose, dextrin, pullulan, hydroxypropyl cellulose, hydroxypropyl methyl cellulose and polyvinyl pyrrolidone.

Favorable examples of the disintegrants are as follows: lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzyl benzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose, etc.; polysorbates, and polyoxyethylene hydrogenated castor oil.

Favorable examples of the isotonization agents include sodium chloride, glycerin, D-mannitol, D-sorbitol and glucose.

Favorable examples of the buffers include buffer solutions of phosphates, acetates, carbonates and citrates, etc.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2, etc.); water insoluble lake dyes (e.g., aluminum salts of the aforementioned water soluble edible tar dyes), natural dyes (e.g., β-carotene, chlorophyll, ferric oxide red).

Favorable examples of the sweeteners include sodium saccharin, dipotassium glycyrrhizinate, aspartame and stevia.

The pharmaceutical compositions of the present invention can be manufactured by the common methods in the field of formulation technology, for example, methods listed in the Japanese pharmacopoeia, etc. Specific production methods for formulations are described in detail below.

The content of the compound of the present invention in the pharmaceutical compositions of the present invention varies based on the dosage forms, dosages of the compound of the present invention, etc. For example, the content approximately ranges from about 0.01 to 100 wt % and preferably from 0.1 to 95 wt % relative to the entire amount of the composition.

The dosage of the compound of the present invention depends upon administration subjects, administration routes, target diseases, symptoms, etc. For example, in the case of oral administration in patients with schizophrenia (adults, bodyweight of about 60 kg), generally a single dose ranges from about 0.1 to about 20 mg/kg bodyweight, preferably from about 0.2 to about 10 mg/kg bodyweight, further preferably from about 0.5 to about 10 mg/kg bodyweight, and this dosage is preferably administered once daily or several times daily (e.g., 3 times).

The compound of the present invention may be used in combination with other active ingredients. Examples of the drug that can be used in combination or concomitantly with the compound of the present invention (hereinafter sometimes to be abbreviated as concomitant drug) include the following.

A therapeutic drug for psychotic diseases, particularly schizophrenia, or bipolar disorder, obsessive disorder, major depression, Parkinson's disease, Huntington's disease, Alzheimer's disease, cognitive dysfunction and memory disorders [atypical antipsychotic agents (e.g., clozapine, olanzapine, risperidone, aripiprazole, blonanserin, iloperidone, asenapine, ziprasidone, quetiapine, zotepine etc.), typical antipsychotic agents (e.g., haloperidol, chlorpromazine etc.), selective serotonin reuptake inhibitor (e.g., paroxetine, sertraline, fluvoxamine, fluoxetine etc.), selective serotonin.noradrenaline reuptake inhibitor (e.g., milnacipran, venlafaxine etc.), selective noradrenaline-dopamine reuptake inhibitor (e.g., bupropion etc.), tetracyclic antidepressant (e.g., amoxapine, clomipramine etc.), tricyclic antidepressant (e.g., imipramine, amitriptyline etc.), other antidepressant (e.g., NS-2359, Lu AA21004, DOV21947 etc.), $α_7$ nicotine receptor agonist, $α_7$ nicotine receptor activity modulator, $α_7$ nicotine receptor partial modulator (e.g., SSR-180711, PNU-120596 etc.), PDE1 inhibitor, PDE2 inhibitor, PDE4 inhibitor, PDE5 inhibitor, PDE7 inhibitor, PDE9 inhibitor, other PDE inhibitor, calcium channel inhibitor, NK2 antagonist, NK3 antagonist, muscarine type M1 acetylcholine receptor activity modulator, muscarine type M2 acetylcholine receptor activity modulator, adenosine receptor modulator, muscarine type M4 acetylcholine receptor activity modulator, muscarine type M5 acetylcholine receptor activity modulator, adenosine receptor modulator, glycine transporter 1 inhibitor (e.g., ALX5407, SSR504734 etc.), glutamate enhancer (e.g., ampakine), NMDA-type glutamate receptor modulator, metabolic glutamate receptor modulator (e.g., CDPPB, MPEP etc.), antianxiety drug (benzodiazepine (e.g., diazepam, etizolam etc.), serotonin 5-$HT_{1A}$ agonist (e.g., tandospirone etc.)), hypnotic pills (benzodiazepine (e.g., estazolam, triazolam etc.), non-benzodiazepine (e.g., zolpidem etc.), melatonin receptor agonist (e.g., ramelteon etc.)), β amyloid vaccine, β amyloid degrading enzyme etc., brain function activator (e.g., aniracetam, nicergoline etc.), cannabinoid modulator, cholinesterase inhibitor (e.g., donepezil, rivastigmine, galanthamine), therapeutic drug for Parkinson's disease (e.g., dopamine receptor agonist (L-DOPA, bromocriptine, pergolide, talipexole, pramipexole, cabergoline, amantadine etc.), monoamine oxidase inhibitor (deprenyl, selegiline, remacemide, riluzole etc.), anticholinergic agent (e.g., trihexyphenidyl, biperiden etc.), COMT inhibitor (e.g., entacapone etc.), a therapeutic drug for amyotrophic lateral sclerosis (e.g., riluzole etc., neurotrophic factor etc.), apoptosis inhibitor (e.g., CPI-1189, IDN-6556, CEP-1347 etc.), neuronal differentiation-regeneration promoter (e.g., leteprinim, xaliproden (SR-57746-A), SB-216763 etc.)], and a therapeutic drug for diseases easily associated with schizophrenia [therapeutic drug for diabetes (PPAR acting drug (e.g., agonist, inhibitor, pioglitazone, rosiglitazone, troglitazone), insulin secretagogue (e.g., sulfonylurea drugs, non-sulfonylurea drugs), a glucosidase inhibitor (e.g., acarbose), insulin sensitizer (e.g., PPAR-γ acting drug, PTP-1B inhibitor, DPP-4 inhibitor, 11β-HSD inhibitor), liver gluconeogenesis inhibitor (e.g., glucagon antagonist, metformin), insulin, insulin derivative), antiobesity drug (β-3 agonist, CB1 agonist, neuropeptide Y5 inhibitor, anorexigenic agent (e.g., sibutramine), lipase inhibitor (e.g., orlistat)), a therapeutic drug for hyperlipidemia such as a cholesterol lowering agent and the like (statin (e.g., pravastatin sodium, atrovastatin, simvastatin, rosuvastatin etc.), fibrate (e.g., clofibrate etc.), squalene synthase inhibitor), antihypertensive agent, non-steroidal anti-inflammatory agent (e.g., meloxicam, teoxicam, indomethacin, ibuprofen, celecoxib, rofecoxib, aspirin, indomethacin etc.), disease-modified anti-rheumatic drug (DMARDs), anticytokine agent (TNF inhibitor, MAP kinase inhibitor and the like), steroid drug (e.g., dexamethasone, hexestrol, cortisone acetate etc.), sex hormone or a derivative thereof (e.g., progesterone, estradiol, estradiol benzoate etc.), parathyroid hormone (PTH), calcium receptor antagonist etc.]

The dosage form of concomitant drugs with the compound of the present invention is not particularly limited and is acceptable as long as the compound of the present invention is combined with concomitant drugs at the time of administration. Examples of such dosage forms are as follows (1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug (e.g., administration in the order of the compound of the present invention and then a concomitant drug, or administration in the reversed order). These dosage forms are summarized below and abbreviated as a combination drug of the present invention.

When administering the combination drug of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, dosage forms and methods of administration. For example, when a concomitant drug is administered first, the compound of the present invention can be administered within 1 min to 3 days, preferably within 10 min to 1 day and more preferably within 15 min to 1 hour after the concomitant drug is administered. However, if the compound of the present invention is administered first, a concomitant drug can be administered within 1 min to 1 day, preferably within 10 min to 6 hours and more preferably within 15 min to 1 hour after the compound of the present invention is administered.

If there are no problems with side effects of the concomitant drugs, any dosages can be set. A daily dosage as a concomitant drug depends upon administration subjects, administration routes, target diseases, symptoms, etc. For example, in the case of oral administration in patients with schizophrenia (adults, bodyweight of about 60 kg), a normal once dosage ranges from about 0.1 to about 20 mg/kg bodyweight, preferably from about 0.2 to about 10 mg/kg bodyweight and more preferably from about 0.5 to about 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The combination drug of the present invention exhibits low toxicity. For example, the compound of the present invention or (and) the aforementioned concomitant drug can be combined with a pharmaceutically acceptable carrier according to the known method to prepare a pharmaceutical composition such as tablets (including sugar-coated tablet and film-coated tablet), powders, granules, capsules (including soft capsule), liquids, injections, suppositories, sustained-release preparation, etc. These compositions can be administered safely orally or parenterally.

The pharmaceutically acceptable carriers that may be used for manufacturing the combination drug of the present invention can be the same as those used in the pharmaceutical composition of the present invention as mentioned above.

A combination ratio between the compound of the present invention and a concomitant drug in the combination drug of the present invention can be selected appropriately based on the administration subjects, administration routes and diseases, etc.

The aforementioned concomitant drugs can be used in combination at an appropriate proportion if two or more drugs are combined.

A dosage of the concomitant drug can be selected appropriately based on the dosages used clinically. In addition, a mixing ratio between the compound of the present invention and a concomitant drug can be selected appropriately based on the administration subjects, administration routes, target diseases, symptoms, combinations, etc. For example, if the administration subject is humans, a concomitant drug may be used in an amount ranging from 0.01 to 100 parts by weight relative to 1 part by weight of the compound of the present invention.

For example, the content of the compound of the present invention in the combination drug of the present invention varies with the form of formulations. Generally, it is present in a range from about 0.01 to 99.9 wt %, preferably from about 0.1 to about 50 wt % and more preferably from about 0.5 to about 20 wt % relative to the entire formula.

The content of a concomitant drug in the combination drug of the present invention varies with the drug form of formulations. Generally it is present in a range from about 0.01 to 99.9 wt %, preferably from about 0.1 to about 50 wt % and more preferably from about 0.5 to about 20 wt % relative to the entire formula.

The content of an additive such as carriers in the combination drug of the present invention varies with the drug form of formulations. Generally it is present in a range from about 1 to 99.99 wt % and preferably from about 10 to about 90 wt % relative to the entire formula.

When the compound of the present invention and a concomitant drug are formulated independently, the same contents can be applied.

Since the dosages may fluctuate under various conditions as mentioned above, a dosage less than the dosages may be sufficient or it may be necessary to administer at a dosage exceeding the range.

EXAMPLES

The present invention is explained in detail in the following by referring to Examples, Experimental Examples and Preparation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In the following Examples, the following abbreviations are used.
THF: tetrahydrofuran
DMF: N,N-dimethylformamide
NMP: N-methylpyrrolidone
DMSO: dimethyl sulfoxide
ESI: electrospray ionization method
API: atmospheric chemical ionization method
[M+H]$^+$: molecular ion peak
TFA: trifluoroacetic acid
M: molar concentration
N: normal concentration
WSC: N-(3-dimethylaminopropyl)-N'-ethylcarbodiimide hydrochloride
HOBt: 1-hydroxybenzotriazole monohydrate
$Pd_2(dba)_3$: tris(dibenzylideneacetone)dipalladium(0)
Xantphos: 4,5-bis(diphenylphosphino)-9,9-dimethylxanthene
MCPBA: m-chloroperbenzoic acid
HPLC: high performance liquid chromatography
$^1$H NMR (proton nuclear magnetic resonance spectrum) was measured by Fourier-transform type NMR. For the analysis, ACD/SpecManager (trade name) and the like were used. Very mild peaks showing protons of hydroxyl group, amino group and the like are not described.

MS (mass spectrum) was measured by LC/MS (liquid chromatography mass spectrometer).

As the ionization method, ESI (ElectroSpray Ionization) method, or APCI (Atomospheric Pressure Chemical Ionization) method was used. The data shows Found. Generally, molecular ion peaks are observed. However, when a compound having a tert-butoxycarbonyl group (-Boc) is used, a peak free of a tert-butoxycarbonyl group or a tert-butyl group may be observed as a fragment ion. In addition, when a compound having a hydroxyl group (—OH) is used, a peak free of $H_2O$ may be observed as a fragment ion. In the case of a salt, generally, a molecular ion peak or a fragment ion peak of a free form is observed.

Example 1 and Example 2

1-[2-fluoro-4-(1H-pyrazol-1-yl)phenyl]-5-methoxy-3-(3-methyl-1-phenyl-1H-pyrazol-5-yl)pyridazin-4(1H)-one (Example 1)

5-methoxy-1-[2-methoxy-4-(1H-pyrazol-1-yl)phenyl]-3-(3-methyl-1-phenyl-1H-pyrazol-5-yl)pyridazin-4(1H)-one (Example 2)

A mixture of 3-acetyl-1-[2-fluoro-4-(1H-pyrazol-1-yl)phenyl]-5-methoxypyridazin-4(1H)-one (300 mg), N,N-dimethylacetamide dimethyl acetal (3 mL) and acetonitrile (3 mL) was stirred at 80° C. for 12 hr, and the solvent was evaporated under reduced pressure. The residue was dissolved in acetic acid (5 mL), phenylhydrazine (98.8 mg) was added thereto at room temperature. The reaction mixture was stirred at 80° C. for 3 hr, and the solvent was evaporated under reduced pressure. The mixture was treated with 1M hydrochloric acid, and the residue was extracted with ethyl acetate. The extract was dried over anhydrous magnesium sulfate, and the solvent was evaporated under reduced pressure. The residue was purified by silica gel column chromatography (ethyl acetate/methanol) to give a mixture containing 1-[2-fluoro-4-(1H-pyrazol-1-yl)phenyl]-5-methoxy-3-(3-methyl-1-phenyl-1H-pyrazol-5-yl)pyridazin-4(1H)-one (69 mg) and 5-methoxy-1-[2-methoxy-4-(1H-pyrazol-1-yl)phenyl]-3-(3-methyl-1-phenyl-1H-pyrazol-5-yl)pyridazin-4(1H)-one. The obtained mixture was purified by preparative HPLC to give 5-methoxy-1-[2-methoxy-4-(1H-pyrazol-1-yl)phenyl]-3-(3-methyl-1-phenyl-1H-pyrazol-5-yl)pyridazin-4(1H)-one (28 mg).

1-[2-fluoro-4-(1H-pyrazol-1-yl)phenyl]-5-methoxy-3-(3-methyl-1-phenyl-1H-pyrazol-5-yl)pyridazin-4(1H)-one $^1$H NMR (300 MHz, DMSO-$d_6$) δ 2.29 (3H, s), 3.78 (3H, s), 6.59-6.66 (1H, m), 6.79 (1H, s), 7.08-7.21 (1H, m), 7.25-7.49 (5H, m), 7.74 (1H, d, J=8.7 Hz), 7.83 (1H, d, J=1.5 Hz), 7.91-8.04 (1H, m), 8.52 (1H, d, J=1.9 Hz), 8.66 (1H, d, J=2.7 Hz).

5-methoxy-1-[2-methoxy-4-(1H-pyrazol-1-yl)phenyl]-3-(3-methyl-1-phenyl-1H-pyrazol-5-yl)pyridazin-4(1H)-one $^1$H NMR (300 MHz, DMSO-$d_6$) δ2.29 (3H, s), 3.76 (3H, s), 3.91 (3H, s), 6.60 (1H, s), 6.75 (1H, s), 6.93 (1H, d, J=8.7 Hz), 7.20-7.49 (6H, m), 7.64 (1H, d, J=1.9 Hz), 7.80 (1H, s), 8.38 (1H, s), 8.66 (1H, d, J=2.7 Hz).

Example 3

3-[1-(3-chloro-2-fluorophenyl)-1H-pyrazol-5-yl]-1-[2-fluoro-4-(1H-pyrazol-1-yl)phenyl]-5-methoxypyridazin-4(1H)-one A) 3-[3-(dimethylamino)prop-2-enoyl]-1-[2-fluoro-4-(1H-pyrazol-1-yl)phenyl]-5-methoxypyridazin-4(1H)-one A mixture of 3-acetyl-1-[2-fluoro-4-(1H-pyrazol-1-yl)phenyl]-5-methoxypyridazin-4(1H)-one (600 mg), N,N-dimethylformamide dimethyl acetal (3 mL) and acetonitrile (3 mL) was stirred at 80° C. for 12 hr, allowed to be cooled to room temperature, and stirred for 12 hr. The precipitate was collected by filtration, and washed with diisopropyl ether to give the title compound (600 mg).
$^1$H NMR (300 MHz, DMSO-$d_6$) δ 2.82 (3H, s), 3.09 (3H, s), 3.79 (3H, s), 5.25 (1H, brs), 6.64 (1H, dd, J=2.5, 1.8 Hz), 7.51 (1H, brs), 7.79-7.95 (3H, m), 7.99-8.10 (1H, m), 8.50 (1H, d, J=1.8 Hz), 8.68 (1H, d, J=2.5 Hz).

B) 3-[1-(3-chloro-2-fluorophenyl)-1H-pyrazol-5-yl]-1-[2-fluoro-4-(1H-pyrazol-1-yl)phenyl]-5-methoxypyridazin-4 (H)-one To a solution of 3-[3-(dimethylamino)prop-2-enoyl]-1-[2-fluoro-4-(1H-pyrazol-1-yl)phenyl]-5-methoxypyridazin-4(1H)-one (200 mg) in TFA/ethanol (5/95, 8 mL) was added (3-chloro-2-fluorophenyl)hydrazine hydrochloride (98.8 mg) under ice-cooling. The reaction mixture was stirred at room temperature for 3 hr, water was added thereto, and the mixture was extracted with ethyl acetate. The extract was dried over anhydrous magnesium sulfate, and the solvent was evaporated under reduced pressure. The residue was purified by silica gel column chromatography (ethyl acetate/methanol) to give the title compound (97 mg).
$^1$H NMR (300 MHz, DMSO-$d_6$) δ 3.80 (3H, s), 6.57-6.71 (1H, m), 7.12-7.22 (1H, m), 7.23-7.32 (1H, m), 7.38-7.49 (2H, m), 7.55-7.69 (1H, m), 7.72-7.81 (1H, m), 7.81-8.01 (3H, m), 8.50 (1H, d, J=1.9 Hz), 8.67 (1H, d, J=2.6 Hz)

Example 4

3-[1-(5-chloro-2-fluorophenyl)-1H-pyrazol-5-yl]-1-[2-fluoro-4-(1H-pyrazol-1-yl)phenyl]-5-methoxypyridazin-4 (H)-one To a solution of 3-[3-(dimethylamino)prop-2-enoyl]-1-[2-fluoro-4-(1H-pyrazol-1-yl)phenyl]-5-methoxypyridazin-4 (H)-one (200 mg) in TFA/ethanol (5/95, 8 mL) was added (5-chloro-2-fluorophenyl)hydrazine hydrochloride (88.8 mg) under ice-cooling. The reaction mixture was stirred at room temperature for 3 hr, water was added thereto, and the mixture was extracted with ethyl acetate. The extract was dried over anhydrous magnesium sulfate, and the solvent was evaporated under reduced pressure. The residue was purified by silica gel column chromatography (ethyl acetate/methanol) to give the title compound (98 mg).
$^1$H NMR (300 MHz, DMSO-$d_6$) δ 3.80 (3H, s), 6.52-6.71 (1H, m), 7.10-7.26 (1H, m), 7.27-7.41 (2H, m), 7.45-7.54 (1H, m), 7.60-7.68 (1H, m), 7.74-7.81 (1H, m), 7.82-7.90 (2H, m), 7.92-8.00 (1H, m), 8.51 (1H, d, J=1.9 Hz), 8.67 (1H, d, J=2.6 Hz).

Example 5

1-[2-fluoro-4-(1H-pyrazol-1-yl)phenyl]-5-methoxy-3-{1-[3-(trifluoromethyl)phenyl]-1H-pyrazol-5-yl}pyridazin-4 (H)-one To a solution of 3-[3-(dimethylamino)prop-2-enoyl]-1-[2-fluoro-4-(1H-pyrazol-1-yl)phenyl]-5-methoxypyridazin-4 (H)-one (200 mg) in TFA/EtOH (5/95, 8 mL) was added [3-(trifluoromethyl)phenyl]hydrazine (96.5 mg) under ice-cooling. The reaction mixture was stirred at room temperature for 3 hr, water was added thereto, and the mixture was extracted with ethyl acetate. The extract was dried over anhydrous magnesium sulfate, and the solvent was evaporated under reduced pressure. The residue was purified by silica gel column chromatography (ethyl acetate/methanol) to give the title compound (185 mg).

$^1$H NMR (300 MHz, DMSO-$d_6$) δ 3.79 (3H, s), 6.63 (1H, s), 7.11 (1H, s), 7.30-7.44 (1H, m), 7.56-7.82 (5H, m), 7.80-7.92 (2H, m), 7.93-8.04 (1H, m), 8.56 (1H, s), 8.66 (1H, d, J=2.3 Hz).

Example 6

1-[2-fluoro-4-(1H-pyrazol-1-yl)phenyl]-5-methoxy-3-[1-(2,2,2-trifluoroethyl)-1H-pyrazol-5-yl]pyridazin-4(1H)-one To a suspension of 3-[3-(dimethylamino)prop-2-enoyl]-5-methoxy-1-[2-fluoro-4-(1H-pyrazol-1-yl)phenyl]pyridazin-4(1H)-one (200 mg) in ethanol (2.0 mL) was added dropwise a solution of 2,2,2-trifluoroethylhydrazine (0.0483 mL) and TFA (0.2 mL) in ethanol (2.0 mL), and the mixture was stirred at room temperature for 48 hr. The reaction mixture was concentrated under reduced pressure, and the residue was purified by silica gel column chromatography (ethyl acetate/hexane) to give the title compound (170 mg).

$^1$H NMR (300 MHz, CDCl$_3$) δ 3.86 (3H, s), 5.36 (2H, q, J=8.9 Hz), 6.65 (1H, d, J=2.6 Hz), 7.17 (1H, d, J=1.9 Hz), 7.71 (1H, d, J=1.9 Hz), 7.86 (1H, d, J=1.5 Hz), 7.89-7.99 (2H, m), 8.08 (1H, d, J=1.9 Hz), 8.64 (1H, s), 8.70 (1H, d, J=2.6 Hz)

mp 185-187° C.

Anal. Calcd for C$_{19}$H$_{14}$F$_4$N$_6$O$_2$: C, 52.54; H, 3.25; N, 19.35. Found: C, 52.49; H, 3.25; N, 19.32.

Example 7

1-[2-fluoro-4-(1H-pyrazol-1-yl)phenyl]-5-methoxy-3-{1-[3-(trifluoromethoxy)phenyl]-1H-pyrazol-5-yl}pyridazin-4(1H)-one A) [3-(trifluoromethoxy)phenyl]hydrazine hydrochloride 3-(Trifluoromethoxy)aniline (3.68 ml) was dissolved in 6 M hydrochloric acid (71 ml), and an aqueous solution (4.7 ml) of sodium nitrite (2.08 g) was added dropwise over 20 min at −5° C. Tin (II) chloride (1.954 ml) was dissolved in 6 M hydrochloric acid (25 ml), and the solution was cooled to −5° C., and added quickly to the above-mentioned reaction mixture at −5° C. The mixture was stirred at −5° C. for 2 hr, and the precipitated solid was collected by filtration, washed with 0.1M hydrochloric acid, and dried under reduced pressure to give the title compound (2.72 g).

$^1$H NMR (300 MHz, CDCl$_3$) δ 6.81-7.03 (3H, m), 7.41 (1H, t, J=8.3 Hz), 8.64 (1H, br. s.), 10.35 (2H, br. s.)

B) 1-[2-fluoro-4-(1H-pyrazol-1-yl)phenyl]-5-methoxy-3-{1-[3-(trifluoromethoxy)phenyl]-1H-pyrazol-5-yl}pyridazin-4(1H)-one To a suspension of 3-[3-(dimethylamino)prop-2-enoyl]-5-methoxy-1-[2-fluoro-4-(1H-pyrazol-1-yl)phenyl]pyridazin-4(1H)-one (200 mg) in ethanol (2.0 mL) was added dropwise a solution of [3-(trifluoromethoxy)phenyl]hydrazine hydrochloride (139 mg) and TFA (0.2 mL) in ethanol (2.0 mL), and the mixture was so stirred at room temperature for 24 hr. To the reaction mixture was added an ethanol solution (0.3 ml) of [3-(trifluoromethoxy)phenyl]hydrazine hydrochloride (16.7 mg), and the mixture was stirred at room temperature for 24 hr. The precipitated solid was collected by filtration. The mother liquor was concentrated, and the precipitated solid was collected by filtration. The solid was combined with the previously obtained solid, and recrystallized from acetone/water to give the title compound (96.1 mg).

$^1$H NMR (300 MHz, CDCl$_3$) δ 3.79 (3H, s), 6.64 (1H, d, J=2.6 Hz), 7.03 (1H, d, J=1.9 Hz), 7.27-7.49 (4H, m), 7.57 (1H, t, J=8.1 Hz), 7.74-7.88 (3H, m), 7.99 (1H, dd, J=12.1, 2.3 Hz), 8.57 (1H, d, J=1.9 Hz), 8.66 (1H, d, J=2.6 Hz)

mp 148-150° C.

Anal. Calcd for C$_{24}$H$_{16}$F$_4$N$_6$O$_3$·0.5H$_2$O: C, 55.28; H, 3.29; N, 16.11. Found: C, 55.25; H, 3.07; N, 16.05.

Example 8

5-methoxy-1-[2-methoxy-4-(1H-pyrazol-1-yl)phenyl]-3-{1-[3-(trifluoromethyl)phenyl]-1H-pyrazol-5-yl}pyridazin-4(1H)-one A) 3-[3-(dimethylamino)prop-2-enoyl]-5-methoxy-1-[2-methoxy-4-(1H-pyrazol-1-yl)phenyl]pyridazin-4(1H)-one A mixture of 3-acetyl-5-methoxy-1-[2-methoxy-4-(1H-pyrazol-1-yl)phenyl]pyridazin-4(1H)-one (264 mg), N,N-dimethylformamide dimethyl acetal (1.5 mL) and acetonitrile (1.5 mL) was heated under reflux for 3 hr. The reaction mixture was concentrated under reduced pressure, and the residue was crystallized from ethanol to give the title compound (274 mg).

$^1$H NMR (300 MHz, CDCl$_3$) δ 2.90 (3H, s), 3.12 (3H, s), 3.89 (3H, s), 3.97 (3H, s), 5.89 (1H, brs), 6.52 (1H, dd, J=2.6, 1.9 Hz), 7.26 (1H, dd, J=8.3, 2.3 Hz), 7.59 (1H, d, J=1.9 Hz), 7.63 (1H, d, J=8.7 Hz), 7.76 (1H, d, J=1.9 Hz), 7.79 (1H, brs), 7.82 (1H, s), 7.98 (1H, d, J=2.3 Hz).

B) 5-methoxy-1-[2-methoxy-4-(1H-pyrazol-1-yl)phenyl]-3-{1-[3-(trifluoromethyl)phenyl]-1H-pyrazol-5-yl}pyridazin-4(1H)-one To a suspension of 3-[3-(dimethylamino)prop-2-enoyl]-5-methoxy-1-[2-methoxy-4-(1H-pyrazol-1-yl)phenyl]pyridazin-4(1H)-one (136 mg) in ethanol (1.5 mL) was added dropwise a solution of 3-(trifluoromethyl)phenylhydrazine (0.049 mL) and TFA (0.15 mL) in ethanol (1.5 mL), and the mixture was stirred at room temperature for 3 hr. The reaction mixture was concentrated under reduced pressure, and the residue was purified by silica gel column chromatography (NH, ethyl acetate), and recrystallized from ethanol/water to give the title compound (123 mg).

mp 215-217° C.

¹H NMR (300 MHz, CDCl₃) δ 3.89 (3H, s), 3.93 (3H, s), 6.53 (1H, dd, J=2.6, 1.9 Hz), 6.62 (1H, d, J=8.7 Hz), 7.03 (1H, dd, J=8.7, 2.3 Hz), 7.30 (1H, d, J=1.9 Hz), 7.48-7.53 (2H, m), 7.57-7.62 (2H, m), 7.67-7.68 (1H, m), 7.76 (1H, d, J=1.5 Hz), 7.80 (1H, d, J=1.9 Hz), 7.82 (1H, s), 7.93 (1H, d, J=2.3 Hz).
Anal. Calcd for $C_{25}H_{19}F_3N_6O_3$: C, 59.06; H, 3.77; N, 16.53. Found: C, 58.97; H, 3.85; N, 16.40.

Example 9

3-[1-(3-chlorophenyl)-1H-pyrazol-5-yl]-5-methoxy-1-[2-methoxy-4-(1H-pyrazol-1-yl)phenyl]pyridazin-4(1H)-one To a suspension of 3-[3-(dimethylamino)prop-2-enoyl]-5-methoxy-1-[2-methoxy-4-(1H-pyrazol-1-yl)phenyl]pyridazin-4(1H)-one (136 mg) in ethanol (1.5 mL) was added dropwise a solution of 3-chlorophenylhydrazine hydrochloride (67.7 mg) and TFA (0.15 mL) in ethanol (1.5 mL), and the mixture was stirred at room temperature for 5 hr. The reaction mixture was concentrated under reduced pressure, and the residue was purified by silica gel column chromatography (NH, ethyl acetate), crystallized from ethyl acetate, and recrystallized from ethanol/water to give the title compound (68.0 mg).
mp 167-168° C.
¹H NMR (CDCl₃) δ 3.90 (3H, s), 3.95 (3H, s), 6.53 (1H, dd, J=2.6, 1.9 Hz), 6.68 (1H, d, J=8.7 Hz), 7.08 (1H, dd, J=8.7, 2.3 Hz), 7.27-7.36 (4H, m), 7.44-7.45 (1H, m), 7.53 (1H, d, J=2.3 Hz), 7.76 (1H, d, J=1.9 Hz), 7.77 (1H, d, J=1.9 Hz), 7.84 (1H, s), 7.96 (1H, d, J=2.6 Hz).
Anal. Calcd for $C_{24}H_{19}ClN_6O_3$: C, 60.70; H, 4.03; N, 17.70. Found: C, 60.73; H, 4.08; N, 17.58.

Example 10

1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one A) 4-bromo-2-(tert-butoxy)-1-nitrobenzene To a solution of 4-bromo-2-fluoro-1-nitrobenzene (25.2 g) in THF (250 mL) was added potassium tert-butoxide (25.3 g) portionwise at 0° C., and the mixture was stirred at 0° C. for 30 min. The reaction mixture was poured into water, and the mixture was extracted with ethyl acetate. The extract was washed with water and saturated brine, dried over anhydrous magnesium sulfate, and concentrated under reduced pressure. The residue was purified by silica gel column chromatography (hexane/ethyl acetate) to give the title compound (28.6 g).
¹H NMR (300 MHz, CDCl₃) δ 1.44 (9H, s), 7.26 (1H, dd, J=8.7, 2.3 Hz), 7.38 (1H, d, J=2.3 Hz), 7.62 (1H, d, J=8.7 Hz).

B) 1-(3-tert-butoxy-4-nitrophenyl)-3,4-difluoro-1H-pyrrole

A suspension of 4-bromo-2-(tert-butoxy)-1-nitrobenzene (13.7 g), 3,3,4,4-tetrafluoropyrrolidine hydrochloride (9.87 g), Pd₂(dba)₃ (0.916 g), Xantphos (2.31 g) and sodium tert-butoxide (19.2 g) in 1,4-dioxane (150 mL) was stirred at 90° C. for 4 hr under an argon atmosphere. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (NH, hexane/ethyl acetate), and recrystallized from hexane/ethyl acetate to give the title compound (8.35 g).
¹H NMR (300 MHZ, CDCl₃) δ 1.47 (9H, s), 6.72-6.82 (2H, m), 7.00 (1H, dd, J=8.7, 2.6 Hz), 7.04 (1H, d, J=2.6 Hz), 7.88 (1H, d, J=8.7 Hz).

C) 5-(3,4-difluoro-1H-pyrrol-1-yl)-2-nitrophenol

A mixture of 1-(3-tert-butoxy-4-nitrophenyl)-3,4-difluoro-1H-pyrrole (8.30 g), TFA (30 mL) and THF (60 mL) was heated under reflux for 3 hr. The reaction mixture was concentrated under reduced pressure, and the residue was washed with hexane/ethyl acetate (10/1) to give the title compound (6.43 g).
¹H NMR (300 MHz, CDCl₃) δ 6.80-6.91 (3H, m), 6.98 (1H, d, J=2.6 Hz), 8.18 (1H, d, J=9.4 Hz), 10.85 (1H, s).

D) 1-[3-(benzyloxy)-4-nitrophenyl]-3,4-difluoro-1H-pyrrole

A suspension of 5-(3,4-difluoro-1H-pyrrol-1-yl)-2-nitrophenol (6.39 g), benzyl bromide (3.48 mL) and potassium carbonate (5.51 g) in DMF (60 mL) was stirred at room temperature overnight. The reaction mixture was poured into water, and the mixture was extracted with ethyl acetate. The extract was washed with water and saturated brine, dried over anhydrous magnesium sulfate, and concentrated under reduced pressure. The residue was recrystallized from hexane/ethyl acetate to give the title compound (8.57 g).
¹H NMR (300 MHz, CDCl₃) δ 5.30 (2H, s), 6.67-6.77 (2H, m), 6.88-6.92 (2H, m), 7.33-7.51 (5H, m), 8.02 (1H, d, J=8.3 Hz).

E) 2-(benzyloxy)-4-(3,4-difluoro-1H-pyrrol-1-yl)aniline

To a mixture of zinc (33.7 g), THF (40 mL) and acetic acid (80 mL) was added dropwise a mixture of 1-[3-(benzyloxy)-4-nitrophenyl]-3,4-difluoro-1H-pyrrole (8.52 g), THF (80 mL) and acetic acid (40 mL) at 0° C., and the mixture was stirred at 0° C. for 15 min. The reaction mixture was filtered, and the filtrate was concentrated under reduced pressure. The residue was purified by silica gel column chromatography (NH, hexane/ethyl acetate), and recrystallized from hexane/ethyl acetate to give the title compound (7.53 g).
¹H NMR (300 MHz, CDCl₃) δ 3.86 (2H, s), 5.10 (2H, s), 6.50-6.60 (2H, m), 6.69-6.76 (3H, m), 7.33-7.46 (5H, m).

F) methyl 2-{[2-(benzyloxy)-4-(3,4-difluoro-1H-pyrrol-1-yl)phenyl]hydrazono}-4-methoxy-3-oxobutanoate To a mixture of 2-(benzyloxy)-4-(3,4-difluoro-1H-pyrrol-1-yl)aniline (7.51 g) and 6M hydrochloric acid (50 mL) was added dropwise a solution of sodium nitrite (3.45 g) in water (10 mL) at 0° C., and the mixture was stirred for 15 min. The reaction mixture was added to a suspension (cooled to 0° C.) of 4-methyl methoxyacetoacetate (3.24 mL) and sodium acetate (24.6 g) in methanol (50 mL). The reaction mixture was stirred for 15 min, and poured into water, and the mixture was extracted with ethyl acetate. The extract was washed with saturated aqueous sodium hydrogen carbonate solution and saturated brine, dried over anhydrous magnesium sulfate, and concentrated under reduced pressure. The residue was washed with hexane/ethyl acetate, and recrystallized from hexane/THF to give the title compound (4.87 g).

¹H NMR (300 MHz, CDCl₃) δ 3.51 (3H, s), 3.90 (3H, s), 4.68 (2H, s), 5.27 (2H, s), 6.59-6.69 (2H, m), 6.87 (1H, d, J=2.3 Hz), 6.94 (1H, dd, J=8.7, 2.3 Hz), 7.34-7.52 (5H, m), 7.61 (1H, d, J=8.7 Hz), 13.27 (1H, s).

G) methyl 1-[2-(benzyloxy)-4-(3,4-difluoro-1H-pyrrol-1-yl)phenyl]-5-methoxy-4-oxo-1,4-dihydropyridazine-3-carboxylate A mixture of methyl 2-{[2-(benzyloxy)-4-(3,4-difluoro-1H-pyrrol-1-yl)phenyl]hydrazono}-4-methoxy-3-oxobutanoate (4.85 g) and N,N-dimethylformamide dimethyl acetal (100 mL) was heated under reflux for 3 hr. The mixture was allowed to be cooled to room temperature, and the precipitate was collected by filtration, and recrystallized from methanol to give the title compound (4.57 g).
¹H NMR (300 MHz, CDCl₃) δ 3.64 (3H, s), 3.97 (3H, s), 5.17 (2H, s), 6.69-6.79 (2H, m), 6.99-7.03 (2H, m), 7.32-7.43 (5H, m), 7.59-7.62 (1H, m), 7.80 (1H, s).

H) 1-[2-(benzyloxy)-4-(3,4-difluoro-1H-pyrrol-1-yl)phenyl]-5-methoxy-4-oxo-1,4-dihydropyridazine-3-carboxylic acid A mixture of methyl 1-[2-(benzyloxy)-4-(3,4-difluoro-1H-pyrrol-1-yl)phenyl]-5-methoxy-4-oxo-1,4-dihydropyridazine-3-carboxylate (4.54 g), 1M aqueous sodium hydroxide solution (15 mL), THF (30 mL) and methanol (30 mL) was stirred at room temperature for 30 min. The reaction mixture was neutralized with 1M hydrochloric acid, and the precipitate was collected by filtration, and washed with water to give the title compound (0.5 THF solvate, 4.70 g).
¹H NMR (300 MHz, DMSO-d₆) δ3.78 (3H, s), 5.32 (2H, s), 7.31-7.45 (6H, m), 7.59 (1H, d, J=2.3 Hz), 7.69-7.71 (3H, m), 8.89 (1H, s), 15.18 (1H, brs).

I) 1-[2-(benzyloxy)-4-(3,4-difluoro-1H-pyrrol-1-yl)phenyl]-N,5-dimethoxy-N-methyl-4-oxo-1,4-dihydropyridazine-3-carboxamide A suspension of 1-[2-(benzyloxy)-4-(3,4-difluoro-1H-pyrrol-1-yl)phenyl]-5-methoxy-4-oxo-1,4-dihydropyridazine-3-carboxylic acid (0.5 THF solvate, 4.67 g), N,O-dimethylhydroxylamine hydrochloride (1.11 g), WSC (2.19 g), HOBt (1.54 g) and triethylamine (1.59 mL) in DMF (75 mL) was stirred at room temperature for 6 hr. The reaction mixture was poured into water, and the mixture was extracted with ethyl acetate. The extract was washed with water and saturated brine, dried over anhydrous magnesium sulfate, and concentrated under reduced pressure. The residue was purified by silica gel column chromatography (NH, THF), and recrystallized from hexane/THF to give the title compound (4.51 g).
¹H NMR (300 MHz, CDCl₃) δ 3.38 (3H, s), 3.62 (3H, s), 3.67 (3H, s), 5.17 (2H, s), 6.69-6.79 (2H, m), 6.97-7.01 (2H, m), 7.32-7.44 (5H, m), 7.59-7.64 (1H, m), 7.86 (1H, s).

J) 3-acetyl-1-[2-(benzyloxy)-4-(3,4-difluoro-1H-pyrrol-1-yl)phenyl]-5-methoxypyridazin-4(1H)-one To a solution of 1-[2-(benzyloxy)-4-(3,4-difluoro-1H-pyrrol-1-yl)phenyl]-N,5-dimethoxy-N-methyl-4-oxo-, 4-dihydropyridazine-3-carboxamide (4.47 g) in THF (270 mL) was added dropwise 1M methylmagnesium bromide THF solution (27 mL) at −78° C., and the mixture was stirred for 15 min. To the reaction mixture was added 1M hydrochloric acid, and the mixture was extracted with ethyl acetate. The extract was washed with water and saturated brine, dried over anhydrous magnesium sulfate, and concentrated under reduced pressure. The residue was washed with THF, and recrystallized from methanol to give the title compound (3.75 g).
¹H NMR (300 MHz, CDCl₃) δ 2.68 (3H, s), 3.63 (3H, s), 5.18 (2H, s), 6.71-6.81 (2H, m), 7.00-7.04 (2H, m), 7.32-7.44 (5H, m), 7.59-7.62 (1H, m), 7.80 (1H, s).

K) 1-[2-(benzyloxy)-4-(3,4-difluoro-1H-pyrrol-1-yl)phenyl]-3-[3-(dimethylamino)prop-2-enoyl]-5-methoxypyridazin-4(1H)-one A mixture of 3-acetyl-1-[2-(benzyloxy)-4-(3,4-difluoro-1H-pyrrol-1-yl)phenyl]-5-methoxypyridazin-4(1H)-one (3.70 g), N,N-dimethylformamide dimethyl acetal (40 mL) and acetonitrile (40 mL) was heated under reflux for 6 hr. The reaction mixture was concentrated under reduced pressure, and the residue was crystallized from ethanol to give the title compound (3.85 g).
¹H NMR (300 MHz, DMSO-d₆) δ 2.78 (3H, brs), 3.05 (3H, brs), 3.65 (3H, s), 5.26 (1H, brs), 5.31 (2H, s), 7.30-7.47 (6H, m), 7.54 (1H, d, J=2.3 Hz), 7.61 (1H, d, J=8.7 Hz), 7.66 (2H, d, J=1.5 Hz), 8.40 (1H, s).

L) 1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one A solution of 1-[2-(benzyloxy)-4-(3,4-difluoro-1H-pyrrol-1-yl)phenyl]-3-[3-(dimethylamino)prop-2-enoyl]-5-methoxypyridazin-4(1H)-one (3.80 g) and phenylhydrazine (1.48 mL) in acetic acid (30 mL) was heated under reflux for 2 hr. The reaction mixture was concentrated under reduced pressure, and the residue was purified by silica gel column chromatography (NH, ethyl acetate), crystallized from hexane/ethyl acetate, and recrystallized from dimethylsulfoxide/ethanol to give the title compound (3.29 g).
mp 221-223° C.
¹H NMR (300 MHz, CDCl₃) δ 3.57 (3H, s), 5.10 (2H, s), 6.31 (1H, d, J=8.7 Hz), 6.65-6.75 (3H, m), 6.92 (1H, d, J=2.3 Hz), 7.27-7.46 (11H, m), 7.78 (1H, d, J=2.3 Hz), 7.88 (1H, s).
Anal. Calcd for $C_{31}H_{23}F_2N_5O_3$: C, 67.51; H, 4.20; N, 12.70. Found: C, 67.48; H, 4.27; N, 12.62.

Example 11

1-[4-(3,4-difluoro-1H-pyrrol-1-yl)-2-hydroxyphenyl]-5-methoxy-3-(1-phenyl-1H-pyrazol-5-yl)pyridazin-4(1H)-one A suspension of 1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one (3.20 g) and 10% palladium on carbon (containing water (50%), 3.20 g) in acetic acid (100 mL) was stirred at room temperature for 3 hr under a hydrogen atmosphere. The palladium on carbon was removed by filtration, and the filtrate was concentrated under reduced pressure. The residue was purified by SFC (column: CHIRALPAK ADH (trade name), 20 mmID×250 mL, manufactured by DAICEL CHEMICAL INDUSTRIES, LTD., mobile phase: carbon dioxide/2-propanol/acetonitrile=700/150/150 (v/v/v)), and the obtained fraction was concentrated under reduced pressure. The residue was recrystallized from acetone to give the title compound (1.24 g).
mp 241-243° C.

¹H NMR (300 MHz, DMSO-d₆) δ 3.75 (3H, s), 6.80 (1H, d, J=8.7 Hz), 6.90-6.99 (2H, m), 7.02 (1H, d, J=2.3 Hz), 7.29-7.49 (7H, m), 7.78 (1H, d, J=1.9 Hz), 8.35 (1H, s), 10.90 (1H, brs).

Anal. Calcd for $C_{24}H_{17}F_2N_5O_3 \cdot 0.5C_3H_4O$: C, 62.45; H, 4.11; N, 14.28. Found: C, 62.33; H, 4.06; N, 14.39.

Example 12

1-[4-(3,4-difluoro-1H-pyrrol-1-yl)-2-methoxyphenyl]-5-methoxy-3-(1-phenyl-1H-pyrazol-5-yl)pyridazin-4(1H)-one A suspension of 1-[4-(3,4-difluoro-1H-pyrrol-1-yl)-2-hydroxyphenyl]-5-methoxy-3-(1-phenyl-1H-pyrazol-5-yl)pyridazin-4(1H)-one (231 mg), iodomethane (0.0375 mL) and potassium carbonate (138 mg) in DMF (2.5 mL) was stirred at room temperature overnight. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (NH, THF), and recrystallized from methanol/water to give the title compound (232 mg).

mp 206-207° C.
¹H NMR (300 MHz, CDCl₃) δ 3.89 (6H, s), 6.36 (1H, d, J=8.7 Hz), 6.65-6.77 (3H, m), 6.81 (1H, d, J=2.3 Hz), 7.25 (1H, d, J=1.9 Hz), 7.35-7.46 (5H, m), 7.77 (1H, d, J=1.9 Hz), 7.81 (1H, s).
Anal. Calcd for $C_{25}H_{19}F_2N_5O_3$: C, 63.15; H, 4.03; N, 14.73. Found: C, 62.96; H, 3.98; N, 14.66.

Example 13

1-[2-(difluoromethoxy)-4-(3,4-difluoro-1H-pyrrol-1-yl)phenyl]-5-methoxy-3-(1-phenyl-1H-pyrazol-5-yl)pyridazin-4(1H)-one A mixture of 1-[4-(3,4-difluoro-1H-pyrrol-1-yl)-2-hydroxyphenyl]-5-methoxy-3-(1-phenyl-1H-pyrazol-5-yl)pyridazin-4(1H)-one (231 mg), sodium chlorodifluoroacetate (152 mg), potassium carbonate (104 mg), DMF (2.5 mL) and water (0.5 mL) was heated under reflux overnight. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (NH, ethyl acetate), and crystallized from hexane/ethyl acetate to give the title compound (193 mg).

mp 168-170° C.
¹H NMR (300 MHz, CDCl₃) δ 3.89 (3H, s), 6.41 (1H, t, J=72.0 Hz), 6.56 (1H, d, J=8.7 Hz), 6.69-6.79 (2H, m), 6.99 (1H, dd, J=8.7, 2.6 Hz), 7.12 (1H, d, J=2.6 Hz), 7.25 (1H, d, J=1.9 Hz), 7.34-7.46 (5H, m), 7.74 (1H, s), 7.78 (1H, d, J=1.9 Hz).
Anal. Calcd for $C_{25}H_{17}F_4N_5O_3$: C, 58.71; H, 3.35; N, 13.69. Found: C, 58.68; H, 3.41; N, 13.55.

Example 14

1-[4-(3,4-difluoro-1H-pyrrol-1-yl)-2-(2,2,2-trifluoroethoxy)phenyl]-5-methoxy-3-(1-phenyl-1H-pyrazol-5-yl)pyridazin-4(1H)-one A suspension of 1-[4-(3,4-difluoro-1H-pyrrol-1-yl)-2-hydroxyphenyl]-5-methoxy-3-(1-phenyl-1H-pyrazol-5-yl)pyridazin-4(1H)-one (138 mg), 2,2,2-trifluoroethyl trifluoromethanesulfonate (104 mg) and potassium carbonate (82 mg) in DMF (1.5 mL) was stirred at room temperature for 30 min. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (NH, THF), and crystallized from methanol to give the title compound (131 mg).

mp 220-222° C.
¹H NMR (300 MHz, CDCl₃) δ 3.86 (3H, s), 4.41 (2H, q, J=7.9 Hz), 6.37-6.41 (1H, m), 6.67-6.80 (4H, m), 7.28 (1H, d, J=1.9 Hz), 7.35-7.47 (5H, m), 7.78 (1H, d, J=1.9 Hz), 7.83 (1H, s).
Anal. Calcd for $C_{26}H_{18}F_5N_5O_3$: C, 57.46; H, 3.34; N, 12.89. Found: C, 57.38; H, 3.38; N, 12.83.

Example 15

5-methoxy-1-[2-methoxy-4-(3,3,4,4-tetrafluoropyrrolidin-1-yl)phenyl]-3-(1-phenyl-1H-pyrazol-5-yl)pyridazin-4(1H)-one A) 3-acetyl-1-(4-iodo-2-methoxyphenyl)-5-methoxypyridazin-4(1H)-one To a solution of 1-(4-iodo-2-methoxyphenyl)-N,5-dimethoxy-N-methyl-4-oxo-1,4-dihydropyridazine-3-carboxamide (8.90 g) in THF (150 mL) was added dropwise 1M methylmagnesium bromide THF solution (30 mL) at −78° C., and the mixture was stirred for 20 min. To the reaction mixture was added 1M hydrochloric acid, and the mixture was extracted with ethyl acetate. The extract was washed with water and saturated brine, dried over anhydrous magnesium sulfate, and concentrated under reduced pressure. The residue was washed with ethyl acetate, and recrystallized from methanol/water to give the title compound (5.12 g).

¹H NMR (300 MHz, CDCl₃) δ 2.66 (3H, s), 3.87 (3H, s), 3.90 (3H, s), 7.21 (1H, d, J=8.3 Hz), 7.40 (1H, d, J=1.9 Hz), 7.47 (1H, dd, J=8.3, 1.9 Hz), 7.71 (1H, s).

B) 1-(4-iodo-2-methoxyphenyl)-5-methoxy-3-(1-phenyl-1H-pyrazol-5-yl)pyridazin-4(1H)-one A mixture of 3-acetyl-1-(4-iodo-2-methoxyphenyl)-5-methoxypyridazin-4(1H)-one (2.00 g), N,N-dimethylformamide dimethyl acetal (10 mL) and acetonitrile (10 mL) was heated under reflux for 8 hr. The mixture was allowed to be cooled to room temperature, and concentrated under reduced pressure.

To a solution of the obtained residue in ethanol (20 mL) was added dropwise a solution of phenylhydrazine (0.541 mL) and TFA (0.743 mL) in ethanol (5 mL) at 0° C., and the mixture was stirred at room temperature for 3 hr. The reaction mixture was concentrated under reduced pressure, and the residue was purified by silica gel column chromatography (ethyl acetate), and recrystallized from ethanol/water to give the title compound (1.36 g).

¹H NMR (300 MHz, CDCl₃) δ 3.84 (3H, s), 3.88 (3H, s), 5.98 (1H, d, J=8.3 Hz), 7.13 (1H, dd, J=8.3, 1.9 Hz), 7.25-7.28 (2H, m), 7.34-7.45 (5H, m), 7.77 (1H, d, J=1.9 Hz), 7.79 (1H, s).

C) 5-methoxy-1-[2-methoxy-4-(3,3,4,4-tetrafluoropyrrolidin-1-yl)phenyl]-3-(1-phenyl-1H-pyrazol-5-yl)pyridazin-4 (H)-one A suspension of 1-(4-iodo-2-methoxyphenyl)-5-methoxy-3-(1-phenyl-1H-pyrazol-5-yl)pyridazin-4(1H)-one (186 mg), 3,3,4,4-tetrafluoropyrrolidine hydrochloride (80.0 mg), Pd$_2$(dba)$_3$ (6.8 mg), Xantphos (17.4 mg) and sodium tert-butoxide (93.0 mg) in 1,4-dioxane (2 mL) was stirred at 90° C. for 30 min under an argon atmosphere. The reaction mixture was poured into water, and the mixture was extracted with ethyl acetate. The extract was washed with saturated brine, dried over anhydrous magnesium sulfate, and concentrated under reduced pressure. The residue was purified by silica gel column chromatography (NH, ethyl acetate), and purified by HPLC (L-Column 2 ODS, mobile phase: water/acetonitrile (containing 5% ammonium acetate)). The obtained fraction was concentrated under reduced pressure, and to the residue was added saturated aqueous sodium hydrogen carbonate solution, and the mixture was extracted with ethyl acetate. The extract was washed with saturated brine, dried over anhydrous magnesium sulfate, and concentrated under reduced pressure. The residue was crystallized from methanol/water to give the title compound (41.1 mg).
mp 209-213° C.
$^1$H NMR (300 MHz, CDCl$_3$) δ 3.76-3.93 (10H, m), 5.91 (1H, dd, J=8.7, 2.6 Hz), 6.00 (1H, d, J=2.6 Hz), 6.31 (1H, d, J=8.7 Hz), 7.19 (1H, d, J=1.9 Hz), 7.31-7.45 (5H, m), 7.73 (1H, s), 7.76 (1H, d, J=1.9 Hz).
Anal. Calcd for C$_{25}$H$_{21}$F$_4$N$_5$O$_3$: C, 58.25; H, 4.11; N, 13.59. Found: C, 58.24; H, 4.10; N, 13.62.

Example 16

4-fluoro-5-[5-methoxy-4-oxo-3-(1-phenyl-1H-pyrazol-5-yl)pyridazin-1(4H)-yl]-1,3,3-trimethyl-1,3-dihydro-2H-indol-2-one A) 4-fluoro-3,3-dimethyl-5-nitro-1,3-dihydro-2H-indol-2-one To a solution of 4-fluoro-3,3-dimethyl-1,3-dihydro-2H-indol-2-one (4.1 g) in concentrated sulfuric acid (60 mL) was added dropwise a mixture of fuming nitric acid (0.99 mL) and concentrated sulfuric acid (10 mL) over 30 min at −30° C. The reaction mixture was stirred between −30° C. to 0° C. for 30 min, and poured into ice. The resulting solid was collected by filtration, washed with water, and dissolved in ethyl acetate. The obtained solution was washed with water and saturated brine, dried over anhydrous magnesium sulfate, and concentrated under reduced pressure. The obtained residue was purified by silica gel column chromatography (ethyl acetate/hexane) to give the title compound (2.2 g).
$^1$H NMR (300 MHz, CDCl$_3$) δ 1.57 (6H, s), 6.84 (1H, d, J=8.7 Hz), 8.10 (1H, dd, J=8.7, 7.5 Hz), 8.76 (1H, brs).

B) 5-amino-4-fluoro-3,3-dimethyl-1,3-dihydro-2H-indol-2-one

A suspension of 4-fluoro-3,3-dimethyl-5-nitro-1,3-dihydro-2H-indol-2-one (3.5 g), palladium on carbon (containing water (50%), 2.0 g) in methanol (150 mL) was stirred at room temperature for 3 hr under a hydrogen atmosphere. The palladium on carbon was removed by filtration, and the filtrate was concentrated under reduced pressure to give the title compound (2.9 g).
MS (API+), found: 195.1

C) methyl (2E)-2-[(4-fluoro-3,3-dimethyl-2-oxo-2,3-dihydro-1H-indol-5-yl)hydrazono]-4-methoxy-3-oxobutanoate By a method similar to Step F of Example 10, and using 5-amino-4-fluoro-3,3-dimethyl-1,3-dihydro-2H-indol-2-one, the title compound was obtained.
$^1$H NMR (300 MHz, CDCl$_3$) δ 1.54 (6H, s), 3.51 (3H, s), 3.88 (3H×½, s), 3.93 (3H×½, s), 4.66 (2H×½, s), 4.69 (2H×½, s), 6.78 (1H, d, J=8.3 Hz), 7.48 (1H×½, t, J=7.9 Hz), 7.72 (1H×½, t, J=8.1 Hz), 7.88 (1H×½, brs), 7.92 (1H×½, brs), 13.18 (1H×½, s), 15.12 (1H×½, s).

D) methyl 1-(4-fluoro-1,3,3-trimethyl-2-oxo-2,3-dihydro-1H-indol-5-yl)-5-methoxy-4-oxo-1,4-dihydropyridazine-3-carboxylate By a method similar to Step G of Example 10, and using methyl (2E)-2-[(4-fluoro-3,3-dimethyl-2-oxo-2,3-dihydro-1H-indol-5-yl)hydrazono]-4-methoxy-3-oxobutanoate, the title compound was obtained.
$^1$H NMR (300 MHz, CDCl$_3$) δ 1.53 (6H, s), 3.27 (3H, s), 3.93 (3H, s), 3.98 (3H, s), 6.78 (1H, d, J=8.3 Hz), 7.52 (1H, dd, J=8.3, 7.5 Hz), 7.72 (1H, d, J=2.3 Hz).

E) 1-(4-fluoro-1,3,3-trimethyl-2-oxo-2,3-dihydro-1H-indol-5-yl)-5-methoxy-4-oxo-1,4-dihydropyridazine-3-carboxylic acid By a method similar to Step H of Example 10, and using methyl 1-(4-fluoro-1,3,3-trimethyl-2-oxo-2,3-dihydro-1H-indol-5-yl)-5-methoxy-4-oxo-1,4-dihydropyridazine-3-carboxylate, the title compound was obtained.
$^1$H NMR (300 MHz, DMSO-d$_6$) δ 1.43 (6H, s), 3.22 (3H, s), 3.90 (3H, s), 7.15 (1H, d, J=8.3 Hz), 7.75 (1H, t, J=8.1 Hz), 8.88 (1H, s).

F) 1-(4-fluoro-1,3,3-trimethyl-2-oxo-2,3-dihydro-1H-indol-5-yl)-N,5-dimethoxy-N-methyl-4-oxo-1,4-dihydropyridazine-3-carboxamide By a method similar to Step I of Example 10, and using 1-(4-fluoro-1,3,3-trimethyl-2-oxo-2,3-dihydro-1H-indol-5-yl)-5-methoxy-4-oxo-1,4-dihydropyridazine-3-carboxylic acid, the title compound was obtained.
$^1$H NMR (300 MHz, CDCl$_3$) δ 1.52 (6H, s), 3.26 (3H, s), 3.39 (3H, s), 3.73 (3H, s), 3.93 (3H, s), 6.76 (1H, d, J=8.3 Hz), 7.52 (1H, t, J=7.9 Hz), 7.75 (1H, d, J=1.9 Hz)

G) 5-(3-acetyl-5-methoxy-4-oxopyridazin-1(4H)-yl)-4-fluoro-1,3,3-trimethyl-1,3-dihydro-2H-indol-2-one By a method similar to Step J of Example 10, and using 1-(4-fluoro-1,3,3-trimethyl-2-oxo-2,3-dihydro-1H-indol-5-yl)-N,5-dimethoxy-N-methyl-4-oxo-1,4-dihydropyridazine-3-carboxamide, the title compound was obtained.
$^1$H NMR (300 MHz, CDCl$_3$) δ 1.53 (6H, s), 2.69 (3H, s), 3.27 (3H, s), 3.93 (3H, s), 6.80 (1H, d, J=8.3 Hz), 7.53 (1H, t, J=7.9 Hz), 7.72 (1H, d, J=2.3 Hz).

H) 4-fluoro-5-[5-methoxy-4-oxo-3-(1-phenyl-1H-pyrazol-5-yl)pyridazin-1(4H)-yl]-1,3,3-trimethyl-1,3-dihydro-2H-indol-2-one By a method similar to Step B of Example 15, and using 5-(3-acetyl-5-methoxy-4-oxopyridazin-1(4H)-yl)-4-fluoro-1,3,3-trimethyl-1,3-dihydro-2H-indol-2-one, the title compound was obtained.
MS (API+), found: 460.1

Example 17

5-{3-[1-(3-chlorophenyl)-1H-pyrazol-5-yl]-5-methoxy-4-oxopyridazin-1(4H)-yl}-4-fluoro-1,3,3-trimethyl-1,3-dihydro-2H-indol-2-one By a method similar to Step B of Example 15, and using 5-(3-acetyl-5-methoxy-4-oxopyridazin-1(4H)-yl)-4-fluoro-1,3,3-trimethyl-1,3-dihydro-2H-indol-2-one and 3-chlorophenylhydrazine, the title compound was obtained.
MS (API+), found: 494.2

Example 18

4-fluoro-5-[5-methoxy-4-oxo-3-(1-phenyl-1H-pyrazol-5-yl)pyridazin-1(4H)-yl]-3,3-dimethyl-1-(2,2,2-trifluoroethyl)-1,3-dihydro-2H-indol-2-one A) 1-methoxy-3-(1-phenyl-1H-pyrazol-5-yl)propan-2-ol To an THF solution (450 ml) of 1-phenylpyrazole (15 g) was added 1.6M butyllithium/hexane solution at −78° C., and the mixture was stirred at −78° C. for 1 hr. To the reaction mixture was added 2-(methoxymethyl)oxirane (27.8 ml) at −78° C., and the mixture was allowed to be warmed to room temperature, and stirred for 1 hr. To the reaction mixture was added 1N hydrochloric acid, the mixture was extracted with ethyl acetate, and the extract was concentrated under reduced pressure. The residue was purified by silica gel column chromatography (ethyl acetate/hexane) to give the title compound (12.2 g).
$^1$H NMR (300 MHz, CDCl$_3$) δ 2.33 (1H, d, J=4.1 Hz), 2.88 (2H, dd, J=6.6, 3.2 Hz), 3.19-3.28 (1H, m), 3.33 (3H, s), 3.34-3.40 (1H, m), 3.94-4.06 (1H, m, J=10.0, 6.8, 3.4, 3.4 Hz), 6.30-6.38 (1H, m), 7.34-7.53 (5H, m), 7.63 (1H, s).

B) 1-methoxy-3-(1-phenyl-1H-pyrazol-5-yl)propan-2-one

To a THF solution (100 ml) of DMSO (14.2 ml) was added dropwise trifluoroacetic anhydride over 15 min at −42° C., and the mixture was stirred at −42° C. for 15 min. To the reaction mixture was added dropwise an THF solution (66 ml) of 1-methoxy-3-(1-phenyl-1H-pyrazol-5-yl)propan-2-ol (9.3 g) over 1 hr at −42° C., and the mixture was stirred at 0° C. for 15 min. To the reaction mixture was added dropwise triethylamine (22.3 ml) over 15 min at 0° C., and the mixture was stirred at 0° C. for 1 hr. To the reaction mixture was added 10% aqueous sodium carbonate solution, and the mixture was extracted with ethyl acetate, and the extract was concentrated under reduced pressure. The residue was purified by silica gel column chromatography (ethyl acetate/hexane) to give the title compound (4.11 g).
$^1$H NMR (300 MHz, CDCl$_3$) δ 3.33 (3H, s), 3.88 (2H, s), 3.95 (2H, s), 6.34 (1H, d, J=1.9 Hz), 7.35-7.52 (5H, m), 7.66 (1H, d, J=1.9 Hz).

C) 4-fluoro-3,3-dimethyl-5-nitro-1-(2,2,2-trifluoroethyl)-1,3-dihydro-2H-indol-2-one A suspension of 4-fluoro-3,3-dimethyl-5-nitro-1,3-dihydro-2H-indol-2-one (0.10 g), 2,2,2-trifluoroethyl trifluoromethanesulfonate (0.16 g), potassium carbonate (0.12 g) and DMF (2 mL) was stirred at room temperature for 1 hr. To the reaction mixture was added water, and the mixture was extracted with ethyl acetate. The extract was washed with saturated brine, dried over anhydrous magnesium sulfate, and concentrated under reduced pressure. The obtained residue was purified by silica gel column chromatography (ethyl acetate/hexane) to give the title compound (2.2 g).
$^1$H NMR (300 MHz, CDCl$_3$) δ 1.58 (6H, s), 4.37 (2H, q, J=8.3 Hz), 6.86 (1H, d, J=8.7 Hz), 8.10-8.21 (1H, m).

D) 5-amino-4-fluoro-3,3-dimethyl-1-(2,2,2-trifluoroethyl)-1,3-dihydro-2H-indol-2-one By a method similar to Step B of Example 16, and using 4-fluoro-3,3-dimethyl-5-nitro-1-(2,2,2-trifluoroethyl)-1,3-dihydro-2H-indol-2-one, the title compound was obtained.
$^1$H NMR (300 MHz, CDCl$_3$) δ 1.50 (6H, s), 3.58 (2H, brs), 4.25 (2H, q, J=8.9 Hz), 6.51-6.58 (1H, m), 6.65-6.73 (1H, m).

E) 4-fluoro-5-[5-methoxy-4-oxo-3-(1-phenyl-1H-pyrazol-5-yl)pyridazin-1(4H)-yl]-3,3-dimethyl-1-(2,2,2-trifluoroethyl)-1,3-dihydro-2H-indol-2-one To a mixture of 5-amino-4-fluoro-3,3-dimethyl-1-(2,2,2-trifluoroethyl)-1,3-dihydro-2H-indol-2-one (300 mg) and 6M hydrochloric acid (1.1 mL) was added dropwise a solution of sodium nitrite (90 mg) in water (2 mL) at 0° C., and the mixture was stirred for 1 hr. The obtained aqueous solution was added to a suspension (cooled to 0° C.) of 1-methoxy-3-(1-phenyl-1H-pyrazol-5-yl)propan-2-one (250 mg) and sodium acetate (535 mg) in methanol (5 mL). The reaction mixture was stirred for 3 hr, and poured into water, and the mixture was extracted with ethyl acetate. The extract was dried over anhydrous sodium sulfate, and concentrated under reduced pressure. The obtained residue was dissolved in acetonitrile (10 mL), and N,N-dimethylformamide dimethyl acetal (10 mL) was added thereto. The reaction mixture was stirred overnight at 90° C., and concentrated under reduced pressure. The residue was purified by basic silica gel column chromatography (ethyl acetate/hexane), and recrystallized from ethyl acetate/hexane to give the title compound (160 mg).
MS (API+), found: 528.2

Example 19

1-(2,2-difluoroethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one By a method similar to Example 18, and using 2,2-difluoroethyl trifluoromethanesulfonate instead of 2,2,2-trifluoroethyl trifluoromethanesulfonate, the title compound was obtained.
MS (API+), found: 510.4

Example 20

4-fluoro-5-[5-methoxy-3-(3-methyl-1-phenyl-1H-pyrazol-5-yl)-4-oxopyridazin-1(4H)-yl]-3,3-dimethyl-1-(2,2,2-trifluoroethyl)-1,3-dihydro-2H-indol-2-one A) 1-methoxy-3-(3-methyl-1-phenyl-1H-pyrazol-5-yl)propan-2-one By a method similar to Steps A and B of Example 18, and using 3-methyl-1-phenylpyrazole, the title compound was obtained.
MS (API+), found: 247.4

B) 4-fluoro-5-[5-methoxy-3-(3-methyl-1-phenyl-1H-pyrazol-5-yl)-4-oxopyridazin-1(4H)-yl]-3,3-dimethyl-1-(2,2,2-trifluoroethyl)-1,3-dihydro-2H-indol-2-one By a method similar to Step E of Example 18, and using 1-methoxy-3-(3-methyl-1-phenyl-1H-pyrazol-5-yl)propan-2-one, the title compound was obtained.
MS (API+), found: 542.3

Example 21

1-(cyclopropylmethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one A) 1-(cyclopropylmethyl)-4-fluoro-3,3-dimethyl-5-nitro-1,3-dihydro-2H-indol-2-one To a solution of 4-fluoro-3,3-dimethyl-5-nitro-1,3-dihydro-2H-indol-2-one (300 mg) in DMF (10 mL) were added sodium hydride (69.6 mg) and (bromomethyl)cyclopropane (0.193 mL) at 0° C., and the mixture was allowed to be warmed to room temperature, and stirred overnight under a nitrogen atmosphere. The reaction mixture was cooled to 0° C., saturated aqueous ammonium chloride solution was added thereto, and the mixture was extracted with ethyl acetate. The extract was washed with saturated brine, dried over anhydrous magnesium sulfate, and concentrated under reduced pressure. The obtained residue was purified by silica gel column chromatography (ethyl acetate/hexane) to give the title compound (317 mg).
MS (ESI+), found: 279.2

B) 5-amino-1-(cyclopropylmethyl)-4-fluoro-3,3-dimethyl-1,3-dihydro-2H-indol-2-one By a method similar to Step B of Example 16, and using 1-(cyclopropylmethyl)-4-fluoro-3,3-dimethyl-5-nitro-1,3-dihydro-2H-indol-2-one, the title compound was obtained.
MS (ESI+), found: 249.2

C) 1-(cyclopropylmethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one By a method similar to Step E of Example 18, and using 5-amino-1-(cyclopropylmethyl)-4-fluoro-3,3-dimethyl-1,3-dihydro-2H-indol-2-one, the title compound was obtained.
MS (ESI+), found: 500.4

Example 22

5-methoxy-3-(1-phenyl-1H-pyrazol-5-yl)-1-pyridin-2-ylpyridazin-4(1H)-one

A) (1-phenyl-1H-pyrazol-5-yl)boronic acid

To a solution of 1-phenyl-1H-pyrazole (20.0 g) in THF (700 mL) was added dropwise n-butyllithium (2.5M hexane solution, 58.3 mL) at −78° C. under a nitrogen atmosphere, and the mixture was stirred at the same temperature for 30 min. To the reaction mixture was added triisopropyl borate (52.2 g) at −78° C., and the mixture was stirred at the same temperature for 1 hr, gradually allowed to be warmed to room temperature, and stirred at room temperature for 20 hr. The pH of the reaction mixture was adjusted to 5 with acetic acid (20 mL), and concentrated to give the title compound (25.0 g).
MS (ESI+): [M+H]$^+$ 189.0.

B) 1-phenyl-5-(4,4,5,5-tetramethyl-1,3,2-dioxaborolan-2-yl)-1H-pyrazole (1-Phenyl-1H-pyrazol-5-yl)boronic acid (25.0 g) was dissolved in toluene (700 mL), pinacol (18.0 g) was added thereto at room temperature, and the mixture was stirred at 40° C. for 2 days. The reaction mixture was diluted with dichloromethane, and the mixture was washed with water and saturated brine, dried over anhydrous sodium sulfate, filtered, and concentrated. The resulting solid was collected by filtration, and washed with hexane to give the title compound (19.8 g).
$^1$H NMR (400 MHz, CDCl$_3$) δ 1.27 (12H, s), 6.89 (1H, d, J=1.6 Hz), 7.33-7.43 (3H, m), 7.52-7.55 (2H, m), 7.72 (1H, d, J=1.6 Hz).

C) 3-chloro-5-methoxypyridazin-4-ol

3-Chloro-4,5-dimethoxypyridazine (17.0 g) and morpholine (59.0 mL) were stirred at 100° C. for 2 hr, and cooled to 0° C. To the reaction mixture was added phenyl isocyanate (73.8 mL) at 0° C., and the mixture was stirred at the same temperature for 30 min, and diluted with ethyl acetate. The resulting solid was removed by filtration. The filtrate was concentrated, and the residue was purified by column chromatography (ethyl acetate/hexane-methanol/ethyl acetate) to give the title compound (9.61 g).
$^1$H NMR (400 MHz, CD$_3$OD): δ 3.88 (3H, s), 8.26 (1H, s).

D) 1-benzyl-3-chloro-5-methoxypyridazin-4(1H)-one

3-Chloro-5-methoxypyridazin-4-ol (10.0 g) was dissolved in DMF (300 mL), sodium hydride (3.26 g, 55 wt %) and tetrabutylammonium iodide (4.60 g) were added thereto at 0° C., and the mixture was stirred at the same temperature for 10 min. To the reaction mixture was added benzyl bromide (12.3 g) at 0° C., and the mixture was stirred at room temperature for 20 hr. The reaction mixture was diluted with water, and the mixture was extracted with dichloromethane. The extract was washed with water and saturated brine, dried over anhydrous sodium sulfate, filtered, and concentrated. The residue was recrystallized from ethyl acetate/hexane to give the title compound (19.8 g).
$^1$H NMR (400 MHz, CDCl$_3$): δ 3.82 (3H, s), 5.31 (2H, s), 7.34-7.42 (5H, m), 7.89 (1H, s).

E) 1-benzyl-5-methoxy-3-(1-phenyl-1H-pyrazol-5-yl)pyridazin-4(1H)-one

1-Benzyl-3-chloro-5-methoxypyridazin-4(1H)-one (13.6 g), 1-phenyl-5-(4,4,5,5-tetramethyl-1,3,2-dioxaborolan-2-yl)-1H-pyrazole (22.0 g), potassium carbonate (51.0 g) and bis(di-tert-butyl(4-dimethylaminophenyl)phosphine)dichloropalladium(II) (1.92 g) were suspended in toluene (330 mL) and water (33.0 mL), and the suspension was heated under reflux under a nitrogen atmosphere for 24 hr. The reaction mixture was allowed to be cooled to room temperature, diluted with water and saturated aqueous sodium hydrogen carbonate solution, and the mixture was extracted with ethyl acetate. The extract was dried over anhydrous sodium sulfate, filtered, and concentrated. The residue was recrystallized from ethyl acetate/hexane to give the title compound (15.1 g).

¹H NMR (400 MHz, DMSO-d₆) δ 3.81 (3H, s), 5.10 (2H, s), 6.95 (1H, d, J=1.6 Hz), 7.05-7.07 (2H, m), 7.24-7.38 (8H, m), 7.74 (1H, d, J=1.6 Hz), 8.33 (1H, s).

F) 5-methoxy-3-(1-phenyl-1H-pyrazol-5-yl)pyridazin-4-ol 1-benzyl-5-methoxy-3-(1-phenyl-1H-pyrazol-5-yl)pyridazin-4(1H)-one (15.0 g) and palladium hydroxide on carbon (5.88 g, palladium 20%, moistened with 50% water) were suspended in THF (500 mL) and methanol (300 mL), and the suspension was stirred at room temperature for 2 days under a hydrogen atmosphere. The reaction mixture was filtered through celite, the filtrate was concentrated. The residue was solidified with ethanol/hexane to give the title compound (9.10 g).
MS (ESI+): [M+H]⁺ 269.2.

G) 5-methoxy-3-(1-phenyl-1H-pyrazol-5-yl)-1-(pyridin-2-yl)pyridazin-4(1H)-one

A suspension of 5-methoxy-3-(1-phenyl-1H-pyrazol-5-yl)pyridazin-4-ol (60 mg), 2-fluoropyridine (65 mg) and cesium carbonate (364 mg) in NMP (2 mL) was stirred at 100° C. for 3 days, 1M hydrochloric acid was added thereto, and the mixture was extracted with ethyl acetate. The extract was dried over anhydrous magnesium sulfate, and the solvent was evaporated under reduced pressure. The residue was purified by basic silica gel column chromatography (ethyl acetate/methanol) to give the title compound (20 mg).
MS (API+): [M+H]⁺ 346.4

Example 23

5-methoxy-1-(1-oxidopyridin-3-yl)-3-(1-phenyl-1H-pyrazol-5-yl)pyridazin-4(1H)-one To a DMF solution (2.0 ml) of m-chloroperbenzoic acid (0.398 mg) was added a DMF solution (12.0 ml) of 5-methoxy-3-(1-phenyl-1H-pyrazol-5-yl)-1-(pyridin-3-yl)pyridazin-4(1H)-one at 0° C., and the mixture was stirred overnight at room temperature. The precipitated solid was collected by filtration to give the title compound (168 mg).
¹H NMR (300 MHz, CDCl₃) δ 3.87 (3H, s), 6.98 (1H, d, J=9.82 Hz), 7.15 (1H, d, J=1.89 Hz), 7.27-7.53 (6H, m), 7.82 (1H, d, J=1.89 Hz), 8.18 (1H, d, J=6.42 Hz), 8.38-8.49 (1H, m), 8.58 (1H, s).

Example 24

5-methoxy-3-(1-phenyl-1H-pyrazol-5-yl)-1-(pyrazin-2-yl)pyridazin-4(1H)-one

By a method similar to Example 22, and using 2-fluoropyrazine, the title compound was obtained.
MS (API+), found: 347.3

Example 25

5-methoxy-3-(1-phenyl-1H-pyrazol-5-yl)-4H-1,3'-bipyridazin-4-one

By a method similar to Example 22, and using 3-chloropyridazine, the title compound was obtained.
MS (API+), found: 347.0

Example 26

5-methoxy-3-(1-phenyl-1H-pyrazol-5-yl)-1-pyrimidin-5-ylpyridazin-4(1H)-one

A suspension of 5-methoxy-3-(1-phenyl-1H-pyrazol-5-yl)pyridazin-4-ol (100 mg), 5-bromopyrimidine (119 mg), potassium carbonate (155 mg), copper(I) iodide (14 mg) and 4,7-dimethoxy-1,10-phenanthroline (20 mg) in DMSO (2 mL) was stirred at 110° C. for 40 hr under an argon atmosphere. To the reaction mixture was added aqueous sodium hydrogen carbonate solution, and the mixture was extracted with ethyl acetate. The extract was dried over anhydrous sodium sulfate, and the solvent was evaporated under reduced pressure. The residue was purified by basic silica gel column chromatography (ethyl acetate/methanol), and recrystallized from ethyl acetate/hexane to give the title compound (11 mg).
MS (API+), found: 347.3

Example 27

5-methoxy-3-(1-phenyl-1H-pyrazol-5-yl)-1-(1,3-thiazol-2-yl)pyridazin-4(1H)-one

By a method similar to Example 22, and using 2-chlorothiazole, the title compound (44 mg) was obtained.
MS (API+): [M+H]⁺ 352.3

Example 32

5-methoxy-3-(1-phenyl-1H-pyrazol-5-yl)-1-[6-(3,3,4,4-tetrafluoropyrrolidin-1-yl)pyridin-3-yl]pyridazin-4(1H)-one A) 5-nitro-2-(3,3,4,4-tetrafluoropyrrolidin-1-yl)pyridine Cesium carbonate (100 g) was suspended in DMF (200 ml), tetrafluoropyrrolidine hydrochloride (10 g) and 2-chloro-5-nitropyridine (20 g) were added thereto, and the mixture was stirred at room temperature for 90 hr. To the reaction mixture was added water, and the mixture was extracted with ethyl acetate. The extract was dried over anhydrous magnesium sulfate, and concentrated under reduced pressure. The residue was purified by silica gel column chromatography (ethyl acetate/hexane) to give the title compound as yellow crystals.
MS (ESI+): [M+H]⁺ 266.1

B) 6-(3,3,4,4-tetrafluoropyrrolidin-1-yl)pyridin-3-amine

By a method similar to Step B of Example 16, and using 3-nitro-6-(3,3,4,4-tetrafluoropyrrolidin-1-yl)pyridine, the title compound was obtained.
MS (API+): [M+H]⁺ 236.2

C) 5-methoxy-3-(1-phenyl-1H-pyrazol-5-yl)-1-[6-(3,3,4,4-tetrafluoropyrrolidin-1-yl)pyridin-3-yl]pyridazin-4(1H)-one By a method similar to Step E of Example 18, and using 6-(3,3,4,4-tetrafluoropyrrolidin-1-yl)pyridin-3-amine, the title compound was obtained.
MS (API+): [M+H]⁺ 487.1

Example 33

1-[6-(3,4-difluoro-1H-pyrrol-1-yl)pyridin-3-yl]-5-methoxy-3-(1-phenyl-1H-pyrazol-5-yl)pyridazin-4(1H)-one A mixture of 5-methoxy-3-(1-phenyl-1H-pyrazol-5-yl)-1-[6-(3,3,4,4-tetrafluoropyrrolidin-1-yl)pyridin-3-yl]pyridazin-4(1H)-one (367 mg), cesium carbonate (1.23 g) and DMF (4 ml) was stirred at 100° C. for 4 hr. To the reaction mixture were added water and ethyl acetate, and the precipitated crystals were collected by filtration, and recrystallized from DMSO-ethanol to give the title compound (146 mg) as whitish yellow crystals.

MS (API+): [M+H]$^+$ 447.1

Example 34

1-(1-benzyl-1H-pyrazol-4-yl)-5-methoxy-3-(1-phenyl-1H-pyrazol-5-yl)pyridazin-4(1H)-one To a mixture of 1-benzyl-1H-pyrazol-4-amine (75 mg) and 6M hydrochloric acid (1 mL) was added dropwise a solution of sodium nitrite (24 mg) in water (0.5 mL) at 0° C., and the mixture was stirred for 30 min. The obtained aqueous solution was added to a suspension (cooled to 0° C.) of 1-methoxy-3-(1-phenyl-1H-pyrazol-5-yl)propan-2-one (100 mg) and sodium acetate (354 mg) in methanol (2 mL). The reaction mixture was stirred for 3 hr, and poured into water, and the mixture was extracted with ethyl acetate. The extract was dried over anhydrous magnesium sulfate, and concentrated under reduced pressure. The obtained residue was dissolved in acetonitrile (2 mL), and N,N-dimethylformamide dimethyl acetal (0.3 mL) was added thereto. The reaction mixture was stirred at 80° C. for 12 hr, water was added thereto, and the mixture was extracted with ethyl acetate. The extract was dried over anhydrous magnesium sulfate, and concentrated under reduced pressure. The residue was purified by silica gel column chromatography (ethyl acetate/methanol) to give the title compound (11 mg).

MS (API+): [M+H]$^+$ 425.3

Example 35

5-methoxy-3-(1-phenyl-1H-pyrazol-5-yl)-1-[1-(2,2,2-trifluoroethyl)-1H-pyrazol-4-yl]pyridazin-4(1H)-one A) 1-(2,2,2-trifluoroethyl)-1H-pyrazol-4-amine To a suspension of 4-nitro-1H-pyrazole (500 mg) and potassium carbonate (1.22 g) in DMF (5 mL) was added dropwise 2,2,2-trifluoroethyl trifluoromethanesulfonate (1.54 g). The reaction mixture was stirred at room temperature for 4 hr, water was added thereto, and the mixture was extracted with ethyl acetate. The extract was dried over anhydrous magnesium sulfate, and concentrated under reduced pressure. A suspension of the obtained residue and palladium on carbon (1 g) in methanol (30 mL) was stirred at room temperature for 12 hr under a hydrogen atmosphere, filtered, and concentrated under reduced pressure. The residue was purified by preparative HPLC to give the title compound (490 mg).

$^1$H NMR (300 MHz, DMSO-d$_6$) δ 3.97 (2H, brs), 4.88 (2H, q, J=9.1 Hz), 7.04 (1H, s), 7.10 (1H, s)

B) 5-methoxy-3-(1-phenyl-1H-pyrazol-5-yl)-1-[1-(2,2,2-trifluoroethyl)-1H-pyrazol-4-yl]pyridazin-4(1H)-one By a method similar to Example 34, and using 1-(2,2,2-trifluoroethyl)-1H-pyrazol-4-amine, the title compound was obtained.

MS (API+): [M+H]$^+$ 417.4

Example 36

1-[1-(cyclopropylmethyl)-1H-pyrazol-4-yl]-5-methoxy-3-(1-phenyl-1H-pyrazol-5-yl)pyridazin-4(1H)-one A) 1-(cyclopropylmethyl)-1H-pyrazol-4-amine By a method similar to Step A of Example 35, and using (bromomethyl)cyclopropane, the title compound was obtained.

$^1$H NMR (300 MHz, DMSO-d$_6$) δ 0.24-0.33 (2H, m), 0.42-0.54 (2H, m), 1.02-1.20 (1H, m), 3.70-3.88 (4H, m), 6.87 (1H, s), 7.06 (1H, s).

B) 1-[1-(cyclopropylmethyl)-1H-pyrazol-4-yl]-5-methoxy-3-(1-phenyl-1H-pyrazol-5-yl)pyridazin-4(1H)-one By a method similar to Step E of Example 18, and using 1-(cyclopropylmethyl)-1H-pyrazol-4-amine, the title compound was obtained.

MS (API+): [M+H]$^+$ 389.2

Example 37

1-[1-(dicyclopropylmethyl)-1H-pyrazol-4-yl]-5-methoxy-3-(1-phenyl-1H-pyrazol-5-yl)pyridazin-4(1H)-one A) 1-(dicyclopropylmethyl)-1H-pyrazol-4-amine To a solution of 4-nitro-1H-pyrazole (500 mg), dicyclopropylmethanol (0.92 g) and triphenylphosphine (2.3 g) in THF (10 mL) was added diisopropyl azodicarboxylate toluene (1.9M, 4.6 mL) solution at room temperature. The reaction mixture was stirred at room temperature for 2 hr, water was added thereto, and the mixture was extracted with ethyl acetate. The extract was dried over anhydrous magnesium sulfate, and concentrated under reduced pressure. A suspension of the obtained residue and palladium on carbon (1 g) in methanol (30 mL) was stirred at room temperature for 12 hr under a hydrogen atmosphere, filtered, and concentrated under reduced pressure. The residue was purified by preparative HPLC to give the title compound (140 mg).

$^1$H NMR (300 MHz, DMSO-d$_6$) δ 0.11-0.24 (2H, m), 0.26-0.42 (4H, m), 0.47-0.63 (2H, m), 1.19-1.37 (2H, m), 2.80 (1H, t, J=8.7 Hz), 3.73 (2H, s), 6.87 (1H, s), 7.08 (1H, s).

B) 1-[1-(dicyclopropylmethyl)-1H-pyrazol-4-yl]-5-methoxy-3-(1-phenyl-1H-pyrazol-5-yl)pyridazin-4(1H)-one By a method similar to Step E of Example 18, and using 1-(dicyclopropylmethyl)-1H-pyrazol-4-amine, the title compound was obtained.

MS (API+): [M+H]$^+$ 429.1

Example 38

5-methoxy-1-[1-(1-phenylethyl)-1H-pyrazol-4-yl]-3-(1-phenyl-1H-pyrazol-5-yl)pyridazin-4(1H)-one By a method similar to Step E of Example 18, and using 1-(1-phenylethyl)-1H-pyrazol-4-amine, the title compound was obtained.
MS (API+): [M+H]$^+$ 439.4

Example 39

5-methoxy-1-[1-(1-methylethyl)-1H-pyrazol-4-yl]-3-(1-phenyl-1H-pyrazol-5-yl)pyridazin-4(1H)-one By a method similar to Step E of Example 18, and using 1-(1-methylethyl)-1H-pyrazol-4-amine, the title compound was obtained.
MS (API+): [M+H]$^+$ 377.0

Example 40

1-[1-(1-cyclopropylethyl)-1H-pyrazol-4-yl]-5-methoxy-3-(1-phenyl-1H-pyrazol-5-yl)pyridazin-4(1H)-one A) 1-(1-cyclopropylethyl)-1H-pyrazol-4-amine By a method similar to Step A of Example 37, and using 1-cyclopropylethanol, the title compound was obtained.
$^1$H NMR (300 MHz, DMSO-d$_6$) δ 0.39-0.50 (2H, m), 0.52-0.63 (1H, m), 0.65-0.76 (1H, m), 1.24-1.37 (1H, m), 1.60 (3H, d, J=6.8 Hz), 3.56-3.70 (1H, m), 3.97 (2H, brs), 7.08 (1H, s), 7.28 (1H, s).

B) 1-[1-(1-cyclopropylethyl)-1H-pyrazol-4-yl]-5-methoxy-3-(1-phenyl-1H-pyrazol-5-yl)pyridazin-4(1H)-one By a method similar to Step E of Example 18, and using 1-(1-cyclopropylethyl)-1H-pyrazol-4-amine, the title compound was obtained.
MS (API+): [M+H]$^+$ 403.1

Example 41

5-methoxy-3-(1-methyl-1H-pyrazol-5-yl)-1-(pyridin-3-yl)pyridazin-4(1H)-one

An acetonitrile suspension (7.5 mL) of 3-acetyl-5-methoxy-1-(pyridin-3-yl)pyridazin-4(1H)-one (0.5 g) was stirred at 70° C. for 10 min, and allowed to be cooled to room temperature. Then, N,N-dimethylformamide dimethyl acetal (2.5 mL) was added thereto, and the mixture was stirred at 80° C. for 2 hr. The insoluble material was removed by filtration, and the filtrate was concentrated to dryness under reduced pressure. The residue was dissolved in ethanol (5.4 mL). To the reaction mixture was added dropwise a 10%-TFA containing ethanol solution (5.4 mL) of methylhydrazine (139 mg) under ice-cooling with stirring, and the mixture was stirred at the same temperature for 10 min, allowed to be warmed to room temperature, and stirred for 16 hr. The reaction mixture was concentrated to dryness under reduced pressure, and the residue was purified by column chromatography (NH, ethyl acetate/methanol). The eluted product was crystallized from ethyl acetate to give the title compound (47 mg) as pale-yellow crystals.

$^1$H NMR (300 MHz, CDCl$_3$) δ 3.99 (3H, s), 4.12 (3H, s), 7.24 (1H, d, J=1.9 Hz), 7.53 (1H, dd, J=8.3, 4.2 Hz), 7.57 (1H, d, J=1.9 Hz), 7.97-8.04 (2H, m), 8.69-8.73 (1H, m), 8.97 (1H, d, J=2.6 Hz).
[M+H]$^+$ 284.17.

Example 42

5-methoxy-1-[1-(2-methylpropyl)-1H-pyrazol-4-yl]-3-(1-phenyl-1H-pyrazol-5-yl)pyridazin-4(1H)-one A) 1-(2-methylpropyl)-4-nitro-1H-pyrazole To a DMF solution (30 ml) of 4-nitro-1H-pyrazole (1.00 g) were added potassium carbonate (3.67 g) and 1-bromo-2-methylpropane (1.82 g), and the mixture was stirred at 70° C. for 3 hr. To the reaction mixture was added water, and the mixture was extracted with ethyl acetate. The extract was washed with saturated brine, dried over anhydrous magnesium sulfate, and concentrated under reduced pressure to give the title compound (4.13 g, containing DMF).
$^1$H NMR (300 MHz, CDCl$_3$) δ 0.95 (6H, d, J=6.8 Hz), 2.17-2.43 (1H, m), 3.95 (2H, d, J=7.2 Hz), 8.09 (2H, d, J=6.4 Hz).

B) 1-(2-methylpropyl)-1H-pyrazol-4-amine

By a method similar to Step B of Example 16, and using 1-(2-methylpropyl)-4-nitro-1H-pyrazole, the title compound was obtained.
MS (API+): [M+H]$^+$ 140.3

C) 5-methoxy-1-[1-(2-methylpropyl)-1H-pyrazol-4-yl]-3-(1-phenyl-1H-pyrazol-5-yl)pyridazin-4(1H)-one By a method similar to Step E of Example 18, and using 1-(2-methylpropyl)-1H-pyrazol-4-amine, the title compound was obtained.
MS (API+): [M+H]$^+$ 391.1

Example 43

1-[1-(cyclobutylmethyl)-1H-pyrazol-4-yl]-5-methoxy-3-(1-phenyl-1H-pyrazol-5-yl)pyridazin-4(1H)-one By a method similar to Example 42, and using (bromomethyl)cyclobutane, the title compound (196 mg) was obtained.
MS (API+): [M+H]$^+$ 403.1

Example 44

1-[1-(1-cyclopropylethyl)-1H-pyrazol-4-yl]-5-methoxy-3-(1-phenyl-1H-pyrazol-5-yl)pyridazin-4(1H)-one (retention time: shorter)

A racemate (140 mg) of 1-[1-(1-cyclopropylethyl)-1H-pyrazol-4-yl]-5-methoxy-3-(1-phenyl-1H-pyrazol-5-yl)pyridazin-4(1H)-one was separated by HPLC (column: CHIRALCEL OJ (MC001), 50 mmID×500 mL, manufactured by DAICEL CHEMICAL INDUSTRIES, LTD., mobile phase: hexane/ethanol=100/900) to give the title compound (63 mg) having a shorter retention time.
MS (API+): [M+H]$^+$ 403.1

Example 45

1-[1-(1-cyclopropylethyl)-1H-pyrazol-4-yl]-5-methoxy-3-(1-phenyl-1H-pyrazol-5-yl)pyridazin-4(1H)-one (retention time: longer)

A racemate (140 mg) of 1-[1-(1-cyclopropylethyl)-1H-pyrazol-4-yl]-5-methoxy-3-(1-phenyl-1H-pyrazol-5-yl)pyridazin-4(1H)-one was separated by HPLC (column: CHIRALCEL OJ (MC001), 50 mmIDx500 mL, manufactured by DAICEL CHEMICAL INDUSTRIES, LTD., mobile phase: hexane/ethanol=100/900) to give the title compound (63 mg) having a longer retention time.
MS (API+): [M+H]+ 403.1

Example 46

1-(7-fluoro-1,2-dimethyl-1H-benzimidazol-6-yl)-5-methoxy-3-(1-phenyl-1H-pyrazol-5-yl)pyridazin-4(1H)-one A) 2,3-difluoro-N-methyl-6-nitroaniline To a DMF solution (50 mL) of 2,3-difluoro-6-nitroaniline (3.0 g) were added potassium carbonate (14.3 g), and methyl iodide (3.23 mL), and the mixture was stirred at 50° C. for 4 hr. To the reaction mixture was added water, and the mixture was extracted with ethyl acetate. The extract was washed with saturated brine, dried over anhydrous magnesium sulfate, and concentrated under reduced pressure. The residue was purified by silica gel column chromatography (ethyl acetate/hexane) to give the title compound (2.66 g).
MS (ESI+): [M+H]+ 189.1

B) $N^1$-(diphenylmethyl)-2-fluoro-$N^3$-methyl-4-nitrobenzene-1,3-diamine

A mixture of 2,3-difluoro-N-methyl-6-nitroaniline (2.66 g), 1,1-diphenylmethanamine (5.18 g), diisopropylethylamine (4.56 g) and butan-1-ol (26.6 mL) was heated at 200° C. for 2 hr using a microwave reactor. To the reaction mixture was added saturated sodium hydrogen carbonate solution, and the mixture was extracted with ethyl acetate. The extract was washed with saturated brine, and dried over anhydrous sodium sulfate, and concentrated under reduced pressure. The residue was purified by silica gel column chromatography (ethyl acetate/hexane) to give the title compound (1.47 g).
MS (ESI+): [M+H]+ 352.3

C) N-(diphenylmethyl)-7-fluoro-1,2-dimethyl-1H-benzimidazol-6-amine

To a mixture of $N^1$-(diphenylmethyl)-2-fluoro-$N^3$-methyl-4-nitrobenzene-1,3-diamine (1.47 g), zinc (1.37 g), methanol (21 mL) and THF (21 mL) was added dropwise saturated aqueous ammonium chloride solution (17 mL), and the mixture was stirred at room temperature for 3 hr. To the reaction mixture was added saturated ammonium acetate solution, and the mixture was extracted with ethyl acetate. The extract was washed with saturated brine, and dried over anhydrous sodium sulfate, and concentrated under reduced pressure. To the residue were added ethanol (42 mL), triethylamine (1.17 mL) and acetamidine hydrochloride (0.79 g), and the mixture was stirred at 100° C. for 6 hr, and concentrated under reduced pressure. The residue is was purified by silica gel column chromatography (ethyl acetate/hexane) to give the title compound (0.58 g).
MS (ESI+): [M+H]+ 364.4

D) 7-fluoro-1,2-dimethyl-1H-benzimidazol-6-amine

To a THF solution (10 mL) of N-(diphenylmethyl)-7-fluoro-1,2-dimethyl-1H-benzimidazol-6-amine was added 6N hydrochloric acid (10 mL), and the mixture was stirred at 100° C. for 2 hr, cooled, and concentrated under reduced pressure. The precipitated crystals were washed with methanol to give the title compound dihydrochloride (244 mg).
The washing was charged into MP-TsOH column, the column was washed with methanol, and was eluted with 0.5 M ammonia/methanol solution to give the title compound (100 mg).
MS (ESI+): [M+H]+ 180.2

E) 1-(7-fluoro-1,2-dimethyl-1H-benzimidazol-6-yl)-5-methoxy-3-(1-phenyl-1H-pyrazol-5-yl)pyridazin-4(1H)-one By a method similar to Step E of Example 18, and using 7-fluoro-1,2-dimethyl-1H-benzimidazol-6-amine, the title compound was obtained.
MS (API+): [M+H]+ 431.3

Example 47

4'-fluoro-5'-[5-methoxy-4-oxo-3-(1-phenyl-1H-pyrazol-5-yl)pyridazin-1(4H)-yl]-1'-methylspiro[cyclobutane-1,3'-indol]-2' (1'H)-one A) methyl 1-(2-fluoro-6-nitrophenyl)cyclobutanecarboxylate To a solution of sodium hydride (9.49 g) in DMF (75 mL) was added dropwise a solution of methyl (2-fluoro-6-nitrophenyl)acetate (23 g) and 1,3-dibromopropane (13.1 mL) in DMF (15 mL) at 0° C. The reaction mixture was stirred at room temperature for 4 hr, cooled to 0° C. Saturated aqueous ammonium chloride solution was added thereto, and the mixture was extracted with ethyl acetate. The extract was washed with water and saturated brine, dried over anhydrous magnesium sulfate, and concentrated under reduced pressure. The residue was purified by silica gel column chromatography (ethyl acetate/hexane) to give the title compound (11.3 g).
$^1$H NMR (300 MHz, CDCl$_3$) δ 1.75-1.91 (1H, m), 2.37-2.54 (3H, m), 2.71-2.86 (2H, m), 3.77 (3H, s), 7.28-7.41 (2H, m), 7.52-7.58 (1H, m).

B) 4'-fluorospiro[cyclobutane-1,3'-indol]-2' (1'H)-one

To a solution of methyl 1-(2-fluoro-6-nitrophenyl)cyclobutanecarboxylate (3.11 g) in acetic acid (60 mL) was added zinc (16.1 g), and the mixture was stirred overnight at room temperature. The zinc was removed by filtration, and the filtrate was concentrated under reduced pressure, and the residue was dissolved in ethyl acetate. The solution was washed with saturated aqueous sodium hydrogen carbonate solution, dried over anhydrous magnesium sulfate, and concentrated under reduced pressure. The residue was purified by silica gel column chromatography (ethyl acetate/hexane) to give the title compound (2.30 g).
$^1$H NMR (300 MHz, CDCl$_3$) δ 2.24-2.45 (2H, m), 2.56-2.71 (4H, m), 6.62-6.82 (2H, m), 7.16 (1H, td, J=8.1, 5.3 Hz), 8.44 (1H, brs).

C) 4'-fluoro-5'-nitrospiro[cyclobutane-1,3'-indol]-2'(1'H)-one

By a method similar to Step A of Example 16, and using 4'-fluorospiro[cyclobutane-1,3'-indol]-2'(1'H)-one, the title compound was obtained.

$^1$H NMR (300 MHz, DMSO-d$_6$) δ 2.14-2.35 (2H, m), 2.36-2.67 (4H, m), 6.83 (1H, d, J=8.7 Hz), 8.11 (1H, dd, J=8.7, 7.9 Hz), 11.13 (1H, brs).

D) 4'-fluoro-1'-methyl-5'-nitrospiro[cyclobutane-1,3'-indol]-2'(1'H)-one

To a solution of 4'-fluoro-5'-nitrospiro[cyclobutane-1,3'-indol]-2'(1'H)-one (300 mg) and sodium hydride (36.6 mg) in DMF (10 mL) was added methyl iodide (0.395 mL) at 0° C., and the mixture was stirred at room temperature for 1 hr under a nitrogen atmosphere. To the reaction mixture was added saturated aqueous ammonium chloride solution at 0° C., and the mixture was extracted with ethyl acetate. The extract was washed with water and saturated brine, dried over anhydrous magnesium sulfate, and concentrated under reduced pressure. The residue was purified by silica gel column chromatography (ethyl acetate/hexane) to give the title compound (282 mg).

MS (ESI+), found: 251.1

E) 5'-amino-4'-fluoro-1'-methylspiro[cyclobutane-1,3'-indol]-2'(1'H)-one

By a method similar to Step B of Example 16, and using 4'-fluoro-1'-methyl-5'-nitrospiro[cyclobutane-1,3'-indol]-2'(1'H)-one, the title compound was obtained.

MS (API+), found: 221.2

F) 4'-fluoro-5'-[5-methoxy-4-oxo-3-(1-phenyl-1H-pyrazol-5-yl)pyridazin-1(4H)-yl]-1'-methylspiro[cyclobutane-1,3'-indol]-2'(1'H)-one By a method similar to Step E of Example 18, and using 5'-amino-4'-fluoro-1'-methylspiro[cyclobutane-1,3'-indol]-2'(1'H)-one, the title compound was obtained.

MS (ESI+), found: 472.3

Example 48

4-fluoro-5-[5-methoxy-4-oxo-3-(1-phenyl-1H-pyrazol-5-yl)pyridazin-1(4H)-yl]-3,3-dimethyl-1-(1-methylethyl)-1,3-dihydro-2H-indol-2-one

A) 5-amino-4-fluoro-3,3-dimethyl-1-(1-methylethyl)-1,3-dihydro-2H-indol-2-one To a solution of 4-fluoro-3,3-dimethyl-5-nitro-1,3-dihydro-2H-indol-2-one (500 mg) and cesium carbonate (1.82 g) in DMF (10 mL) was added dropwise 2-bromopropane (0.523 mL) at room temperature, and the mixture was stirred at 80° C. for 2 hr under a nitrogen atmosphere. To the reaction mixture was added saturated aqueous ammonium chloride solution at 0° C., and the mixture was extracted with ethyl acetate. The extract was washed with water and saturated brine, dried over anhydrous magnesium sulfate, and concentrated under reduced pressure. The obtained residue was dissolved in ethanol (10 mL), palladium on carbon (containing water (50%), 237 mg) was added thereto, and the mixture was stirred at room temperature for 2 hr under a hydrogen atmosphere. The palladium on carbon was removed by filtration, and the filtrate was concentrated under reduced pressure to give the title compound (330 mg).

$^1$H NMR (300 MHz, CDCl$_3$) δ 1.40-1.48 (12H, m), 3.54 (2H, brs), 4.58 (1H, quin, J=7.0 Hz), 6.55-6.70 (2H, m).

B) 4-fluoro-5-[5-methoxy-4-oxo-3-(1-phenyl-1H-pyrazol-5-yl)pyridazin-1(4H)-yl]-3,3-dimethyl-1-(1-methylethyl)-1,3-dihydro-2H-indol-2-one By a method similar to Step E of Example 18, and using 5-amino-4-fluoro-3,3-dimethyl-1-(1-methylethyl)-1,3-dihydro-2H-indol-2-one, the title compound was obtained.

MS (ESI+), found: 488.4

Example 49

4'-fluoro-5'-[5-methoxy-4-oxo-3-(1-phenyl-1H-pyrazol-5-yl)pyridazin-1(4H)-yl]-1'-(1-methylethyl)spiro[cyclobutane-1,3'-indol]-2'(1'H)-one

A) 5'-amino-4'-fluoro-1'-(1-methylethyl)spiro[cyclobutane-1,3'-indol]-2'(1'H)-one By a method similar to Step A of Example 48, and using 2-bromopropane, the title compound was obtained.

$^1$H NMR (300 MHz, CDCl$_3$) δ 1.40 (3H, s), 1.43 (3H, s), 2.27-2.40 (2H, m), 2.53-2.63 (4H, m), 3.55 (2H, brs), 4.57 (1H, quin, J=7.1 Hz), 6.52-6.58 (1H, m), 6.60-6.69 (1H, m).

B) 4'-fluoro-5'-[5-methoxy-4-oxo-3-(1-phenyl-1H-pyrazol-5-yl)pyridazin-1(4H)-yl]-1'-(1-methylethyl)spiro[cyclobutane-1,3'-indol]-2'(1'H)-one By a method similar to Step E of Example 18, and using 5'-amino-4'-fluoro-1'-(1-methylethyl)spiro[cyclobutane-1,3'-indol]-2'(1'H)-one, the title compound was obtained.

MS (ESI+), found: 500.4

Example 50

1-cyclobutyl-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one

A) 1-cyclobutyl-4-fluoro-3,3-dimethyl-5-nitro-1,3-dihydro-2H-indol-2-one

To a solution of 4-fluoro-3,3-dimethyl-5-nitro-1,3-dihydro-2H-indol-2-one (300 mg), cyclobutanol (0.136 mL) and triphenylphosphine (702 mg) in THF (15 mL) was added dropwise diethyl azocarboxylate (40% toluene solution, 1.48 mL) at 0° C., and the mixture was stirred for 5 hr under a nitrogen atmosphere. To the reaction mixture was added water at 0° C., and the mixture was extracted with ethyl acetate. The extract was washed with water and saturated brine, dried over anhydrous magnesium sulfate, and concentrated under reduced pressure. The residue was purified by silica gel column chromatography (ethyl acetate/hexane) to give the title compound (200 mg).

MS (ESI+), found: 279.2

B) 5-amino-1-cyclobutyl-4-fluoro-3,3-dimethyl-1,3-dihydro-2H-indol-2-one

By a method similar to Step B of Example 16, and using 1-cyclobutyl-4-fluoro-3,3-dimethyl-5-nitro-1,3-dihydro-2H-indol-2-one, the title compound was obtained.
MS (ESI+), found: 249.1

C) 1-cyclobutyl-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one By a method similar to Step E of Example 18, and using 5-amino-1-cyclobutyl-4-fluoro-3,3-dimethyl-1,3-dihydro-2H-indol-2-one, the title compound was obtained.
MS (ESI+), found: 500.4

Example 51

1-[1-(cyclopropylmethyl)-1H-pyrazol-4-yl]-5-methoxy-3-(3-methyl-1-phenyl-1H-pyrazol-5-yl)pyridazin-4(1H)-one By a method similar to Step E of Example 18, and using 1-(cyclopropylmethyl)-1H-pyrazol-4-amine and 1-methoxy-3-(3-methyl-1-phenyl-1H-pyrazol-5-yl)propan-2-one, the title compound was obtained.
MS (API+), found: 403.4

Example 52

5-methoxy-1-[2-methoxy-6-(3,3,4,4-tetrafluoropyrrolidin-1-yl)pyridin-3-yl]-3-(1-phenyl-1H-pyrazol-5-yl)pyridazin-4(1H)-one By a method similar to Example 32, and using 2-chloro-6-methoxy-5-nitropyridine, the title compound was obtained.
MS (API+), found: 517.2

Example 53

1-[6-(3,4-difluoro-1H-pyrrol-1-yl)-2-methoxypyridin-3-yl]-5-methoxy-3-(1-phenyl-1H-pyrazol-5-yl)pyridazin-4(1H)-one By a method similar to Example 32, and using 5-methoxy-1-[2-methoxy-6-(3,3,4,4-tetrafluoropyrrolidin-1-yl)pyridin-3-yl]-3-(1-phenyl-1H-pyrazol-5-yl)pyridazin-4(1H)-one, the title compound was obtained.
MS (API+), found: 477.1

Example 54

5-methoxy-1-{1-[(1-methylcyclopropyl)methyl]-1H-pyrazol-4-yl}-3-(1-phenyl-1H-pyrazol-5-yl)pyridazin-4(1H)-one By a method similar to Step A of Example 35 and Step E of Example 18, and using 1-(bromomethyl)-1-methylcyclopropane, the title compound was obtained.
MS (API+), found: 403.1

Example 55

5-methoxy-1-[1-(2,2,3,3,3-pentafluoropropyl)-1H-pyrazol-4-yl]-3-(1-phenyl-1H-pyrazol-5-yl)pyridazin-4(1H)-one By a method similar to Step A of Example 35 and Step E of Example 18, and using 2,2,3,3,3-pentafluoropropyl trifluoromethanesulfonate, the title compound was obtained.
MS (API+), found: 467.3

The structures and the like of the compound of Examples 1 to 55 are shown in Tables 1 to 11. The structures and the like of the compound of Examples 56 to 102, which were synthesized according to the synthetic method of Examples 1 to 55, are shown in Tables 11 to 20.

TABLE 1

| Ex. No. | IUPAC NAME | Structure | MS |
|---|---|---|---|
| 1 | 1-[2-fluoro-4-(1H-pyrazol-1-yl)phenyl]-5-methoxy-3-(3-methyl-1-phenyl-1H-pyrazol-5-yl)pyridazin-4(1H)-one | 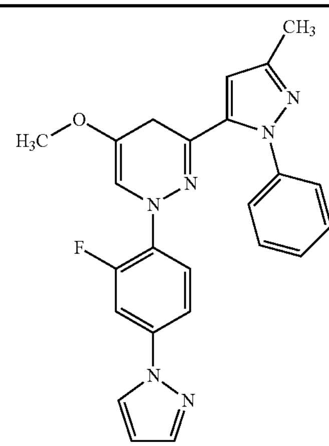 | 443.3 |

TABLE 1-continued

| Ex. No. | IUPAC NAME | Structure | MS |
|---|---|---|---|
| 2 | 5-methoxy-1-[2-methoxy-4-(1H-pyrazol-1-yl)phenyl]-3-(3-methyl-1-phenyl-1H-pyrazol-5-yl)pyridazin-4(1H)-one | 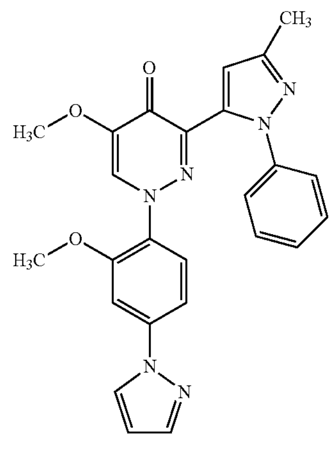 [SMILES: COc1cc(-n2cccn2)ccc1-n1cc(OC)c(=O)c(-c2cc(C)nn2-c2ccccc2)n1] | 455.3 |
| 3 | 3-[1-(3-chloro-2-fluorophenyl)-1H-pyrazol-5-yl]-1-[2-fluoro-4-(1H-pyrazol-1-yl)phenyl]-5-methoxypyridazin-4(1H)-one | 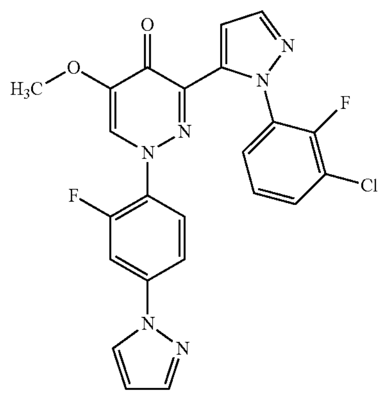 [SMILES: COc1cn(-c2ccc(-n3cccn3)cc2F)nc(-c2ccnn2-c2cccc(Cl)c2F)c1=O] | 481.3 |
| 4 | 3-[1-(5-chloro-2-fluorophenyl)-1H-pyrazol-5-yl]-1-[2-fluoro-4-(1H-pyrazol-1-yl)phenyl]-5-methoxypyridazin-4(1H)-one | 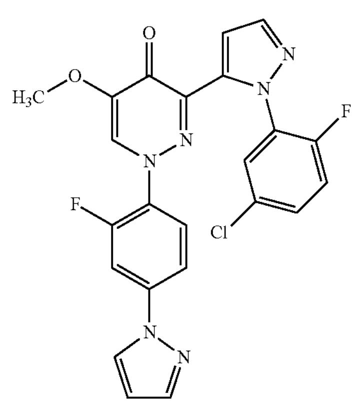 [SMILES: COc1cn(-c2ccc(-n3cccn3)cc2F)nc(-c2ccnn2-c2cc(Cl)ccc2F)c1=O] | 481.3 |

TABLE 1-continued

| Ex. No. | IUPAC NAME | Structure | MS |
|---|---|---|---|
| 5 | 1-[2-fluoro-4-(1H-pyrazol-1-yl)phenyl]-5-methoxy-3-{1-[3-(trifluoromethyl)phenyl]-1H-pyrazol-5-yl}pyridazin-4(1H)-one | 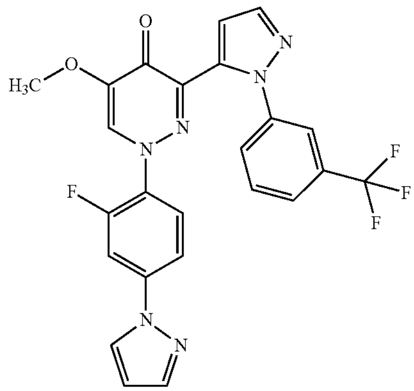 [SMILES: COc1cn(-c2ccc(-n3cccn3)cc2F)nc(-c2ccnn2-c2cccc(C(F)(F)F)c2)c1=O] | 497.2 |

TABLE 2

| Ex. No. | IUPAC NAME | Structure | MS |
|---|---|---|---|
| 6 | 1-[2-fluoro-4-(1H-pyrazol-1-yl)phenyl]-5-methoxy-3-[1-(2,2,2-trifluoroethyl)-1H-pyrazol-5-yl]pyridazin-4(1H)-one | 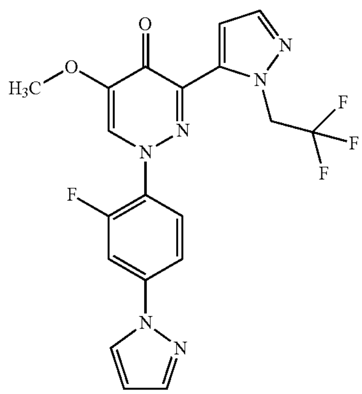 [SMILES: COc1cn(-c2ccc(-n3cccn3)cc2F)nc(-c2ccnn2CC(F)(F)F)c1=O] | |

$^1$H NMR (300 MHz, CDCl$_3$) δ 3.86 (3H, s), 5.36 (2H, q, J = 8.9 Hz), 6.65 (1H, d, J = 2.6 Hz), 7.17 (1H, d, J = 1.9 Hz), 7.86 (1H, d, J = 1.5 Hz), 7.89-7.99 (2H, m), 8.08 (1H, d, J = 1.9 Hz), 8.64 (1H, s), 8.70 (1H, d, J = 2.6 Hz).

| 7 | 1-[2-fluoro-4-(1H-pyrazol-1-yl)phenyl]-5-methoxy-3-{1-[3-(trifluoromethoxy)phenyl]-1H-pyrazol-5-yl}pyridazin-4(1H)-one | | |

$^1$H NMR (300 MHz, CDCl$_3$) δ 3.79 (3H, s), 6.64 (1H, d, J = 2.6 Hz), 7.03 (1H, d, J = 1.9 Hz), 7.27-7.49 (4H, m), 7.57 (1H, t, J = 8.1 Hz), 7.74-7.88 (3H, m), 7.99 (1H, dd, J = 12.1, 2.3 Hz), 8.57 (1H, d, J = 1.9 Hz), 8.66 (1H, d, J = 2.6 Hz).

TABLE 2-continued

| Ex. No. | IUPAC NAME | Structure | MS |
|---|---|---|---|
| 8 | 5-methoxy-1-[2-methoxy-4-(1H-pyrazol-1-yl)phenyl]-3-{1-[3-(trifluoromethyl)phenyl]-1H-pyrazol-5-yl}pyridazin-4(1H)-one | 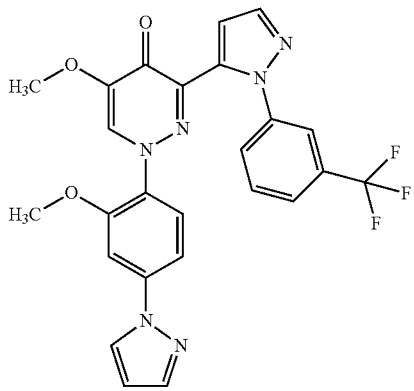 [SMILES: COc1cc(-n2cccn2)ccc1-n1cc(OC)c(=O)c(-c2ccnn2-c2cccc(C(F)(F)F)c2)n1] | 509.5 |
| 9 | 3-[1-(3-chlorophenyl)-1H-pyrazol-5-yl]-5-methoxy-1-[2-methoxy-4-(1H-pyrazol-1-yl)phenyl]pyridazin-4(1H)-one | 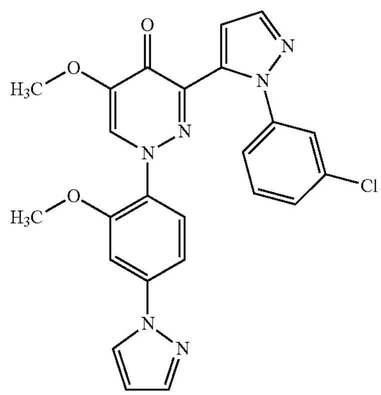 [SMILES: COc1cc(-n2cccn2)ccc1-n1cc(OC)c(=O)c(-c2ccnn2-c2cccc(Cl)c2)n1] | 475.5 |
| 10 | 1-[2-(benzyloxy)-4-(3,4-difluoro-1H-pyrrol-1-yl)phenyl]-5-methoxy-3-(1-phenyl-1H-pyrazol-5-yl)pyridazin-4(1H)-one | 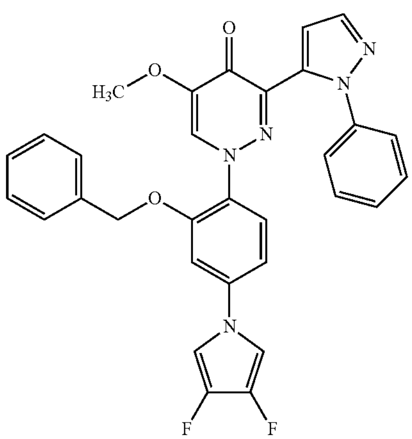 [SMILES: COc1cn(-c2ccc(-n3cc(F)c(F)c3)cc2OCc2ccccc2)nc(-c2ccnn2-c2ccccc2)c1=O] | 552.6 |

TABLE 3

| Ex. No. | IUPAC NAME | Structure | MS |
|---|---|---|---|
| 11 | 1-[4-(3,4-difluoro-1H-pyrrol-1-yl)-2-hydroxyphenyl]-5-methoxy-3-(1-phenyl-1H-pyrazol-5-yl)pyridazin-4(1H)-one | 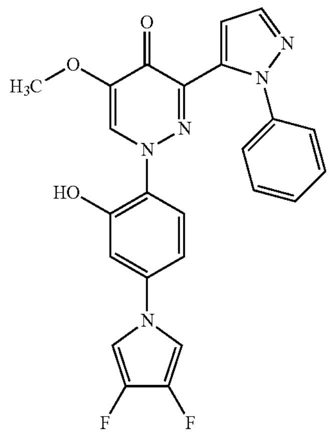 [SMILES: COc1cn(-c2ccc(-n3cc(F)c(F)c3)cc2O)nc(-c2ccnn2-c2ccccc2)c1=O] | 462.4 |
| 12 | 1-[4-(3,4-difluoro-1H-pyrrol-1-yl)-2-methoxyphenyl]-5-methoxy-3-(1-phenyl-1H-pyrazol-5-yl)pyridazin-4(1H)-one | 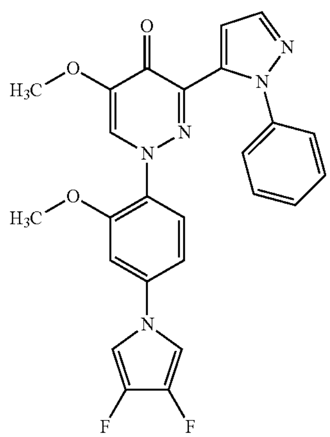 [SMILES: COc1cc(-n2cc(F)c(F)c2)ccc1-n1cc(OC)c(=O)c(-c2ccnn2-c2ccccc2)n1] | 476.4 |
| 13 | 1-[2-(difluoromethoxy)-4-(3,4-difluoro-1H-pyrrol-1-yl)phenyl]-5-methoxy-3-(1-phenyl-1H-pyrazol-5-yl)pyridazin-4(1H)-one | 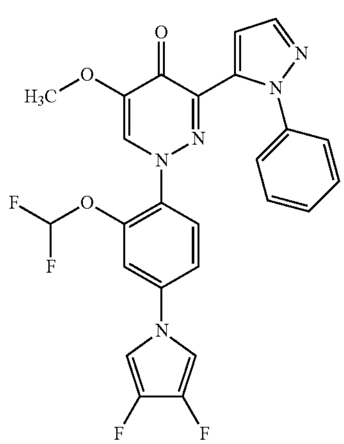 [SMILES: COc1cn(-c2ccc(-n3cc(F)c(F)c3)cc2OC(F)F)nc(-c2ccnn2-c2ccccc2)c1=O] | 512.5 |

TABLE 3-continued

| Ex. No. | IUPAC NAME | Structure | MS |
|---|---|---|---|
| 14 | 1-[4-(3,4-difluoro-1H-pyrrol-1-yl)-2-(2,2,2-trifluoroethoxy)phenyl]-5-methoxy-3-(1-phenyl-1H-pyrazol-5-yl)pyridazin-4(1H)-one | 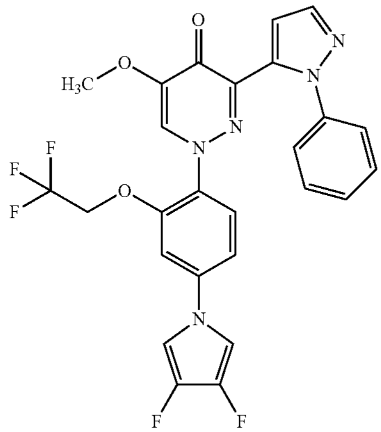 [SMILES: COc1cn(-c2ccc(-n3cc(F)c(F)c3)cc2OCC(F)(F)F)nc(-c2ccnn2-c2ccccc2)c1=O] | 544.5 |
| 15 | 5-methoxy-1-[2-methoxy-4-(3,3,4,4-tetrafluoropyrrolidin-1-yl)phenyl]-3-(1-phenyl-1H-pyrazol-5-yl)pyridazin-4(1H)-one | 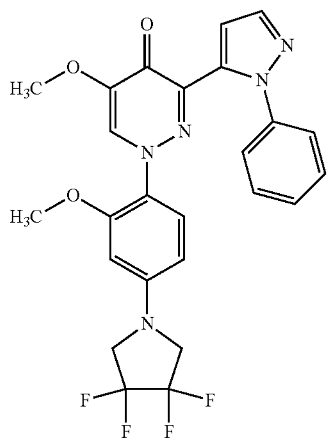 [SMILES: COc1cc(N2CC(F)(F)C(F)(F)C2)ccc1-n1cc(OC)c(=O)c(-c2ccnn2-c2ccccc2)n1] | 516.5 |
| 16 | 4-fluoro-5-[5-methoxy-4-oxo-3-(1-phenyl-1H-pyrazol-5-yl)pyridazin-1(4H)-yl]-1,3,3-trimethyl-1,3-dihydro-2H-indol-2-one | 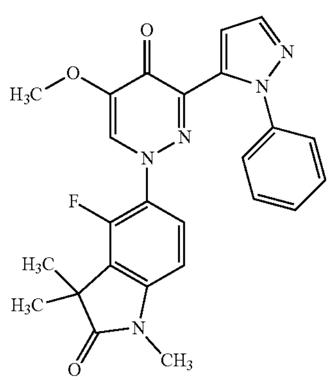 [SMILES: COc1cn(-c2ccc3c(c2F)C(C)(C)C(=O)N3C)nc(-c2ccnn2-c2ccccc2)c1=O] | 460.3 |

TABLE 4

| Ex. No. | IUPAC NAME | Structure | MS |
|---|---|---|---|
| 17 | 5-{3-[1-(3-chlorophenyl)-1H-pyrazol-5-yl]-5-methoxy-4-oxopyridazin-1(4H)-yl}-4-fluoro-1,3,3-trimethyl-1,3-dihydro-2H-indol-2-one | 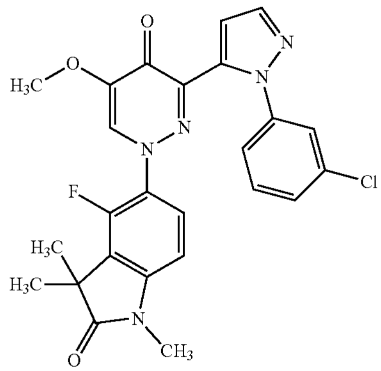 [SMILES: COc1cn(-c2ccc3c(c2F)C(C)(C)C(=O)N3C)nc(-c2ccnn2-c2cccc(Cl)c2)c1=O] | 494.2 |
| 18 | 4-fluoro-5-[5-methoxy-4-oxo-3-(1-phenyl-1H-pyrazol-5-yl)pyridazin-1(4H)-yl]-3,3-dimethyl-1-(2,2,2-trifluoroethyl)-1,3-dihydro-2H-indol-2-one | 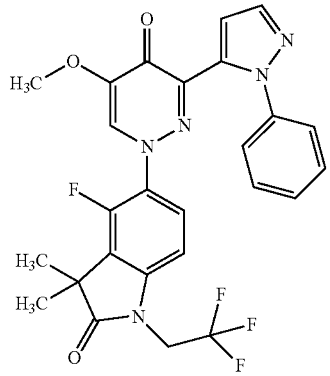 [SMILES: COc1cn(-c2ccc3c(c2F)C(C)(C)C(=O)N3CC(F)(F)F)nc(-c2ccnn2-c2ccccc2)c1=O] | 528.2 |
| 19 | 1-(2,2-difluoroethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one | 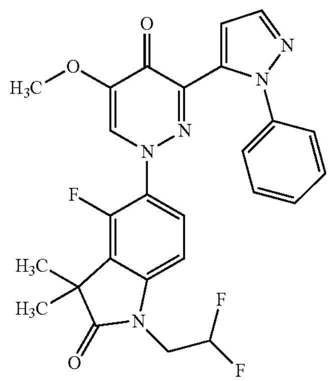 [SMILES: COc1cn(-c2ccc3c(c2F)C(C)(C)C(=O)N3CC(F)F)nc(-c2ccnn2-c2ccccc2)c1=O] | 510.4 |
| 20 | 4-fluoro-5-[5-methoxy-3-(3-methyl-1-phenyl-1H-pyrazol-5-yl)-4-oxopyridazin-1(4H)-yl]-3,3-dimethyl-1-(2,2,2-trifluoroethyl)-1,3-dihydro-2H-indol-2-one | 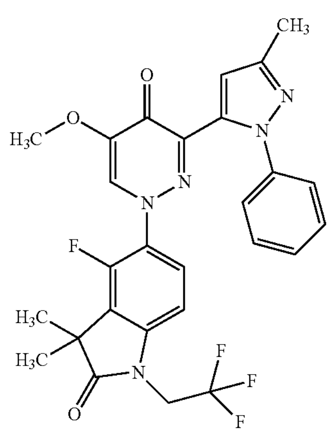 [SMILES: COc1cn(-c2ccc3c(c2F)C(C)(C)C(=O)N3CC(F)(F)F)nc(-c2cc(C)nn2-c2ccccc2)c1=O] | 542.3 |

TABLE 5

| Ex. No. | IUPAC NAME | Structure | MS |
|---|---|---|---|
| 21 | 1-(cyclopropylmethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one | 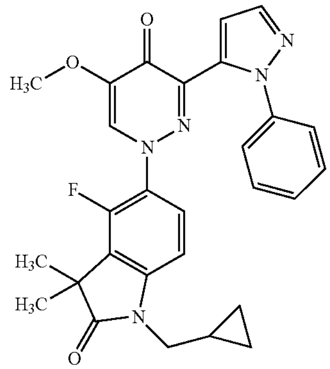 [SMILES: COc1cn(-c2ccc3c(c2F)C(C)(C)C(=O)N3CC2CC2)nc(-c2ccnn2-c2ccccc2)c1=O] | 500.4 |
| 22 | 5-methoxy-3-(1-phenyl-1H-pyrazol-5-yl)-1-pyridin-2-ylpyridazin-4(1H)-one | 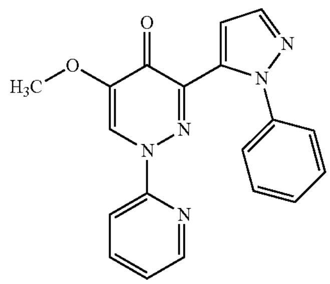 [SMILES: COc1cn(-c2ccccn2)nc(-c2ccnn2-c2ccccc2)c1=O] | 346.4 |
| 23 | 5-methoxy-1-(1-oxidopyridin-3-yl)-3-(1-phenyl-1H-pyrazol-5-yl)pyridazin-4(1H)-one | 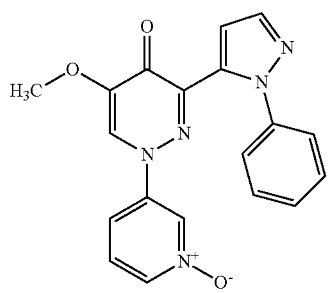 [SMILES: COc1cn(-c2ccc[n+]([O-])c2)nc(-c2ccnn2-c2ccccc2)c1=O] | 362.0 |
| 24 | 5-methoxy-3-(1-phenyl-1H-pyrazol-5-yl)-1-pyrazin-2-ylpyridazin-4(1H)-one | 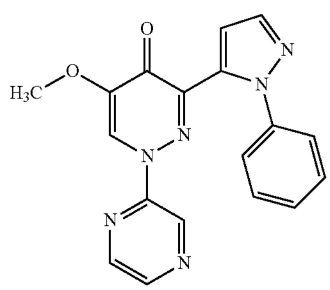 [SMILES: COc1cn(-c2cnccn2)nc(-c2ccnn2-c2ccccc2)c1=O] | 347.0 |
| 25 | 5-methoxy-3-(1-phenyl-1H-pyrazol-5-yl)-4H-1,3'-bipyridazin-4-one | 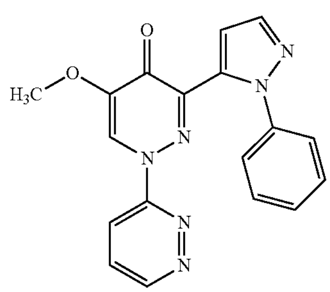 [SMILES: COc1cn(-c2cccnn2)nc(-c2ccnn2-c2ccccc2)c1=O] | 347.0 |

TABLE 6

| Ex. No. | IUPAC NAME | Structure | MS |
|---|---|---|---|
| 26 | 5-methoxy-3-(1-phenyl-1H-pyrazol-5-yl)-1-pyrimidin-5-ylpyridazin-4(1H)-one | 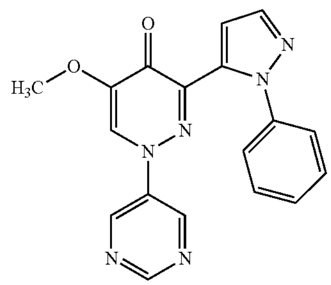 | 347.3 |
| 27 | 5-methoxy-3-(1-phenyl-1H-pyrazol-5-yl)-1-(1,3-thiazol-2-yl)pyridazin-4(1H)-one | 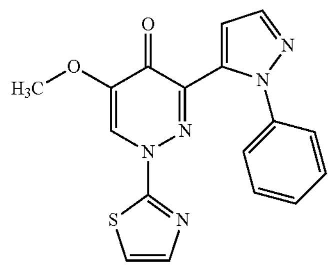 [SMILES: COc1cn(-c2nccs2)nc(-c2ccnn2-c2ccccc2)c1=O] | 352.3 |
| 32 | 5-methoxy-3-(1-phenyl-1H-pyrazol-5-yl)-1-[6-(3,3,4,4-tetrafluoropyrrolidin-1-yl)pyridin-3-yl]pyridazin-4(1H)-one | 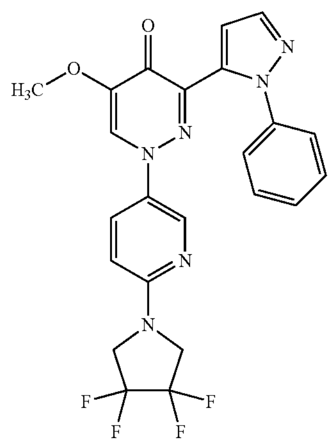 [SMILES: COc1cn(-c2ccc(N3CC(F)(F)C(F)(F)C3)nc2)nc(-c2ccnn2-c2ccccc2)c1=O] | 487.1 |
| 33 | 1-[6-(3,4-difluoro-1H-pyrrol-1-yl)pyridin-3-yl]-5-methoxy-3-(1-phenyl-1H-pyrazol-5-yl)pyrdizan-4(1H)-one | 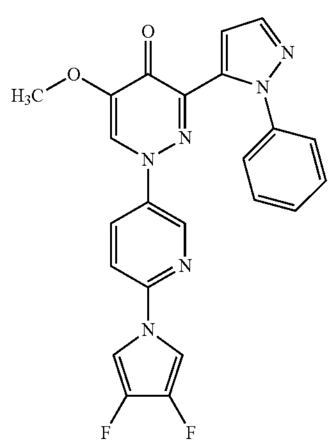 [SMILES: COc1cn(-c2ccc(-n3cc(F)c(F)c3)nc2)nc(-c2ccnn2-c2ccccc2)c1=O] | 447.1 |

TABLE 6-continued

| Ex. No. | IUPAC NAME | Structure | MS |
|---|---|---|---|
| 34 | 1-(1-benzyl-1H-pyrazol-4-yl)-5-methoxy-3-(1-phenyl-1H-pyrazol-5-yl)pyridazin-4(1H)-one | 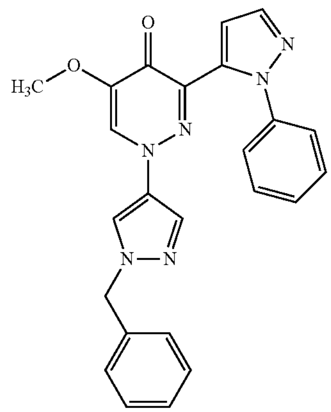 [SMILES: COc1cn(-c2cnn(Cc3ccccc3)c2)nc(-c2ccnn2-c2ccccc2)c1=O] | 425.3 |

TABLE 7

| Ex. No. | IUPAC NAME | Structure | MS |
|---|---|---|---|
| 35 | 5-methoxy-3-(1-phenyl-1H-pyrazol-5-yl)-1-[1-(2,2,2-trifluoroethyl)-1H-pyrazol-4-yl]pyridazin-4(1H)-one | 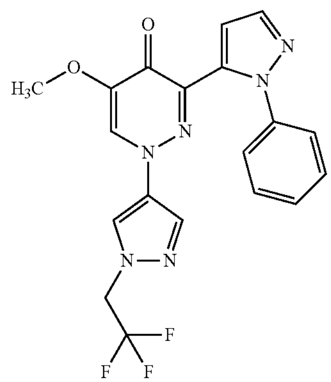 [SMILES: COc1cn(-c2cnn(CC(F)(F)F)c2)nc(-c2ccnn2-c2ccccc2)c1=O] | 417.4 |
| 36 | 1-[1-(cyclopropylmethyl)-1H-pyrazol-4-yl]-5-methoxy-3-(1-phenyl-1H-pyrazol-5-yl)pyridazin-4(1H)-one | 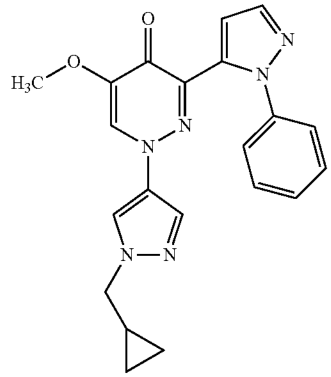 [SMILES: COc1cn(-c2cnn(CC3CC3)c2)nc(-c2ccnn2-c2ccccc2)c1=O] | 389.2 |

TABLE 7-continued

| Ex. No. | IUPAC NAME | Structure | MS |
|---|---|---|---|
| 37 | 1-[1-(dicyclopropylmethyl)-1H-pyrazol-4-yl]-5-methoxy-3-(1-phenyl-1H-pyrazol-5-yl)pyridazin-4(1H)-one | 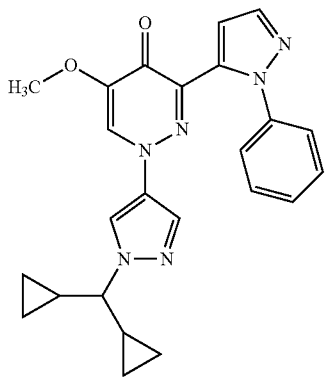 [SMILES: COc1cn(-c2cnn(C(C3CC3)C3CC3)c2)nc(-c2ccnn2-c2ccccc2)c1=O] | 429.1 |
| 38 | 5-methoxy-1-[1-(1-phenylethyl)-1H-pyrazol-4-yl]-3-(1-phenyl-1H-pyrazol-5-yl)pyridazin-4(1H)-one | 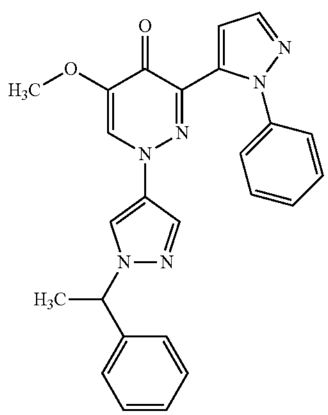 [SMILES: COc1cn(-c2cnn(C(C)c3ccccc3)c2)nc(-c2ccnn2-c2ccccc2)c1=O] | 439.4 |
| 39 | 5-methoxy-1-[1-(1-methylethyl)-1H-pyrazol-4-yl]-3-(1-phenyl-1H-pyrazol-5-yl)pyridazin-4(1H)-one | 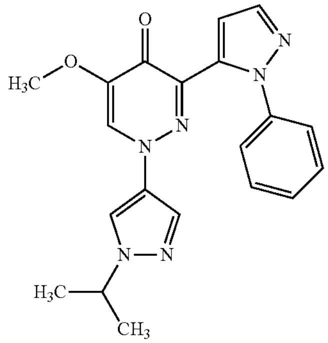 [SMILES: COc1cn(-c2cnn(C(C)C)c2)nc(-c2ccnn2-c2ccccc2)c1=O] | 377.0 |

TABLE 8
| Ex. No. | IUPAC NAME | Structure | MS |
|---|---|---|---|
| 40 | 1-[1-(1-cyclopropylmethyl)-1H-pyrazol-4-yl]-5-methoxy-3-(1-phenyl-1H-pyrazol-5-yl)pyridazin-4(1H)-one | 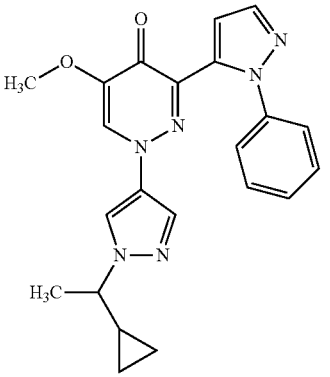 [SMILES: COc1cn(-c2cnn(C(C)C3CC3)c2)nc(-c2ccnn2-c2ccccc2)c1=O] | 403.1 |
| 41 | 5-methoxy-3-(1-methyl-1H-pyrazol-5-yl)-1-pyridin-3-ylpyridazin-4(1H)-one | 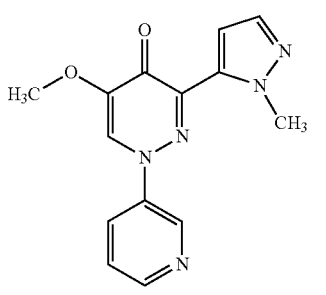 [SMILES: COc1cn(-c2cccnc2)nc(-c2ccnn2C)c1=O] | 284.2 |
| 42 | 5-methoxy-1-[1-(2-methylpropyl)-1H-pyrazol-4-yl]-3-(1-phenyl-1H-pyrazol-5-yl)pyridazin-4(1H)-one | 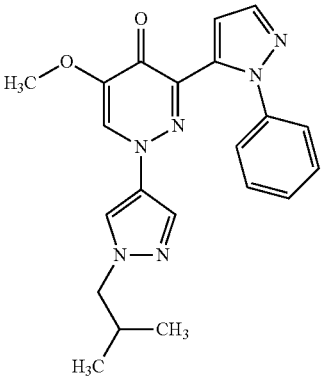 [SMILES: COc1cn(-c2cnn(CC(C)C)c2)nc(-c2ccnn2-c2ccccc2)c1=O] | 391.1 |
| 43 | 1-[1-(cyclobutylmethyl)-1H-pyrazol-4-yl]-5-methoxy-3-(1-phenyl-1H-pyrazol-5-yl)pyridazin-4(1H)-one | 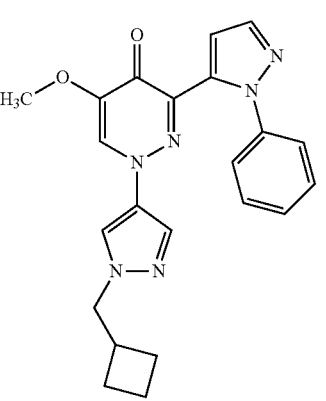 [SMILES: COc1cn(-c2cnn(CC3CCC3)c2)nc(-c2ccnn2-c2ccccc2)c1=O] | 403.1 |

TABLE 8-continued

| Ex. No. | IUPAC NAME | Structure | MS |
|---|---|---|---|
| 44 | 1-[1-(1-cyclopropylmethyl)-1H-pyrazol-4-yl]-5-methoxy-3-(1-phenyl-1H-pyrazol-5-yl)pyridazin-4(1H)-one | 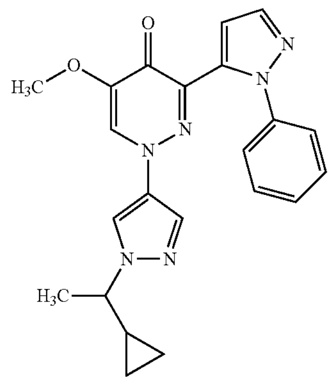 [SMILES: COc1cn(-c2cnn(C(C)C3CC3)c2)nc(-c2ccnn2-c2ccccc2)c1=O] | 403.1 |

TABLE 9

| Ex. No. | IUPAC NAME | Structure | MS |
|---|---|---|---|
| 45 | 1-[1-(1-cyclopropylethyl)-1H-pyrazol-4-yl]-5-methoxy-3-(1-phenyl-1H-pyrazol-5-yl)pyridazin-4(1H)-one | 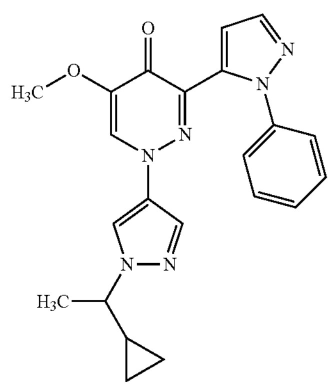 [SMILES: COc1cn(-c2cnn(C(C)C3CC3)c2)nc(-c2ccnn2-c2ccccc2)c1=O] | 403.1 |
| 46 | 1-(7-fluoro-1,2-dimethyl-1H-benzimidazol-6-yl)-5-methoxy-3-(1-phenyl-1H-pyrazol-5-yl)pyridazin-4(1H)-one | 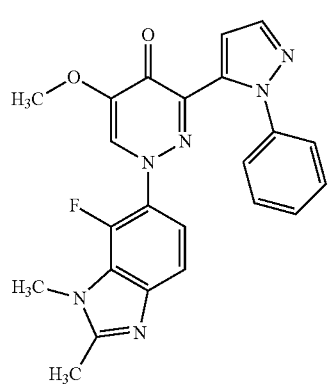 [SMILES: COc1cn(-c2ccc3nc(C)n(C)c3c2F)nc(-c2ccnn2-c2ccccc2)c1=O] | 431.3 |

TABLE 9-continued

| Ex. No. | IUPAC NAME | Structure | MS |
|---|---|---|---|
| 47 | 4'-fluoro-5'-[5-methoxy-4-oxo-3-(1-phenyl-1H-pyrazol-5-yl)pyridazin-1(4H)-yl]-1'-methylspiro[cyclobutane-1,3'-indol]-2'(1'H)-one | 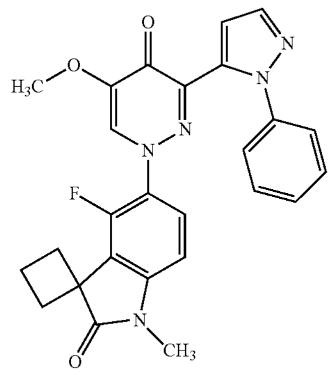 [SMILES: COc1cn(-c2ccc3c(c2F)C2(CCC2)C(=O)N3C)nc(-c2ccnn2-c2ccccc2)c1=O] | 472.3 |
| 48 | 4-fluoro-5-[5-methoxy-4-oxo-3-(1-phenyl-1H-pyrazol-5-yl)pyridazin-1(4H)-yl]-3,3-dimethyl-1-(1-methylethyl)-1,3-dihydro-2H-indol-2-one | 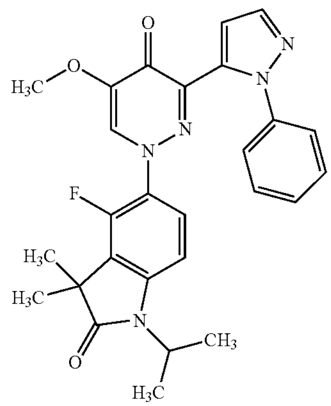 [SMILES: COc1cn(-c2ccc3c(c2F)C(C)(C)C(=O)N3C(C)C)nc(-c2ccnn2-c2ccccc2)c1=O] | 488.4 |
| 49 | 4'-fluoro-5'-[5-methoxy-4-oxo-3-(1-phenyl-1H-pyrazol-5-yl)pyridazin-1(4H)-yl]-1'-(1-methylethyl)spiro[cyclobutane-1,3'-indol]-2'(1'H)-one | 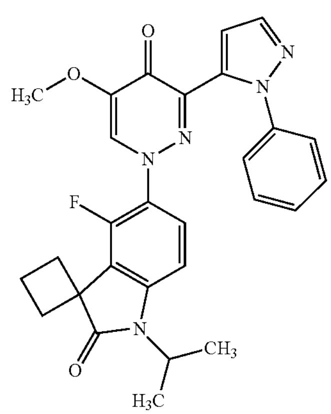 [SMILES: COc1cn(-c2ccc3c(c2F)C2(CCC2)C(=O)N3C(C)C)nc(-c2ccnn2-c2ccccc2)c1=O] | 500.4 |

TABLE 10

| Ex. No. | IUPAC NAME | Structure | MS |
|---|---|---|---|
| 50 | 1-cyclobutyl-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one | 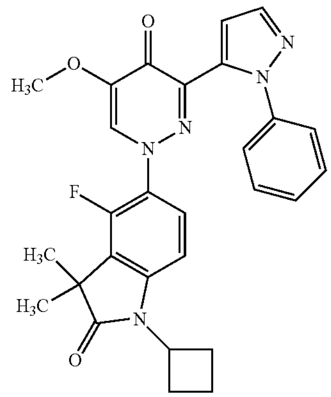 [SMILES: COc1cn(-c2ccc3c(c2F)C(C)(C)C(=O)N3C2CCC2)nc(-c2ccnn2-c2ccccc2)c1=O] | 500.4 |
| 51 | 1-[1-(cyclopropylmethyl)-1H-pyrazol-4-yl]-5-methoxy-3-(3-methyl-1-phenyl-1H-pyrazol-5-yl)pyridazin-4(1H)-one | 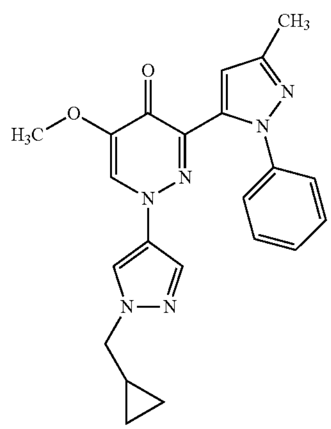 [SMILES: COc1cn(-c2cnn(CC3CC3)c2)nc(-c2cc(C)nn2-c2ccccc2)c1=O] | 403.4 |
| 52 | 5-methoxy-1-[2-methoxy-6-(3,3,4,4-tetrafluoropyrrolidin-1-yl)pyridin-3-yl]-3-(1-phenyl-1H-pyrazol-5-yl)pyridazin-4(1H)-one | 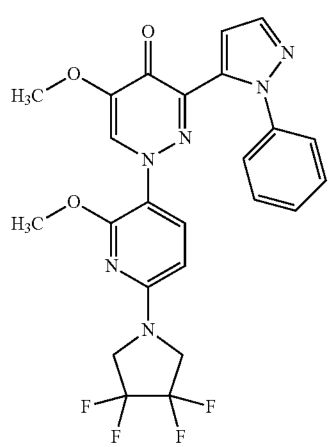 [SMILES: COc1nc(N2CC(F)(F)C(F)(F)C2)ccc1-n1cc(OC)c(=O)c(-c2ccnn2-c2ccccc2)n1] | 517.2 |

TABLE 10-continued

| Ex. No. | IUPAC NAME | Structure | MS |
|---|---|---|---|
| 53 | 1-[6-(3,4-difluoro-1H-pyrrol-1-yl)-2-methoxypyridin-3-yl]-5-methoxy-3-(1-phenyl-1H-pyrazol-5-yl)pyridazin-4(1H)-one | 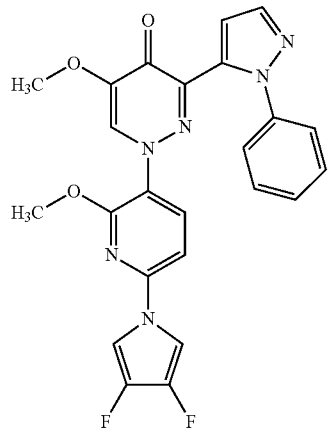 [SMILES: COc1nc(-n2cc(F)c(F)c2)ccc1-n1cc(OC)c(=O)c(-c2ccnn2-c2ccccc2)n1] | 477.1 |
| 54 | 5-methoxy-1-{1-[(1-methylcyclopropyl)methyl]-1H-pyrazol-4-yl}-3-(1-phenyl-1H-pyrazol-5-yl)pyridazin-4(1H)-one | 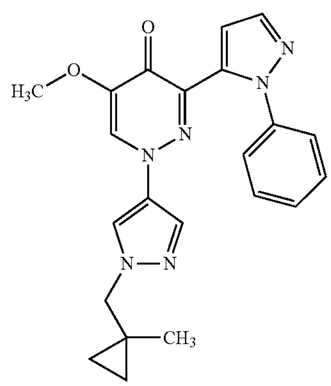 [SMILES: COc1cn(-c2cnn(CC3(C)CC3)c2)nc(-c2ccnn2-c2ccccc2)c1=O] | 403.1 |

TABLE 11

| Ex. No. | IUPAC NAME | Structure | MS |
|---|---|---|---|
| 55 | 5-methoxy-1-[1-(2,2,3,3,3-pentafluoropropyl)-1H-pyrazol-4-yl]-3-(1-phenyl-1H-pyrazol-5-yl)pyridazin-4(1H)-one | 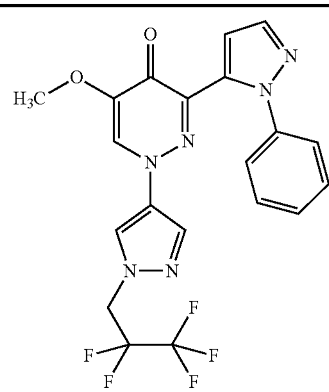 | 467.3 |

TABLE 11-continued

| Ex. No. | IUPAC NAME | Structure | MS |
|---|---|---|---|
| 56 | 5-amino-3-(1-phenyl-1H-pyrazol-5-yl)-1-[3-(trifluoromethyl)phenyl]pyridazin-4(1H)-one | 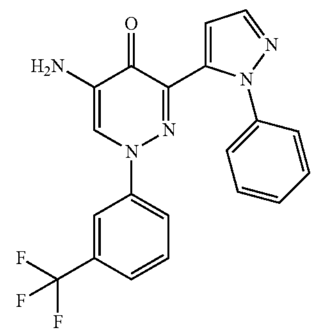 [SMILES: Nc1cn(-c2cccc(C(F)(F)F)c2)nc(-c2ccnn2-c2ccccc2)c1=O] | 398.4 |
| 57 | 5-(methylamino)-3-(1-phenyl-1H-pyrazol-5-yl)-1-[3-(trifluoromethyl)phenyl]pyridazin-4(1H)-one | 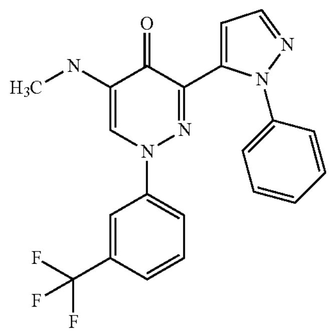 [SMILES: CNc1cn(-c2cccc(C(F)(F)F)c2)nc(-c2ccnn2-c2ccccc2)c1=O] | 412.4 |
| 58 | 5-(dimethylamino)-3-(1-phenyl-1H-pyrazol-5-yl)-1-[3-(trifluoromethyl)phenyl]pyridazin-4(1H)-one | 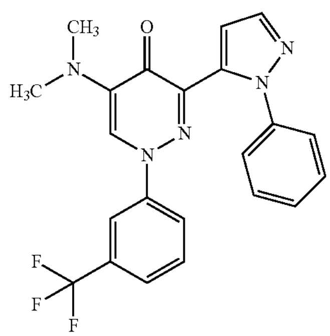 [SMILES: CN(C)c1cn(-c2cccc(C(F)(F)F)c2)nc(-c2ccnn2-c2ccccc2)c1=O] | 426.4 |
| 59 | 1-[2-(difluoromethoxy)-4-(3,3,4,4-tetrahydrofluoropyrrolidin-1-yl)phenyl]-5-methoxy-3-(1-phenyl-1H-pyrazol-5-yl)pyridazin-4(1H)-one | 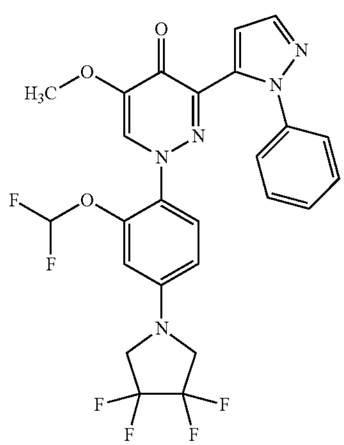 [SMILES: COc1cn(-c2ccc(N3CC(F)(F)C(F)(F)C3)cc2OC(F)F)nc(-c2ccnn2-c2ccccc2)c1=O] | 552.2 |

TABLE 12

| Ex. No. | IUPAC NAME | Structure | MS |
|---|---|---|---|
| 60 | 1-[2-fluoro-4-(5-methoxy-1H-pyrazol-1-yl)phenyl]-5-methoxy-3-(1-phenyl-1H-pyrazol-5-yl)pyridazin-4(1H)-one | 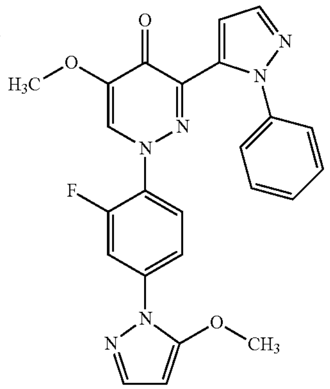 [SMILES: COc1cn(-c2ccc(-n3nccc3OC)cc2F)nc(-c2ccnn2-c2ccccc2)c1=O] | 459.2 |
| 61 | 1-{4-[5-(cyclopropylmethoxy)-1H-pyrazol-1-yl]-2-fluorophenyl}-5-methoxy-3-(1-phenyl-1H-pyrazol-5-yl)pyridazin-4(1H)-one | 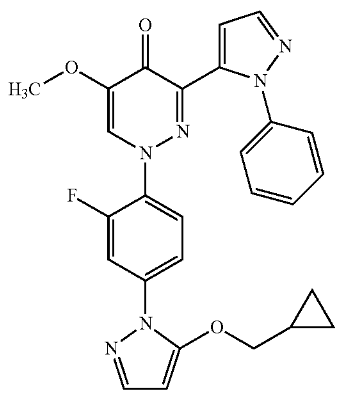 [SMILES: COc1cn(-c2ccc(-n3nccc3OCC3CC3)cc2F)nc(-c2ccnn2-c2ccccc2)c1=O] | 499.3 |
| 62 | 1-{2-fluoro-4-[5-(2,2,2-trifluoroethoxy)-1H-pyrazol-1-yl]phenyl}-5-methoxy-3-(1-phenyl-1H-pyrazol-5-yl)pyridazin-4(1H)-one | 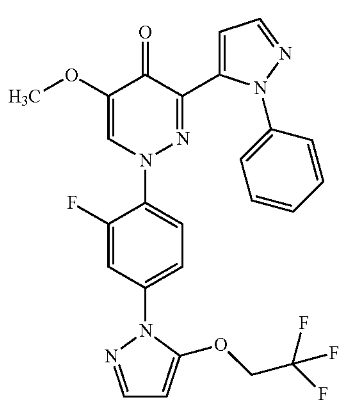 [SMILES: COc1cn(-c2ccc(-n3nccc3OCC(F)(F)F)cc2F)nc(-c2ccnn2-c2ccccc2)c1=O] | 527.3 |

TABLE 12-continued

| Ex. No. | IUPAC NAME | Structure | MS |
|---|---|---|---|
| 63 | 1-[4-(3,3-difluoropiperidin-1-yl)-2-fluorophenyl]-5-methoxy-3-(1-phenyl-1H-pyrazol-5-yl)pyridazin-4(1H)-one | 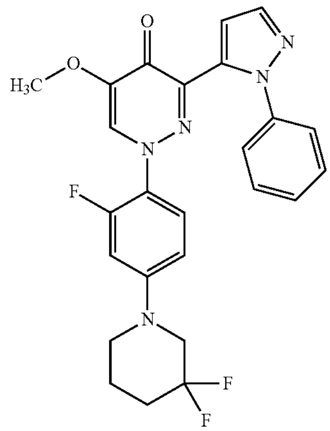 [SMILES: COc1cn(-c2ccc(N3CCCC(F)(F)C3)cc2F)nc(-c2ccnn2-c2ccccc2)c1=O] | 482.2 |
| 64 | 1-[2-fluoro-4-(3-methyl-2-oxopyrrolidin-1-yl)phenyl]-5-methoxy-3-(1-phenyl-1H-pyrazol-5-yl)pyridazin-4(1H)-one | 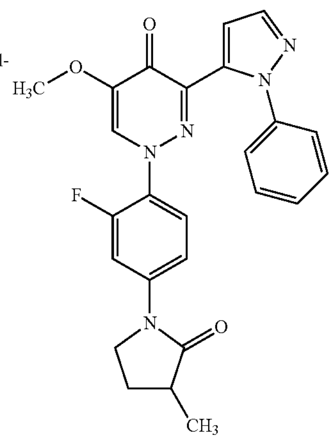 | 460.3 |

TABLE 13

| Ex. No. | IUPAC NAME | Structure | MS |
|---|---|---|---|
| 65 | 1-[2-fluoro-4-(2-oxopyrrolidin-1-yl)phenyl]-5-methoxy-3-(3-methyl-1-phenyl-1H-pyrazol-5-yl)pyridazin-4(1H)-one | 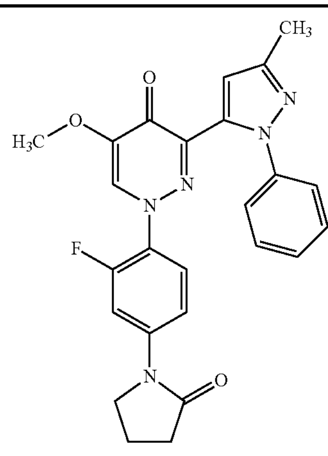 | 460.3 |

TABLE 13-continued
| Ex. No. | IUPAC NAME | Structure | MS |
|---|---|---|---|
| 66 | 3-[1-(3-chlorophenyl)-1H-pyrazol-5-yl]-1-(2-fluoro-4-iodophenyl)-5-methoxypyridazin-4(1H)-one | 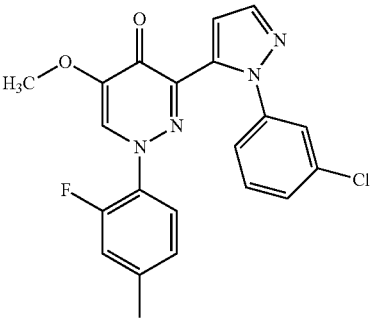 [SMILES: COc1cn(-c2ccc(C)cc2F)nc(-c2ccnn2-c2cccc(Cl)c2)c1=O] | 523.1 |
| 67 | 3-[1-(3-chlorophenyl)-1H-pyrazol-5-yl]-1-[2-fluoro-4-(2-oxopyrrolidin-1-yl)phenyl]-5-methoxypyridazin-4(1H)-one | 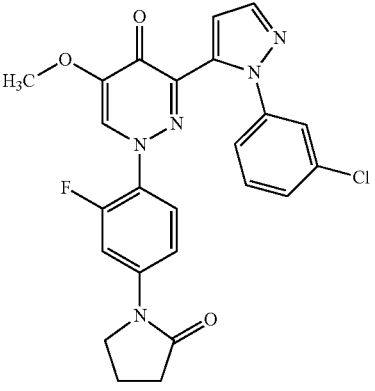 [SMILES: COc1cn(-c2ccc(N3CCCC3=O)cc2F)nc(-c2ccnn2-c2cccc(Cl)c2)c1=O] | 480.2 |
| 68 | 1-(2-fluoro-4-iodophenyl)-3-[1-(2-fluorophenyl)-1H-pyrazol-5-yl]-5-methoxypyridazin-4(1H)-one | 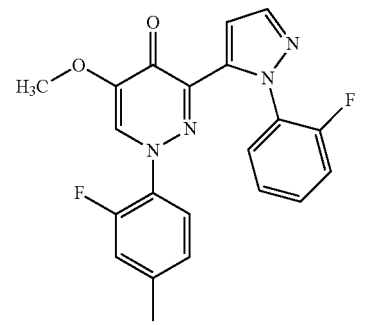 [SMILES: COc1cn(-c2ccc(C)cc2F)nc(-c2ccnn2-c2ccccc2F)c1=O] | 506.9 |
| 69 | 1-[2-fluoro-4-(2-oxopyrrolidin-1-yl)phenyl]-3-[1-(2-fluorophenyl)-1H-pyrazol-5-yl]-5-methoxypyridazin-4(1H)-one | 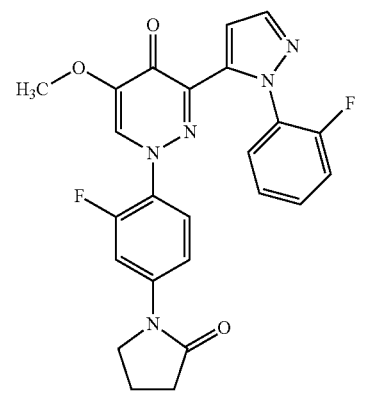 [SMILES: COc1cn(-c2ccc(N3CCCC3=O)cc2F)nc(-c2ccnn2-c2ccccc2F)c1=O] | 464.3 |

TABLE 14

| Ex. No. | IUPAC NAME | Structure | MS |
|---|---|---|---|
| 70 | 1-[2-(difluoromethoxy)-4-iodophenyl]-5-methoxy-3-(1-phenyl-1H-pyrazol-5-yl)pyridazin-4(1H)-one | 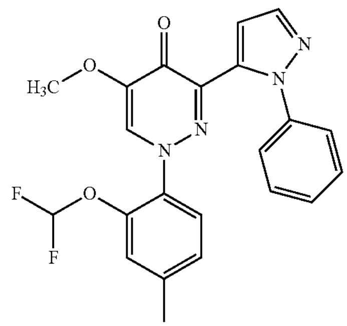 [SMILES: COc1cn(-c2ccc(C)cc2OC(F)F)nc(-c2ccnn2-c2ccccc2)c1=O] | 537.2 |
| 71 | 1-[2-(difluoromethoxy)-4-(1H-pyrazol-1-yl)phenyl]-5-methoxy-3-(1-phenyl-1H-pyrazol-5-yl)pyridazin-4(1H)-one | 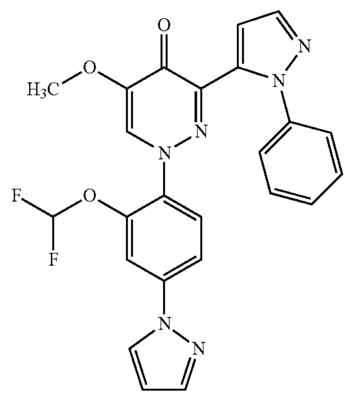 [SMILES: COc1cn(-c2ccc(-n3cccn3)cc2OC(F)F)nc(-c2ccnn2-c2ccccc2)c1=O] | 477.3 |
| 72 | 1-[2-(difluoromethoxy)-4-(2-oxopyrrolidin-1-yl)phenyl]-5-methoxy-3-(1-phenyl-1H-pyrazol-5-yl)pyridazin-4(1H)-one | 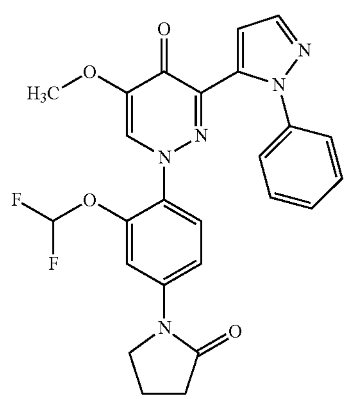 [SMILES: COc1cn(-c2ccc(N3CCCC3=O)cc2OC(F)F)nc(-c2ccnn2-c2ccccc2)c1=O] | 494.4 |
| 73 | 1-[2-fluoro-4-(2-methyl-5-oxopyrrolidin-1-yl)phenyl]-5-methoxy-3-(1-phenyl-1H-pyrazol-5-yl)pyridazin-4(1H)-one | 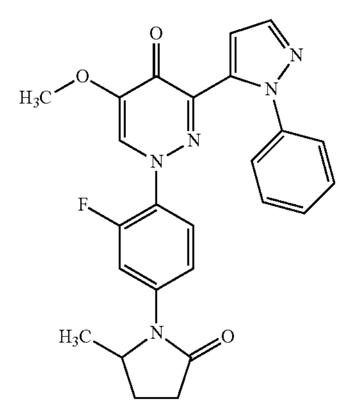 [SMILES: COc1cn(-c2ccc(N3C(=O)CCC3C)cc2F)nc(-c2ccnn2-c2ccccc2)c1=O] | 460.4 |

TABLE 14-continued

| Ex. No. | IUPAC NAME | Structure | MS |
|---|---|---|---|
| 74 | 5-methoxy-3-(1-phenyl-1H-pyrazol-5-yl)-1-[4-(1H-pyrazol-1-yl)-2-(2,2,2-trifluoroethoxy)phenyl]pyridazin-4(1H)-one | 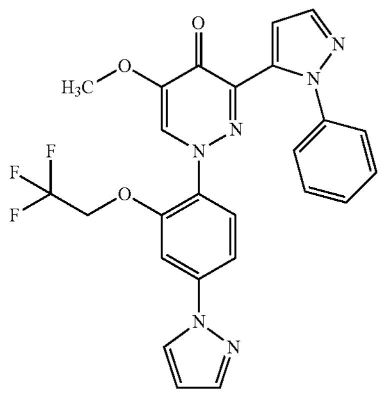 [SMILES: COc1cn(-c2ccc(-n3cccn3)cc2OCC(F)(F)F)nc(-c2ccnn2-c2ccccc2)c1=O] | 509.3 |

TABLE 15

| Ex. No. | IUPAC NAME | Structure | MS |
|---|---|---|---|
| 75 | 1-[2-(2,2-difluoroethoxy)-4-(1H-pyrazol-1-yl)phenyl]-5-methoxy-3-(1-phenyl-1H-pyrazol-5-yl)pyridazin-4(1H)-one | 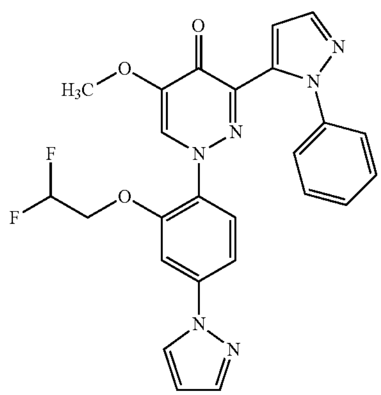 [SMILES: COc1cn(-c2ccc(-n3cccn3)cc2OCC(F)F)nc(-c2ccnn2-c2ccccc2)c1=O] | 491.3 |
| 76 | 1-[2-fluoro-4-(3-methyl-2-oxopyrrolidin-1-yl)phenyl]-5-methoxy-3-(1-phenyl-1H-pyrazol-5-yl)pyridazin-4(1H)-one | 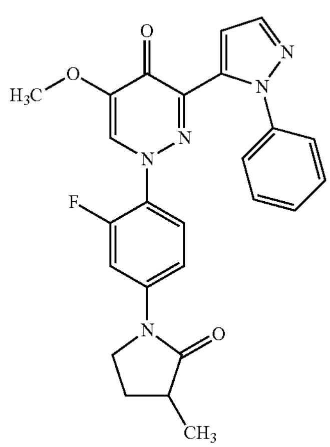 [SMILES: COc1cn(-c2ccc(N3CCC(C)C3=O)cc2F)nc(-c2ccnn2-c2ccccc2)c1=O] | 460.2 |

TABLE 15-continued

| Ex. No. | IUPAC NAME | Structure | MS |
|---|---|---|---|
| 77 | 1-[2-fluoro-4-(3-methyl-2-oxopyrrolidin-1-yl)phenyl]-5-methoxy-3-(1-phenyl-1H-pyrazol-5-yl)pyridazin-4(1H)-one | 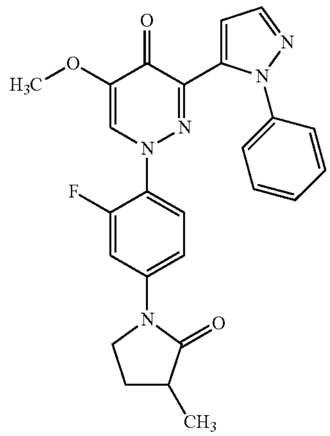 [SMILES: COc1cn(-c2ccc(N3CCC(C)C3=O)cc2F)nc(-c2ccnn2-c2ccccc2)c1=O] | 460.2 |
| 78 | 3-(1-cyclohexyl-1H-pyrazol-5-yl)-1-[2-fluoro-4-(1H-pyrazol-1-yl)phenyl]-5-methoxypyridazin-4(1H)-one | 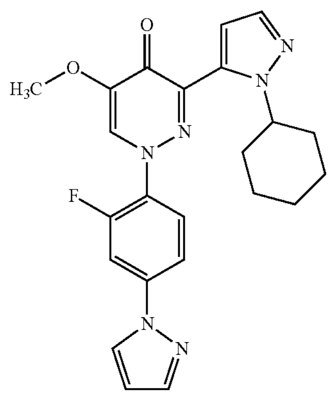 [SMILES: COc1cn(-c2ccc(-n3cccn3)cc2F)nc(-c2ccnn2C2CCCCC2)c1=O] | |

$^1$H NMR (300 MHz, DMSO-d$_6$) δ 1.19 (3H, d, J = 8.7 Hz), 1.76 (4H, d, J = 15.8 Hz), 1.86 (3H, brs), 3.84 (3H, s), 4.50 (1H, t, J = 5.1 Hz), 6.64 (1H, d, J = 1.9 Hz), 6.83 (1H, d, J = 1.9 Hz), 7.52 (1H, d, J = 1.9 Hz), 7.85 (1H, d, J = 1.9 Hz), 7.96 (2H, d, J = 4.5 Hz), 8.09 (1H, d, J = 11.7 Hz), 8.61 (1H, d, J = 1.5 Hz), 8.70 (1H, d, J = 2.3 Hz).

| 79 | 1-(4-iodophenyl)-5-methoxy-3-(1-phenyl-1H-pyrazol-5-yl)pyridazin-4(1H)-one | | 471.2 |

TABLE 16

| Ex. No. | IUPAC NAME | Structure | MS |
|---|---|---|---|
| 80 | 1-{4-[(2R,6S)-2,6-dimethylmorpholin-4-yl]-2-fluorophenyl}-5-methoxy-3-(1-phenyl-1H-pyrazol-5-yl)pyridazin-4(1H)-one | 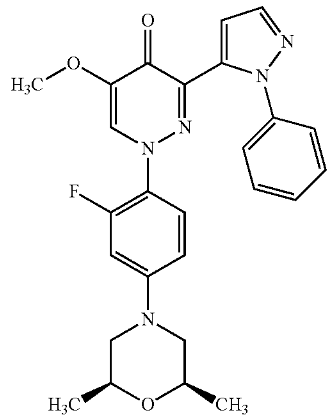 [SMILES: COc1cn(-c2ccc(N3C[C@@H](C)O[C@@H](C)C3)cc2F)nc(-c2ccnn2-c2ccccc2)c1=O] | 476.3 |
| 81 | 1-(4-iodo-2-methoxyphenyl)-5-methoxy-3-(1-phenyl-1H-pyrazol-5-yl)pyridazin-4(1H)-one | 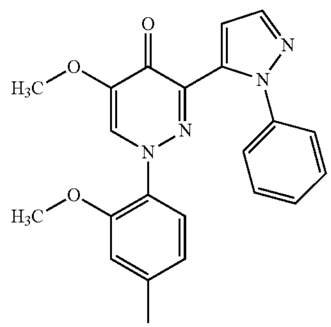 [SMILES: COc1cc(C)ccc1-n1cc(OC)c(=O)c(-c2ccnn2-c2ccccc2)n1] | 501.1 |
| 82 | 1-[2-fluoro-4-(1H-pyrazol-1-yl)phenyl]-5-methoxy-3-(1H-pyrazol-5-yl)pyridazin-4(1H)-one | 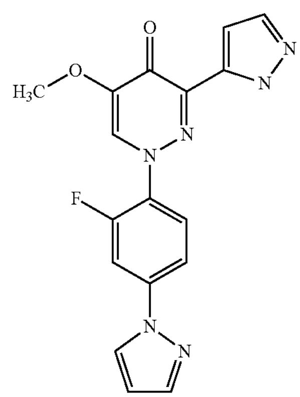 [SMILES: COc1cn(-c2ccc(-n3cccn3)cc2F)nc(-c2ccn[nH]2)c1=O] | 353.3 |
| 83 | 1-[2-fluoro-4-(8-oxa-3-azabicyclo[3.2.1]oct-3-yl)phenyl]-5-methoxy-3-(1-phenyl-1H-pyrazol-5-yl)pyridazin-4(1H)-one | 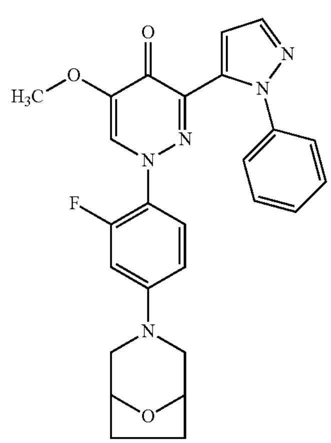 [SMILES: COc1cn(-c2ccc(N3CC4CCC(C3)O4)cc2F)nc(-c2ccnn2-c2ccccc2)c1=O] | 474.5 |

TABLE 16-continued

| Ex. No. | IUPAC NAME | Structure | MS |
|---|---|---|---|
| 84 | 1-[2-fluoro-4-(1,4-oxazepan-4-yl)phenyl]-5-methoxy-3-(1-phenyl-1H-pyrazol-5-yl)pyridazin-4(1H)-one | 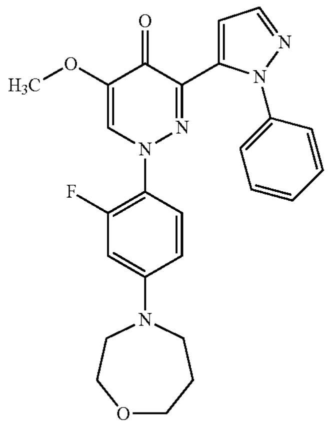 [SMILES: COc1cn(-c2ccc(N3CCCOCC3)cc2F)nc(-c2ccnn2-c2ccccc2)c1=O] | 462.4 |

TABLE 17

| Ex. No. | IUPAC NAME | Structure | MS |
|---|---|---|---|
| 85 | 5-methoxy-6-methyl-3-(1-phenyl-1H-pyrazol-5-yl)-1-[4-(1H-pyrazol-1-yl)phenyl]pyridazin-4(1H)-one | 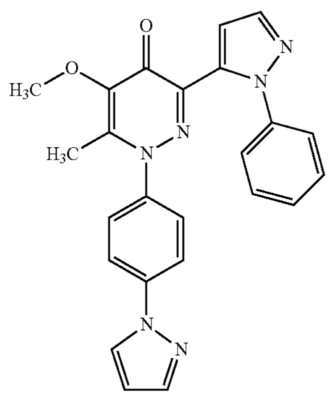 [SMILES: COc1c(C)n(-c2ccc(-n3cccn3)cc2)nc(-c2ccnn2-c2ccccc2)c1=O] | 425.3 |
| 86 | 5-methoxy-6-methyl-1-[4-(2-oxopyrrolidin-1-yl)phenyl]-3-(1-phenyl-1H-pyrazol-5-yl)pyridazin-4(1H)-one | 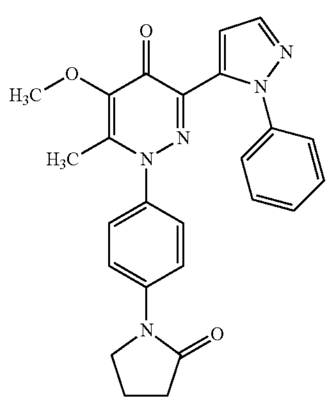 [SMILES: COc1c(C)n(-c2ccc(N3CCCC3=O)cc2)nc(-c2ccnn2-c2ccccc2)c1=O] | 442.3 |

TABLE 17-continued

| Ex. No. | IUPAC NAME | Structure | MS |
|---|---|---|---|
| 87 | 1-[2-fluoro-4-(1H-pyazol-1-yl)phenyl]-5-methoxy-3-(1-methyl-1H-pyrazol-3-yl)pyridazin-4(1H)-one | 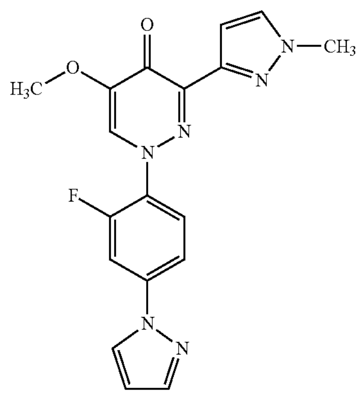 | 367.1 |
| 88 | 1-[2-fluoro-4-(1H-pyrazol-1-yl)phenyl]-5-methoxy-3-(1-methyl-1H-pyrazol-5-yl)pyridazin-4(1H)-one | 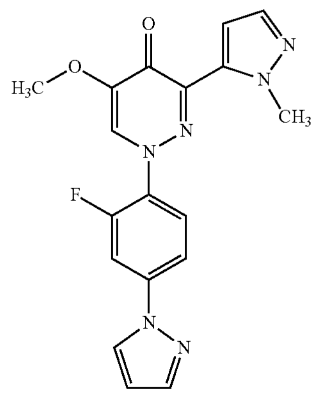 [SMILES: COc1cn(-c2ccc(-n3cccn3)cc2F)nc(-c2ccnn2C)c1=O] | 367.0 |
| 89 | 1-[4-(3,3-dimethyl-2-oxopyrrolidin-1-yl)-2-fluorophenyl]-5-methoxy-3-(1-phenyl-1H-pyrazol-5-yl)pyridazin-4(1H)-one | 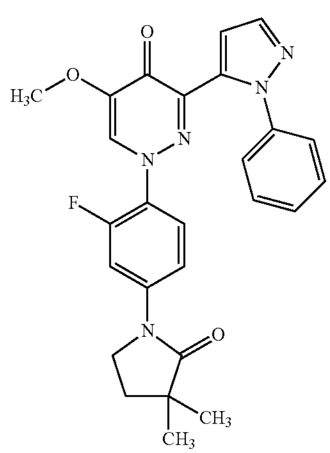 [SMILES: COc1cn(-c2ccc(N3CCC(C)(C)C3=O)cc2F)nc(-c2ccnn2-c2ccccc2)c1=O] | 474.4 |

TABLE 18

| Ex. No. | IUPAC NAME | Structure | MS |
|---|---|---|---|
| 90 | 1-[4-(3,3-dimethyl-2-oxopyrrolidin-1-yl)-2-methoxyphenyl]-5-methoxy-3-(1-phenyl-1H-pyrazol-5-yl)pyridazin-4(1H)-one | 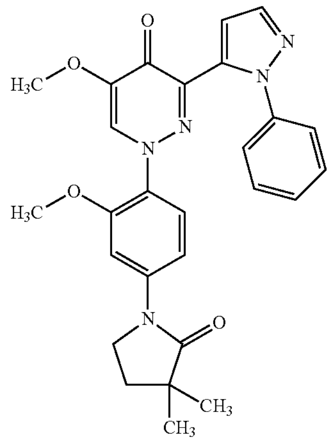 [SMILES: COc1cc(N2CCC(C)(C)C2=O)ccc1-n1cc(OC)c(=O)c(-c2ccnn2-c2ccccc2)n1] | 486.4 |
| 91 | 5-methoxy-3-(1-phenyl-1H-pyrazol-5-yl)-1-[4-(1H-pyrazol-1-yl)phenyl]pyridazin-4(1H)-one | 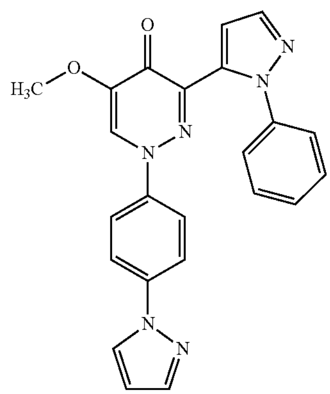 [SMILES: COc1cn(-c2ccc(-n3cccn3)cc2)nc(-c2ccnn2-c2ccccc2)c1=O] | 411.4 |
| 92 | 1-[2-(difluoromethoxy)-4-(3,3-dimethyl-2-oxopyrrolidin-1-yl)phenyl]-5-methoxy-3-(1-phenyl-1H-pyrazol-5-yl)pyridazin-4(1H)-one | 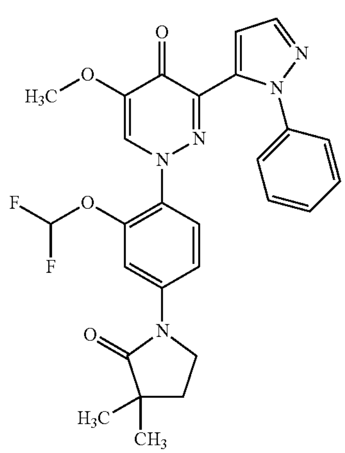 [SMILES: COc1cn(-c2ccc(N3CCC(C)(C)C3=O)cc2OC(F)F)nc(-c2ccnn2-c2ccccc2)c1=O] | 522.5 |

TABLE 18-continued

| Ex. No. | IUPAC NAME | Structure | MS |
|---|---|---|---|
| 93 | 1-(2-fluoro-4-iodophenyl)-5-methoxy-3-(2-phenyl-1H-imidazol-1-yl)pyridazin-4(1H)-one | 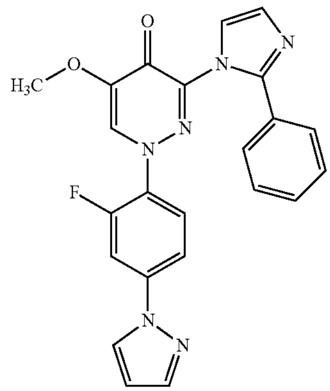 [SMILES: COc1cn(-c2ccc(-n3cccn3)cc2F)nc(-n2ccnc2-c2ccccc2)c1=O] | 488.9 |
| 94 | 1-[2-fluoro-4-(1H-pyrazol-1-yl)phenyl]-5-methoxy-3-(2-phenyl-1H-imidazol-1-yl)pyridazin-4(1H)-one | 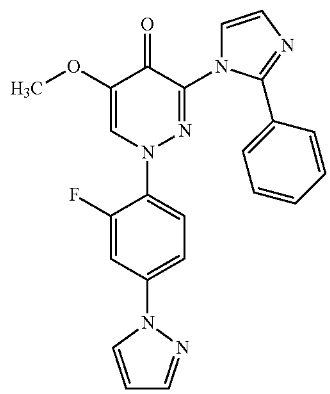 [SMILES: COc1cn(-c2ccc(-n3cccn3)cc2F)nc(-n2ccnc2-c2ccccc2)c1=O] | 429.1 |

TABLE 19

| Ex. No. | IUPAC NAME | Structure | MS |
|---|---|---|---|
| 95 | 1-[2-fluoro-3-(1H-pyrazol-1-yl)phenyl]-5-methoxy-3-(1-phenyl-1H-pyrazol-5-yl)pyridazin-4(1H)-one | 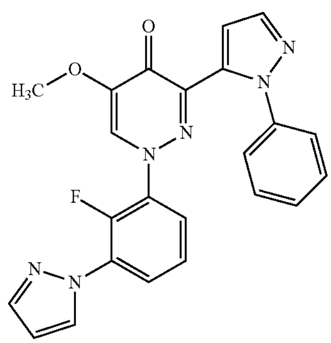 [SMILES: COc1cn(-c2cccc(-n3cccn3)c2F)nc(-c2ccnn2-c2ccccc2)c1=O] | 429.1 |

TABLE 19-continued

| Ex. No. | IUPAC NAME | Structure | MS |
|---|---|---|---|
| 96 | 1-[2-(2,2-difluoroethoxy)-4-(3,4-difluoro-1H-pyrrol-1-yl)phenyl]-5-methoxy-3-(1-phenyl-1H-pyrazol-5-yl)pyridazin-4(1H)-one | 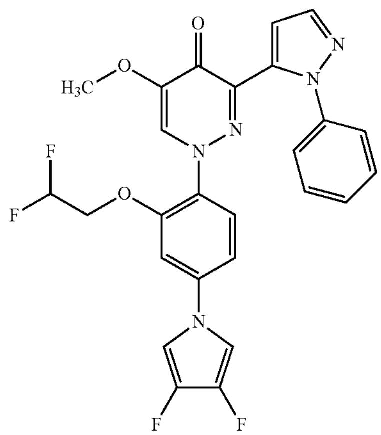 [SMILES: COc1cn(-c2ccc(-n3cc(F)c(F)c3)cc2OCC(F)F)nc(-c2ccnn2-c2ccccc2)c1=O] | 526.5 |
| 97 | 3-[1-(4-fluorophenyl)-1H-pyrazol-5-yl]-1-[2-fluoro-4-(1H-pyrazol-1-yl)phenyl]-5-methoxypyridazin-4(1H)-one | 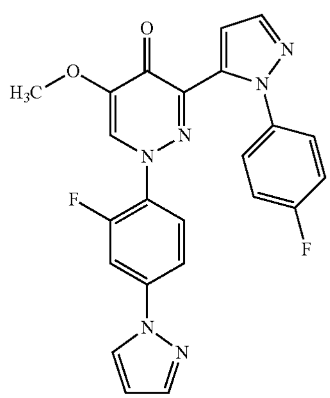 [SMILES: COc1cn(-c2ccc(-n3cccn3)cc2F)nc(-c2ccnn2-c2ccc(F)cc2)c1=O] | 447.4 |
| 98 | 3-{1-[3-(benzyloxy)phenyl]-1H-pyrazol-5-yl}-1-[2-fluoro-4-(1H-pyrazol-1-yl)phenyl]-5-methoxypyridazin-4(1H)-one | 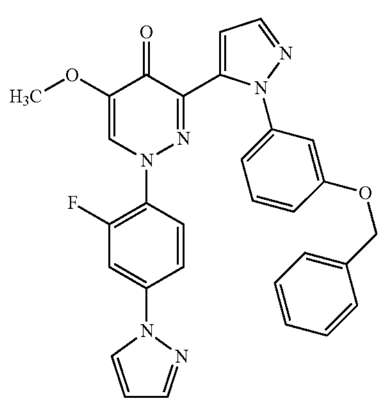 [SMILES: COc1cn(-c2ccc(-n3cccn3)cc2F)nc(-c2ccnn2-c2cccc(OCc3ccccc3)c2)c1=O] | 535.3 |

TABLE 20

| Ex. No. | IUPAC NAME | Structure | MS |
|---|---|---|---|
| 99 | 1-[2-fluoro-4-(1H-pyrazol-1-yl)phenyl]-3-[1-(3-hydroxyphenyl)-1H-pyrazol-5-yl]-5-methoxypyridazin-4(1H)-one | 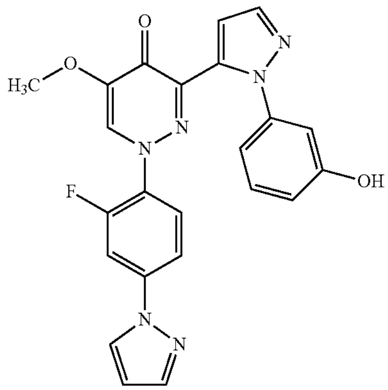 [SMILES: COc1cn(-c2ccc(-n3cccn3)cc2F)nc(-c2ccnn2-c2cccc(O)c2)c1=O] | 445.1 |
| 100 | 3-{1-[3-(cyclopropylmethoxy)phenyl]-1H-pyrazol-5-yl}-1-[2-fluoro-4-(1H-pyrazol-1-yl)phenyl]-5-methoxypyridazin-4(1H)-one | 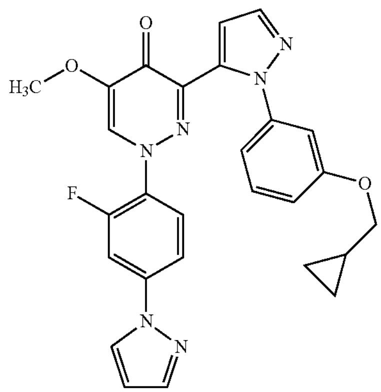 [SMILES: COc1cn(-c2ccc(-n3cccn3)cc2F)nc(-c2ccnn2-c2cccc(OCC3CC3)c2)c1=O] | 499.4 |
| 101 | 1-[2-fluoro-4-(4-hydroxy-1H-pyrazol-1-yl)phenyl]-5-methoxy-3-(1-phenyl-1H-pyrazol-5-yl)pyridazin-4(1H)-one | 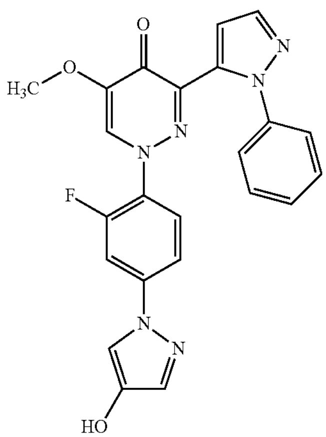 [SMILES: COc1cn(-c2ccc(-n3cc(O)cn3)cc2F)nc(-c2ccnn2-c2ccccc2)c1=O] | 445.1 |

TABLE 20-continued

| Ex. No. | IUPAC NAME | Structure | MS |
|---|---|---|---|
| 102 | 1-[2-fluoro-4-(3-hydroxy-1H-pyrazol-1-yl)phenyl]-5-methoxy-3-(1-phenyl-1H-pyrazol-5-yl)pyridazin-4(1H)-one | 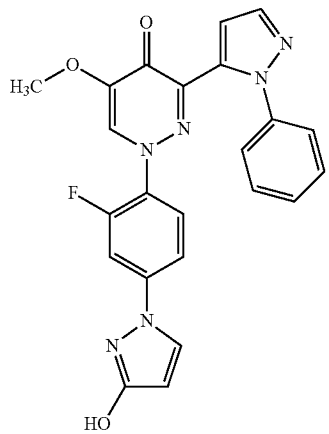 [SMILES: COc1cn(-c2ccc(-n3ccc(O)n3)cc2F)nc(-c2ccnn2-c2ccccc2)c1=O] | 445.1 |

Formulation Example 1

| | | |
|---|---|---|
| (1) Compound of the Example 16 | 10.0 g | |
| (2) Lactose | 70.0 g | |
| (3) Cornstarch | 50.0 g | |
| (4) Soluble starch | 7.0 g | |
| (5) Magnesium stearate | 3.0 g | |

The compound of Example 16 (10.0 g) and magnesium stearate (3.0 g) are granulated with an aqueous solution (70 ml) of soluble starch (7.0 g as soluble starch), dried, and the resulting mixture is mixed with lactose (70.0 g) and cornstarch (50.0 g) (lactose, cornstarch, soluble starch and magnesium stearate are all products on the Japanese Pharmacopoeia). The mixture is compressed to give tablets.

Experimental Example 1

PDE10A Enzyme Activity Inhibition Test

Human PDE10A full-length gene was transfected into Sf9 or COS-7 cells, the cells were disrupted and centrifuged, and human PDE10A enzyme was obtained from the residue. The enzyme extracted from Sf9 cells was partially purified using His-tag affinity column. The enzyme was stored at −70° C. until use. The PDE activity was measured using an SPA (Scintillation Proximity Assay) (GE Healthcare). To measure the inhibitory activity of the compound, 10 μL of serially diluted compound was reacted with 20 μL of PDE enzyme in an assay buffer (50 mM HEPES-NaOH, 8.3 mM $MgCl_2$, 1.7 mM EGTA, 0.1% BSA (pH 7.4)) for min at room temperature. The final concentration of DMSO in the reaction mixture was 1 percent. The compounds were evaluated in duplicate in 96-well half-area plates (Corning). To start the reaction, 10 μL of substrate [$^3$H] cGMP (25 and 50 nM; GE Healthcare and PerkinElmer, respectively) was added to 40 μL. After 60 min of reaction at room temperature, yttrium SPA beads containing zinc sulphate were added (6 mg/mL, 20 μL) to terminate the PDE reaction. After standing still for 1 hr, the measurement was performed using a scintillation counter (PerkinElmer) and the PDE10A enzyme activity inhibition rate was calculated. The inhibition rate was calculated based on the control containing enzyme and DMSO as 0% and the control without enzyme as 100%. The results are shown in Tables 21 and 22.

TABLE 21

| Example No. | $IC_{50}$<br>A: 10 nM ≥<br>B: 10~200 nM | Inhibition rate (%)<br>(100 nM) |
|---|---|---|
| 12 | A | 100 |
| 15 | A | 99 |
| 16 | A | 100 |
| 17 | A | 99 |
| 18 | A | 100 |
| 19 | A | 102 |
| 20 | A | 100 |
| 21 | A | 100 |
| 22 | A | 100 |
| 24 | A | 97 |
| 25 | B | 88 |
| 26 | B | 85 |
| 27 | A | 98 |
| 32 | A | 100 |
| 33 | A | 96 |

TABLE 22

| Example No. | $IC_{50}$<br>A: 10 nM ≥<br>B: 10~200 nM | Inhibition rate (%)<br>(100 nM) |
|---|---|---|
| 35 | A | 100 |
| 36 | A | 102 |
| 42 | A | 100 |
| 43 | A | 99 |
| 44 | A | 102 |
| 45 | A | 100 |
| 46 | A | 98 |
| 47 | A | 101 |
| 48 | A | 101 |
| 49 | A | 101 |
| 50 | A | 101 |
| 51 | A | 102 |
| 52 | A | 101 |
| 53 | A | 97 |
| 54 | A | 101 |

Experimental Example 2

Animals

Male ICR mice were supplied by CLEA Japan, Inc (Japan). After arrival to the vivarium, animals were allowed a minimum of 1 week for acclimation and used for the test. They were housed under a 12:12-h light/dark cycle in a temperature- and humidity-controlled laboratory and allowed food and water ad libitum. The care and use of the animals and the experimental protocols used in this research were approved by the Experimental Animal Care and Use Committee of Takeda Pharmaceutical Company, Ltd (Osaka, Japan).

Drug Administration

The test compound was suspended in 0.5% methylcellulose in distilled water, and orally administered (p.o.). MK-801 hydrogen maleate ((5R,10S)-(+)-5-methyl-10,11-dihydro-5H-dibenzo[a,d]cyclohepten-5,10-imine hydrogen maleate (Sigma-Aldrich, St Louis, Mo.) was dissolved in saline, and administered subcutaneously (s.c.). All drugs were dosed in a volume of 20 mL/kg body weight for mice.

Inhibition of MK-801-Induced Locomotor Hyperactivity

The evaluation of the extent of hyperlocomotion induced by psychostimulants (e.g., amphetamine, cocaine, methamphetamine, MK-801 and phencyclidine) in rodents has been widely used as animal models of psychotic diseases (Schizophrenia Bulletin 2010, vol. 36: 1066-1072; Psychopharmacology 1999, vol. 145: 237-250). The compounds were tested for their ability to suppress MK-801-induced hyperlocomotion in mice. Male ICR mice (30-43 g) were acclimated in locomotor chambers with infrared sensors (BrainScienceIdea Co., Ltd. Japan) for at least 60 minutes. After the acclimation, animals were orally administered with either vehicle or the compound (3 mg/kg, p.o.), and placed back in the locomotor chambers. After 60 minutes administration of the compound, the animals were taken out again from the locomotor chambers, subcutaneously administrated with vehicle (physiological saline) or MK-801 (0.3 mg/kg), and placed back in the locomotor chambers. Locomotor activities were counted every minute, and accumulated counts (120 minutes after administration of MK-801) were calculated in each treatment group. All data were shown as mean plus standard errors of the mean (n=6-7) and analyzed using Welch's t-test for the control group and the MK-801 single administration group (significant difference at P<0.05), and Steel test for the comparison of the vehicle administration group and the compound administration group (significant difference at P<0.05). The results are shown in FIG. 1.

The compounds in FIG. 1 correspond to the following Examples.
Compound A (Example 17)
Compound B (Example 21)
Compound C (Example 44)
Compound D (Example 52)

By oral administration 60 min before the treatment of MK-801 (0.3 mg/kg, s.c.); the compound showed a significant suppressive action on the amount of MK-801 induced spontaneous locomotor hyperactivity. **P<0.01 (comparison between control group and MK-801 single administration group, Welch's t-test). #P<0.05 (comparison between vehicle administration group and compound administration group, Steel test).

Formulation Example 1

| | |
|---|---|
| (1) Compound of the Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound of Example 16 (10.0 g) and magnesium stearate (3.0 g) are granulated with an aqueous solution (70 ml) of soluble starch (7.0 g as soluble starch), dried, and the resulting mixture is mixed with lactose (70.0 g) and cornstarch (50.0 g) (lactose, cornstarch, soluble starch and magnesium stearate are all products on the Japanese Pharmacopoeia). The mixture is compressed to give tablets.

INDUSTRIAL APPLICABILITY

The medicament of the present invention can be utilized as a medicament for the prophylaxis or treatment of psychotic diseases such as schizophrenia and the like, and the like.

This application is based on a patent application No. 2010-175374 filed in Japan, the contents of which are incorporated in full herein.

Although the present invention have been presented or described by referring to preferred embodiments of this invention, it will, however, be understood by those of ordinary skill in the art that various modifications may be made to the forms and details without departing from the scope of the invention as set forth in the appended claims.

The invention claimed is:

1. A compound represented by formula (1)

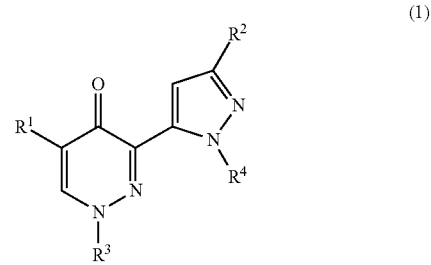

wherein
$R^1$ is an optionally substituted $C_{1-6}$ alkoxy group,
$R^2$ is a hydrogen atom or an optionally substituted $C_{1-6}$ alkyl group,
$R^3$ is selected from the group consisting of the following fused rings

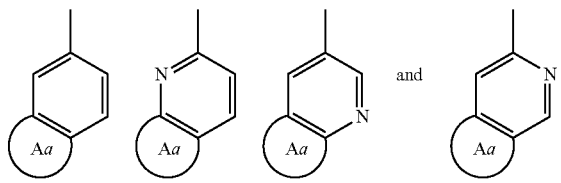

wherein
ring Aa is an optionally substituted 5- or 6-membered heterocycle wherein the substituents for ring Aa are optionally bonded to form a ring; and
the benzene ring or pyridine ring contained in the fused ring is optionally substituted, or

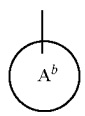

wherein
ring $A^b$ is a substituted pyridine ring, an optionally substituted pyrazole ring, an optionally substituted thiazole ring, an optionally substituted pyrazine ring, an optionally substituted pyridazine ring, an optionally substituted pyrimidine ring or an optionally substituted imidazole ring, and
$R^4$ is an optionally substituted $C_{1-6}$ alkyl group or an optionally substituted phenyl group, provided that the following compounds:
a compound wherein $R^1$ is a $C_{1-6}$ alkoxy group substituted by substituent(s) having optionally substituted cyclic group(s),
5-methoxy-3-(1-phenyl-1H-pyrazol-5-yl)-1-(2,2,6-trifluoro-1,3-benzodioxol-5-yl)pyridazin-4(1H)-one, and
5-methoxy-1-(2,2,3,3,7-pentafluoro-2,3-dihydro-1,4-benzodioxin-6-yl)-3-(1-phenyl-1H-pyrazol-5-yl)pyridazin-4(1H)-one
are excluded,
or a salt thereof.

2. The compound or salt of claim 1, wherein $R^3$ is

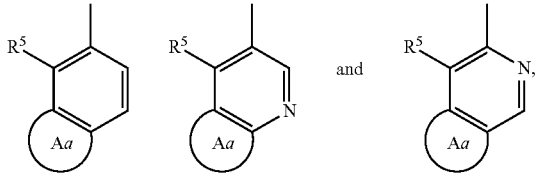

wherein
$R^5$ is a substituent, and
Aa, the benzene ring and the pyridine ring are as defined in claim 1.

3. The compound or salt of claim 2, wherein $R^5$ is a halogen atom or an optionally substituted $C_{1-6}$ alkoxy group.

4. The compound or salt of claim 1, wherein $R^3$ is

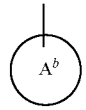

wherein ring $A^b$ is a substituted pyridine ring or a substituted pyrazole ring.

5. 5-{3-[1-(3-Chlorophenyl)-1H-pyrazol-5-yl]-5-methoxy-4-oxopyridazin-1(4H)-yl}-4-fluoro-1,3,3-trimethyl-1,3-dihydro-2H-indol-2-one or a salt thereof.

6. 1-(Cyclopropylmethyl)-4-fluoro-5-[5-methoxy-4-oxo-3-(1-phenyl-1H-pyrazol-5-yl)pyridazin-1(4H)-yl]-3,3-dimethyl-1,3-dihydro-2H-indol-2-one or a salt thereof.

7. 1-[1-(1-Cyclopropylethyl)-1H-pyrazol-4-yl]-5-methoxy-3-(1-phenyl-1H-pyrazol-5-yl)pyridazin-4(1H)-one or a salt thereof.

8. 5-Methoxy-1-[2-methoxy-6-(3,3,4,4-tetrafluoropyrrolidin-1-yl)pyridin-3-yl]-3-(1-phenyl-1H-pyrazol-5-yl)pyridazin-4(1H)-one or a salt thereof.

9. 1-[6-(3,4-difluoro-1H-pyrrol-1-yl)-2-methoxypyridin-3-yl]-5-methoxy-3-(1-phenyl-1H-pyrazol-5-yl)pyridazin-4(1H)-one or a salt thereof.

10. A pharmaceutical composition comprising the compound or salt of claim 1, and a pharmacologically acceptable carrier.

11. The pharmaceutical composition of claim 10, which is a phosphodiesterase 10A inhibitor.

12. A method for treating schizophrenia which comprises administering an effective amount of the compound or salt of claim 1 to a mammal.

* * * * *